(12) United States Patent
Jarjour et al.

(10) Patent No.: US 11,779,654 B2
(45) Date of Patent: Oct. 10, 2023

(54) PCSK9 ENDONUCLEASE VARIANTS, COMPOSITIONS, AND METHODS OF USE

(71) Applicant: 2seventy bio, Inc., Cambridge, MA (US)

(72) Inventors: Jordan Jarjour, Seattle, WA (US); Kyle Havens, Seattle, WA (US); Michael Certo, Medford, MA (US); Max Echterling, Baltimore, MD (US)

(73) Assignee: 2SEVENTY BIO, INC., Cambridge, MA (US)

( * ) Notice: Subject to any disclaimer, the term of this patent is extended or adjusted under 35 U.S.C. 154(b) by 553 days.

(21) Appl. No.: 16/753,117

(22) PCT Filed: Oct. 4, 2018

(86) PCT No.: PCT/US2018/054365
§ 371 (c)(1),
(2) Date: Apr. 2, 2020

(87) PCT Pub. No.: WO2019/070974
PCT Pub. Date: Apr. 11, 2019

(65) Prior Publication Data
US 2020/0376140 A1 Dec. 3, 2020

Related U.S. Application Data

(60) Provisional application No. 62/671,762, filed on May 15, 2018, provisional application No. 62/568,020, filed on Oct. 4, 2017.

(51) Int. Cl.
| | |
|---|---|
| *A61K 48/00* | (2006.01) |
| *A61P 3/06* | (2006.01) |
| *C12N 9/22* | (2006.01) |
| *C12N 9/64* | (2006.01) |
| *C12N 15/63* | (2006.01) |
| *C12N 15/90* | (2006.01) |

(52) U.S. Cl.
CPC ........ *A61K 48/005* (2013.01); *A61K 48/0041* (2013.01); *A61P 3/06* (2018.01); *C12N 9/22* (2013.01); *C12N 9/6454* (2013.01); *C12N 15/63* (2013.01); *C12N 15/90* (2013.01); *C12Y 304/21061* (2013.01)

(58) Field of Classification Search
None
See application file for complete search history.

(56) References Cited

U.S. PATENT DOCUMENTS

| | | | |
|---|---|---|---|
| 4,751,180 A | 6/1988 | Cousens et al. | |
| 4,873,192 A | 10/1989 | Kunkel | |
| 5,804,413 A | 9/1998 | DeLuca | |
| 5,837,532 A | 11/1998 | Preston et al. | |
| 5,846,782 A | 12/1998 | Wickham et al. | |
| 5,994,136 A | 11/1999 | Naldini et al. | |
| 6,013,516 A | 1/2000 | Verma et al. | |
| 6,682,907 B1 | 1/2004 | Charneau et al. | |
| 8,614,092 B2 | 12/2013 | Zhang et al. | |
| 8,784,799 B2 | 7/2014 | Samulski et al. | |
| 8,809,058 B2 | 8/2014 | Ferrari et al. | |
| 8,889,641 B2 | 11/2014 | Asokan et al. | |
| 9,012,224 B2 | 4/2015 | Bowles et al. | |
| 9,017,967 B2 | 4/2015 | Bonas et al. | |
| 9,169,492 B2 | 10/2015 | Monahan et al. | |
| 9,169,494 B2 | 10/2015 | Hewitt et al. | |
| 2013/0197055 A1* | 8/2013 | Kamens | C12Y 304/21112 435/375 |
| 2013/0337454 A1 | 12/2013 | Duchateau et al. | |
| 2014/0148361 A1* | 5/2014 | Stoddard | C12N 15/1037 506/11 |
| 2016/0002615 A1 | 1/2016 | Smith et al. | |

FOREIGN PATENT DOCUMENTS

| | | | | |
|---|---|---|---|---|
| WO | WO 91/02788 | 3/1991 | | |
| WO | WO 96/04394 | 2/1996 | | |
| WO | WO 98/15637 | 4/1998 | | |
| WO | WO 99/06583 | 2/1999 | | |
| WO | WO 2006/010834 | 2/2006 | | |
| WO | WO 2011/156430 | 12/2011 | | |
| WO | WO 2012/118717 | 9/2012 | | |
| WO | WO 2013/126794 | 8/2013 | | |
| WO | WO-2014191527 A1 * | 12/2014 | ........... A61K 38/465 |
| WO | WO 2017/158422 | 9/2017 | | |
| WO | WO-2017158422 A1 * | 9/2017 | ........... A61K 48/005 |

OTHER PUBLICATIONS

Burke, A.C. et al. 2017; first published online Aug. 8, 2016. PCSK9: Regulation and target for drug development for dyslipidemia. Annual Review of Pharmacology and Toxicology 57: 223-244; specif. pp. 223, 224, 225, 230, 231.*

Schultz, S.C. et al. Site saturation mutagenesis of active site residues of beta-lactamase. In: Proteins; J.J. L'Italien (ed); Plenum Press Copyright 1987; pp. 521-528; specif. p. 521.*

Airaksinen, A. et al. 1998. Modified base compositions at degenerate positions of a mutagenic oligonucleotide enhance randomness in site-saturation mutagenesis. Nucleic Acids Research 26(2): 576-581; specif. p. 576.*

Baxter, S. et al. 2012. Engineering domain fusion chimeras from I-Onul family LAGLIDADG homing endonucleases. Nucleic Acids Research 40(16): 7985-8000 with Supplemental Data; specif. pp. 7985, 7986, 7995 & Supplemental Fig. 1.*

(Continued)

*Primary Examiner* — Renee Claytor
*Assistant Examiner* — Sharon M. Papciak
(74) *Attorney, Agent, or Firm* — Panitch Schwarze Belisario & Nadel LLP; Stephany G. Small; Travis W. Bliss

(57) ABSTRACT

The present disclosure provides improved genome editing compositions and methods for editing a PCSK9 gene. The disclosure further provides genome edited cells for the prevention, treatment, or amelioration of at least one symptom of hypercholesterolemia or a condition associated therewith.

15 Claims, 15 Drawing Sheets

Specification includes a Sequence Listing.

(56) References Cited

OTHER PUBLICATIONS

Wang, Y. et al. 2014. Progressive engineering of a homing endonuclease genome editing reagent for the murine X-linked immunodeficiency locus. Nucleic Acids Research 42(10): 6463-6475; specif. pp. 6463, 6464, 6465, 6470.*
Ashworth et al., "Computational redesign of endonuclease DNA binding and cleavage specificity," Nature. Jun. 1, 2006; 441(7093): 656-659.
Balazs et al., "Liposomes for use in gene delivery," Journal of Drug Delivery 2011, 1-12.
Bennardo et al., "Limiting the Persistence of a Chromosome Break Diminishes Its Mutagenic Potential," PLoS Genetics, Oct. 2009, vol. 5, Issue 10.
Bird, Robert E., et al. "Single-chain antigen-binding proteins." Science (1988); 242.4877: 423-427.
Boissel et al., "megaTALs: a rare-cleaving nuclease architecture for therapeutic genome engineering," Nucleic Acids Research, 2013, 42(4):2591-2601.
Brinkman et al., "Easy quantitative assessment of genome editing by sequence trace decomposition" Nucleic Acids Res. Dec. 16, 2014;42(22).
Certo et al., "Tracking genome engineering outcome at individual DNA breakpoints," Nat Methods. Jul. 10, 2011;8(8):671-6.
Certo et al., "Coupling endonucleases with DNA end-processing enzymes to drive gene disruption" Nat Methods. Oct. 2012; 9(10): 973-975.
Chaudhary, Vuay K., et al. "A rapid method of cloning functional variable-region antibody genes in *Escherichia coli* as single-chain immunotoxins." Proceedings of the National Academy of Sciences (1990); 87.3: 1066-1070 (and correction).
Chevalier et al., "Design, Activity, and Structure of a Highly Specific Artificial Endonuclease," Molecular Cell, vol. 10, 895-905, Oct. 2002.
Clever, J. et al., "RNA Secondary Structure and Binding Sites for gag Gene Products in the 5' Packaging Signal of Human Immunodeficiency Virus Type 1." J. of Virology (1995); 69(4): 2101-2109.
Cullen et al., "Regulatory Pathways Governing HIV-1 Replication", Cell (1989); 58: 423-426.
Cullen, B.R., "Human Immunodeficiency Virus as a Prototypic Complex Retrovirus", Journal of Virology (1991); 65(3): 1053-1056.
Dayhoff et al., (1978) Atlas of Protein Sequence and Structure (Natl. Biomed. Res. Found., Washington, D.C., 8 pages.
De Felipe et al., "Targeting of proteins derived from self-processing polyproteins containing multiple signal sequences." Traffic (2004); 5.8: 616-626.
Desjarlais et al., "Use of a zinc-finger consensus sequence framework and specificity rules to design specific DNA binding proteins." Proceedings of the National Academy of Sciences (1993); 90.6: 2256-2260.
Desjarlais et al., "Length-encoded multiplex binding site determination: application to zinc finger proteins," Proceedings of the National Academy of Sciences (1994); 91.23: 11099-11103.
Donnelly, M. et al., "The 'cleavage' activities of foot-and-mouth disease virus 2A site-directed mutants and naturally occurring '2A-like' sequences." J Gen Virol. (2001); 82 (Pt 5): 1027-1041.
Duke et al., Sequence and structural elements that contribute to efficient encephalomyocarditis virus RNA translation, J Virol. Mar. 1992;66(3):1602-9.
Dull et al., "A third-generation lentivirus vector with a conditional packaging system", Journal of Virology (1998); 72(11): 8463-8671.
Epinat et al., "A novel engineered meganuclease induces homologous recombination in yeast and mammalian cells," 2952-2962 Nucleic Acids Research, 2003, vol. 31, No. 11.
Gomez-Foix et al, "Adenovirus-mediated Transfer of the Muscle Glycogen Phosphorylase Gene into Hepatocytes Confers Altered Regulation of Glycogen Metabolism," J Biol Chem. Dec. 15, 1992;267(35):25129-34.

Graham et al., "Characteristics of a Human Cell Line Transformed by DNA from Human Adenovirus Type 5," J. gen. Virol. 1977, 36, 59-72.
Graham & Preveck, "Chapter 11, Manipulation of Adenovirus Vectors," Methods in Molecular Biology, vol. 7: Gene transfer and Expression Protocols, 1991.
Graham & Preveck, "Adenovirus-Based Expression Vectors and Recombinant Vaccines" Vaccines: New Approaches to Immunological Problems, 1992.
Grunhaus, A., and Horwitz, M. S. "Adenoviruses as cloning vectors," Semin. Virol. 1992; 3, 237-252.
Haas et al., "The Moloney murine leukemia virus repressor binding site represses expression in murine and human hematopoietic stem cells," J Virol. Sep. 2003; 77(17): 9439-9450.
Herz & Gerard, "Adenovirus-mediated transfer of low density lipoprotein receptor gene acutely accelerates cholesterol clearance in normal mice," PNAS, 1993, vol. 90, 2812-2816.
Huang et al., "Role of the hepatitis B virus posttranscriptional regulatory element in export of intronless transcripts," Molecular and Cellular Biology (1995); 15(7): 3864-3869.
Huez et al., "Two independent internal ribosome entry sites are involved in translation initiation of vascular endothelial growth factor mRNA," Mol Cell Biol. Nov. 1998;18(11):6178-90.
International Search Report and Written Opinion dated Dec. 31, 2018, for International Application No. PCT/2018/054365, 10 pages.
Irion, S. et al., "Identification and targeting of the ROSA26 locus in human embryonic stem cells", Nat Biotechnol. (2007); 25(12):1477-1482.
Jackson, et al., "The novel mechanism of initiation of picornavirus RNA translation", Trends Biochem Sci. (1990); 15(12): 477-483.
Jackson, et al., "Internal initiation of translation in eukaryotes: the picornavirus paradigm and beyond", RNA. (1995); 1(10): 985-1000.
Jarjour et al., "High-resolution profiling of homing endonuclease binding and catalytic specificity using yeast surface display," 2009. Nuc. Acids Res. 37(20): 6871-6880.
Jones & Shenk, Isolation of Deletion and Substitution Mutants of Adenovirus Type 5, Cell 1978, vol. 13, 181-188.
Kay et al., "A bacterial effector acts as a plant transcription factor and induces a cell size regulator," Science. Oct. 26, 2007;318(5850):648-51.
Kim, Yang-Gyun, et al. "Hybrid restriction enzymes: zinc finger fusions to Fok I cleavage domain." Proceedings of the National Academy of Sciences (1996); 93.3: 1156-1160.
Kunkel, TA. "Rapid and efficient site-specific mutagenesis without phenotypic selection", Proc Natl Acad Sci U S A. (1985); 82(2): 488-492.
Kunkel, et al "Rapid and efficient site-specific mutagenesis without phenotypic selection", Methods in Enzymol. (1987); 154: 367-382.
Kutner, et al., "Simplified production andconcentration of HIV-1-based lentiviral vectors using HYPERFlask vessels and anion exchange membrane chromatography", BMC Biotechnol. (2009); 9:10. p. 1-7.
Kutner et al., "Production, concentration and titration of pseudotyped HIV-1-based lentiviral vectors", Nature Protocols (2009); 4: 495-505.
Le Gal La Salle et al., "An Adenovirus Vector for Gene Transfer into Neurons and Glia in the Brain," Science Feb. 12, 1993, vol. 259, 988-990.
Levrero et al., "Defective and nondefective adenovirus vectors for expressing foreign genes in vitro and in vivo," Gene 1991; 101:195-202.
Liu et al., "HnRNP L binds a cis-acting RNA sequence element that enables intron-dependent gene expression," Genes & Dev. (1995); 9:1766-1780.
Liu et al., "Design of polydactyl zinc-finger proteins for unique addressing within complex genomes," Proceedings of the National Academy of Sciences (1997); 94.11: 5525-5530.
Liu et al., "Poly(cationic lipid)-mediated in vivo gene delivery to mouse liver," Gene Ther. Jan. 2003;10(2):180-7.
Kurokawa et al., "Adaptation of intronic homing endonuclease for successful horizontal transmission," FEBS Journal 272 (2005) 2487-2496.

(56) References Cited

OTHER PUBLICATIONS

Maratea et al., "Deletion and fusion analysis of the phage phi X174 lysis gene E," Gene. 1985;40(1):39-46.

Murphy et al., "Genetic construction, expression, and melanoma-selective cytotoxicity of a diphtheria toxin-related alpha-melanocyte-stimulating hormone fusion protein," Proc Natl Acad Sci U S A. Nov. 1986;83(21):8258-62.

Naldini L. et al., "Efficient transfer, integration, and sustained long-term expression of the transgene in adult rat brains injected with a lentiviral vector", Proc Natl Acad Sci USA (1996); 93(21): 11382-11388.

Naldini, L. et al., "In vivo gene delivery and stable transduction of nondividing cells by a lentiviral vector", Science (1996); 272(5259): 263-267.

Naldini, L., "Lentiviruses as gene transfer agents for delivery to non-dividing cells", Curr Opin Biotechnol. (1998); 5: 457-463.

Paques et al., "Meganucleases and DNA Double-Strand Break-Induced Recombination: Perspectives for Gene Therapy," Current Gene Therapy, 2007, 7, 49-66.

Pomerantz, et al., "Structure-based design of transcription factors." Science (1995); 267.5194: 93-96.

Pomerantz, et al., "Analysis of homeodomain function by structure-based design of a transcription factor," Proc Natl Acad Sci U S A. Oct. 10, 1995;92(21):9752-6.

Ragot et al., "Efficient adenovirus-mediated transfer of a human minidystrophin gene to skeletal muscle of mdx mice," Nature Feb. 18, 1993; vol. 361: 647-650.

Ryan, M. et al., "Virus-encoded proteinases of the picornavirus super-group." J Gen Virol. (1997); 78 (Pt 4): 699-723.

Rosenfeld et al., "Adenovirus-Mediated Transfer of a Recombinant α1-Antitrypsin Gene to the Lung Epithelium in Vivo," Science Apr. 19, 1991; vol. 252: 431-434.

Rosenfeld et al., "In vivo transfer of the human cystic fibrosis transmembrane conductance regulator gene to the airway epithelium," Cell, Jan. 10, 1992; vol. 68: 143-155.

Sterman et al., "Adenovirus-mediated herpes simplex virus thymidine kinase/ganciclovir gene therapy in patients with localized malignancy: results of a phase I clinical trial in malignant mesothelioma," Hum Gene Ther. May 1, 1998;9(7):1083-92.

Stoddard, "Homing endonuclease structure and function," Quarterly Reviews of Biophysics 2005; 38(1): pp. 49-95.

Stoddard, "Homing Endonucleases: From Microbial Genetic Invaders to Reagents for Targeted DNA Modification," Structure 19, Jan. 12, 2011, 9 pages.

Szymczak, Andrea L., et al. "Correction of multi-gene deficiency in vivo using a single'self-cleaving'2A peptide-based retroviral vector." Nature Biotechnology (2004); 22.5: 589-594.

Takeuchi et al:"Tapping natural reservoirs of homing endonucleases for targeted gene modification", Proceedings of the National Academy of Sciences, National Academy of Sciences, vol. 108, o. 32, Aug. 1, 2011 {Aug. 1, 2011), pp. 13077-13082.

Zennou et al., "HIV-1 genome nuclear import is mediated by a central DNA flap," Cell. Apr. 14, 2000;101(2):173-85.

Zufferey et al., "Multiply attenuated lentiviral vector achieves efficient gene delivery in vivo", Nat Biotechnol. (1997), 15(9): 871-875.

Zufferey, R. et al., "Woodchuck hepatitis virus posttranscriptional regulatory element enhances expression of transgenes delivered by retroviral vectors." J Virol. (1999); 73(4): 2886-2892.

* cited by examiner

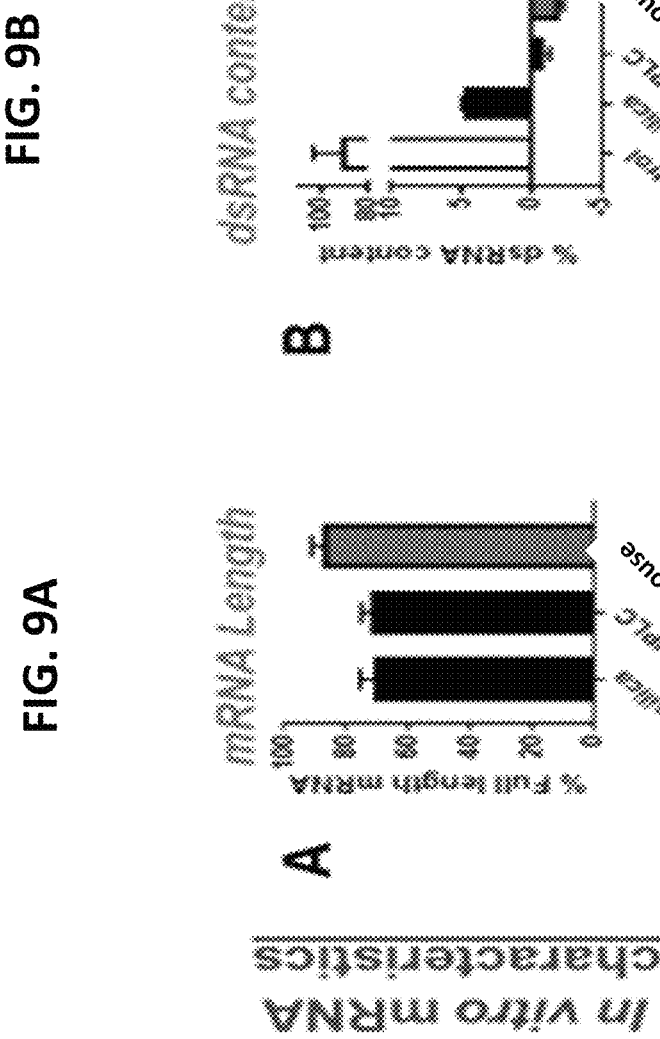

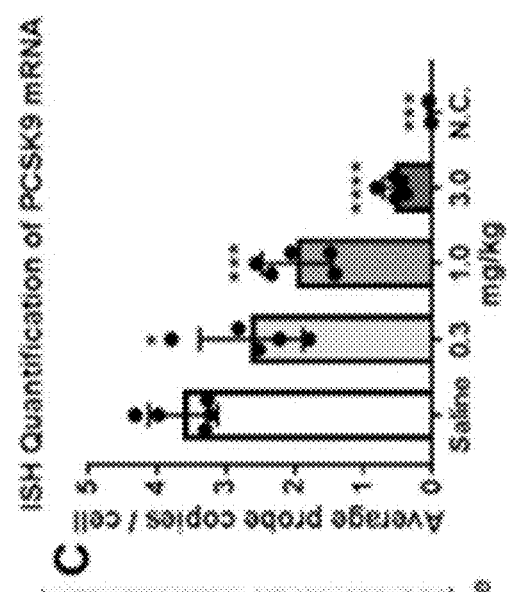
FIG. 11C
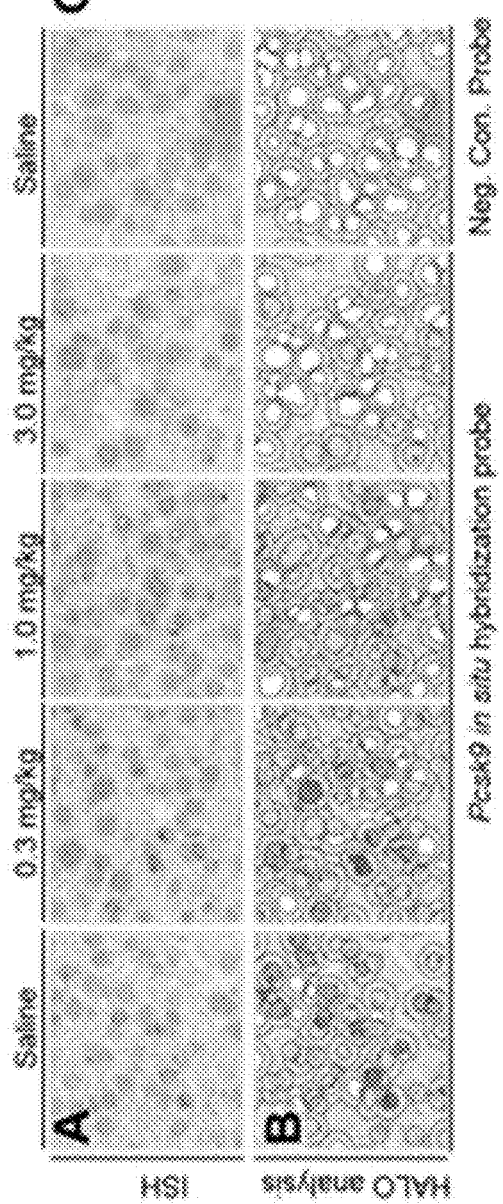
FIG. 11A
FIG. 11B

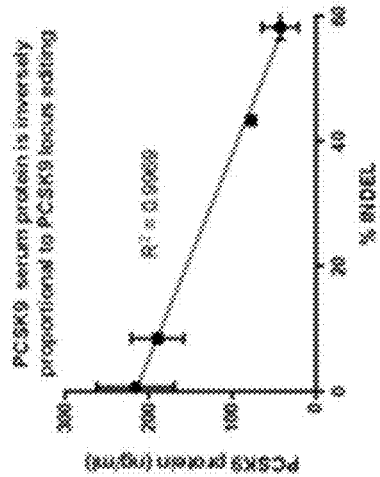
FIG. 11D
FIG. 11E
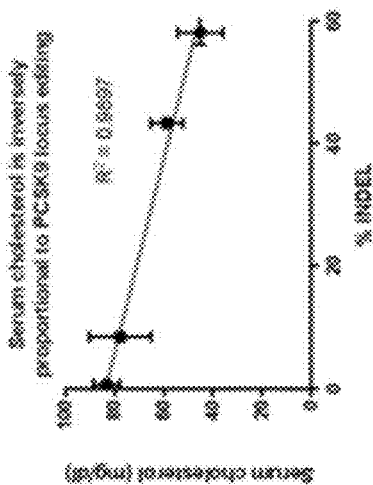
FIG. 11F
FIG. 11G
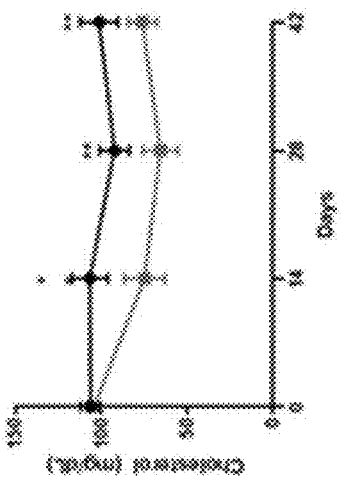
FIG. 11H
FIG. 11I

PCSK9 ENDONUCLEASE VARIANTS, COMPOSITIONS, AND METHODS OF USE

CROSS REFERENCE TO RELATED APPLICATIONS

This application is a National Stage application under 35 U.S.C. § 371 of International Application No. PCT/US2018/054365, filed Oct. 4, 2018, which claims the benefit under 35 U.S.C. § 119(e) of U.S. Provisional Application No. 62/671,762, filed May 15, 2018, and U.S. Provisional Application No. 62/568,020, filed Oct. 4, 2017, each of which is incorporated by reference herein in its entirety.

STATEMENT REGARDING SEQUENCE LISTING

The Sequence Listing associated with this application is provided in text format in lieu of a paper copy, and is hereby incorporated by reference into the specification. The name of the text file containing the Sequence Listing is BLBD_090_02WO_ST25.txt. The text file is 83 KB, was created on Oct. 4, 2018, and is being submitted electronically via EFS-Web, concurrent with the filing of the specification.

BACKGROUND

Technical Field

The present disclosure relates to improved genome editing compositions. More particularly, the disclosure relates to nuclease variants, compositions, and methods of using the same for editing a proprotein convertase subtilisin/kexin type 9 (PCSK9) gene.

Description of the Related Art

Cardiovascular disease is the leading cause of death worldwide. One causal factor in cardiovascular disease is elevated concentration of low-density lipoprotein cholesterol (LDL-C) in the blood. Statins, which reduce LDL-C levels are among the most effective means of reducing the risk of coronary heart disease (CHD). Yet even with the use of statin therapy, there remains a large residual risk of CHD, and a substantial proportion of patients are intolerant of statin therapy.

BRIEF SUMMARY

The present disclosure generally relates, in part, to compositions comprising homing endonuclease variants and megaTALs that cleave a target site in a proprotein convertase subtilisin/kexin type 9 (PCSK9) and methods of using the same.

In various embodiments, a polypeptide comprising a homing endonuclease (HE) variant that cleaves a target site in a proprotein convertase subtilisin/kexin type 9 (PCSK9) gene is contemplated.

In particular embodiments, the HE variant is an LAGLIDADG homing endonuclease (LHE) variant.

In certain embodiments, the polypeptide comprises a biologically active fragment of the HE variant.

In particular embodiments, the biologically active fragment lacks the 1, 2, 3, 4, 5, 6, 7, or 8 N-terminal amino acids compared to a corresponding wild type HE.

In particular embodiments, the biologically active fragment lacks the 4 N-terminal amino acids compared to a corresponding wild type HE.

In some embodiments, the biologically active fragment lacks the 8 N-terminal amino acids compared to a corresponding wild type HE.

In further embodiments, the biologically active fragment lacks the 1, 2, 3, 4, or 5 C-terminal amino acids compared to a corresponding wild type HE.

In various embodiments, the biologically active fragment lacks the C-terminal amino acid compared to a corresponding wild type HE.

In particular embodiments, the biologically active fragment lacks the 2 C-terminal amino acids compared to a corresponding wild type HE.

In certain embodiments, the HE variant is a variant of an LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NerI, I-NcrMI, I-OheMI, I-OnuI, I-OsoMI, I-OsoMII, I-OsoMIII, I-OsoMIV, I-PanNI, I-PanII, I-PanMIII, I-PnoMI, I-ScuMI, I-SmaMI, I-SscMI, and I-Vdi141I.

In further embodiments, the HE variant is a variant of an LHE selected from the group consisting of I-CpaMI, I-HjeMI, I-OnuI, I-PanII, and SmaMI.

In particular embodiments, the HE variant is an I-OnuI LHE variant.

In some embodiments, the HE variant comprises one or more amino acid substitutions in the DNA recognition interface at amino acid positions selected from the group consisting of 24, 26, 28, 30, 32, 34, 35, 36, 37, 38, 40, 42, 44, 46, 48, 68, 70, 72, 75, 76, 78, 80, 82, 180, 182, 184, 186, 188, 189, 190, 191, 192, 193, 195, 197, 199, 201, 203, 223, 225, 227, 229, 231, 232, 234, 236, 238, and 240 of an I-OnuI LHE amino acid sequence asset forth in SEQ ID NOs: 1-5, or a biologically active fragment thereof.

In particular embodiments, the HE variant comprises at least 5, at least 15, preferably at least 25, more preferably at least 35, or even more preferably at least 40 or more amino acid substitutions in the DNA recognition interface at amino acid positions selected from the group consisting of 24, 26, 28, 30, 32, 34, 35, 36, 37, 38, 40, 42, 44, 46, 48, 68, 70, 72, 75, 76, 78, 80, 82, 180, 182, 184, 186, 188, 189, 190, 191, 192, 193, 195, 197, 199, 201, 203, 223, 225, 227, 229, 231, 232, 234, 236, 238, and 240 of an I-OnuI LHE amino acid sequence as set forth in SEQ ID NOs: 1-5, or a biologically active fragment thereof.

In some embodiments, the HE variant comprises one or more amino acid substitutions at amino acid positions selected from the group consisting of: 24, 26, 28, 30, 32, 34, 35, 36, 37, 38, 40, 42, 44, 46, 48, 61, 68, 70, 72, 75, 76, 78, 80, 82, 116, 138, 143, 159, 168, 178, 180, 182, 184, 188, 189, 190, 191, 192, 193, 195, 197, 199, 203, 207, 223, 225, 227, 232, and 236 of an I-OnuI LHE amino acid sequence as set forth in SEQ ID NOs: 1-5, or a biologically active fragment thereof.

In various embodiments, the HE variant cleaves a PCSK9 target site and comprises at least 5, at least 15, preferably at least 25, more preferably at least 35, or even more preferably at least 40 or more amino acid substitutions in at least one position selected from the position group consisting of positions: 24, 26, 28, 30, 32, 34, 35, 36, 37, 38, 40, 42, 44, 46, 48, 61, 68, 70, 72, 75, 76, 78, 80, 82, 116, 138, 143, 159, 168, 178, 180, 182, 184, 188, 189, 190, 191, 192, 193, 195, 197, 199, 203, 207, 223, 225, 227, 232, and 236 of any one of SEQ ID NOs: 1-5, or a biologically active fragment thereof.

In certain embodiments, the HE variant cleaves a PCSK9 target site and comprises at least 5, at least 15, preferably at least 25, more preferably at least 35, or even more preferably at least 40 or more of the following amino acid substitutions: S24C, L26M, R28N, R30W, N32K, K34R, S35T, S36R, V37A, G38K, S40Y, E42A, G44R, Q46E, T48A, Q61R, V68K, A70R, S72I, N75R, A76V, S78K, K80V, T82G, V116L, L138M, T143N, S159P, F168L, E178D, C180Y, F182G, N184E, I186M, S188R, K189T, S190T, K191G, L192T, G193H, Q195T, Q197R, V199R, T203A, K207R, Y223R, K225S, K227R, F232Y, and D236E of any one of SEQ ID NOs: 1-5, or a biologically active fragment thereof.

In particular embodiments, the HE variant cleaves a PCSK9 target site and comprises at least 5, at least 15, preferably at least 25, more preferably at least 35, or even more preferably at least 40 or more of the following amino acid substitutions: S24C, L26M, R28N, R30W, N32K, K34R, S35T, S36R, V37A, G38K, S40Y, E42A, G44R, Q46E, T48A, Q61R, V68K, A70R, S72I, N75R, A76V, S78K, K80V, T82G, V116L, L138M, T143N, S159P, F168L, E178D, C180Y, F182G, N184E, I186M, S188R, S190T, K191G, L192T, G193H, Q195T, Q197R, V199R, T203A, K207R, Y223R, K225S, K227R, F232Y, and D236E of any one of SEQ ID NOs: 1-5, or a biologically active fragment thereof.

In various embodiments, the HE variant cleaves a PCSK9 target site and comprises at least 5, at least 15, preferably at least 25, more preferably at least 35, or even more preferably at least 40 or more of the following amino acid substitutions: S24C, L26M, R28N, R30W, N32K, K34R, S35T, S36R, V37A, G38K, S40Y, E42A, G44R, Q46E, T48A, Q61R, V68K, A70R, S72I, N75R, A76V, S78K, K80V, T82G, V116L, L138M, T143N, S159P, F168L, E178D, C180Y, F182G, N184E, I186M, S188R, K189T, S190T, K191G, L192T, G193H, Q195T, Q197R, V199R, K207R, Y223R, K225S, K227R, F232Y, and D236E of any one of SEQ ID NOs: 1-5, or a biologically active fragment thereof.

In various embodiments, the HE variant comprises an amino acid sequence that is at least 80%, preferably at least 85%, more preferably at least 90%, or even more preferably at least 95% identical to the amino acid sequence set forth in any one of SEQ ID NOs: 6-7, or a biologically active fragment thereof.

In further embodiments, the HE variant comprises the amino acid sequence set forth in SEQ ID NO: 6, or a biologically active fragment thereof.

In certain embodiments, the HE variant comprises the amino acid sequence set forth in SEQ ID NO: 7, or a biologically active fragment thereof.

In particular embodiments, the polypeptide binds the polynucleotide sequence set forth in SEQ ID NO: 11.

In particular embodiments, the polypeptide further comprises a DNA binding domain.

In some embodiments, the DNA binding domain is selected from the group consisting of: a TALE DNA binding domain and a zinc finger DNA binding domain.

In various embodiments, the TALE DNA binding domain comprises about 9.5 TALE repeat units to about 15.5 TALE repeat units.

In certain embodiments, the TALE DNA binding domain binds a polynucleotide sequence in the PCSK9 gene.

In further embodiments, the TALE DNA binding domain binds the polynucleotide sequence set forth in SEQ ID NO: 13.

In various embodiments, the polypeptide binds and cleaves the polynucleotide sequence set forth in SEQ ID NO: 14.

In particular embodiments, the zinc finger DNA binding domain comprises 2, 3, 4, 5, 6, 7, or 8 zinc finger motifs.

In certain embodiments, the polypeptide further comprises a peptide linker and an end-processing enzyme or biologically active fragment thereof.

In some embodiments, the polypeptide further comprises a viral self-cleaving 2A peptide and an end-processing enzyme or biologically active fragment thereof.

In particular embodiments, the end-processing enzyme or biologically active fragment thereof has 5'-3' exonuclease, 5'-3' alkaline exonuclease, 3'-5' exonuclease, 5' flap endonuclease, helicase or template-independent DNA polymerase activity.

In certain embodiments, the end-processing enzyme comprises Trex2 or a biologically active fragment thereof.

In various embodiments, the polypeptide comprises the amino acid sequence set forth in SEQ ID NO: 8 or SEQ ID NO: 9, or a biologically active fragment thereof.

In some embodiments, the polypeptide comprises the amino acid sequence set forth in SEQ ID NO: 8, or a biologically active fragment thereof.

In certain embodiments, the polypeptide comprises the amino acid sequence set forth in SEQ ID NO: 9, or a biologically active fragment thereof.

In particular embodiments, the polypeptide cleaves the mouse PCSK9 gene at a polynucleotide sequence set forth in SEQ ID NO: 11.

In particular embodiments, the polypeptide cleaves the mouse PCSK9 gene at a polynucleotide sequence set forth in SEQ ID NO: 13.

In various embodiments, a polynucleotide encoding a polypeptide contemplated herein is provided.

In some embodiments, an mRNA encoding a polypeptide contemplated herein is provided.

In particular embodiments, the mRNA further comprises a 5'cap and a poly(A) tail.

In further embodiments, the mRNA comprises one or more modified ribonucleotides.

In certain embodiments, a cDNA encoding a polypeptide contemplated herein is provided.

In particular embodiments, a lipid nanoparticle comprising an mRNA encoding a polypeptide contemplated herein (e.g, PPCSK9 HE or megaTAL) and an mRNA encoding Trex2 is provided.

In some embodiments, a vector comprises a polynucleotide encoding a polypeptide contemplated herein.

In particular embodiments, a cell comprising a polypeptide contemplated herein is provided.

In various embodiments, a cell comprises a polynucleotide encoding a polypeptide contemplated herein.

In certain embodiments, a cell comprising an mRNA contemplated herein is provided.

In some embodiments, cell comprises a cDNA contemplated herein.

In particular embodiments, a cell comprising a vector contemplated herein is provided.

In further embodiments, a cell comprises one or more genome modifications introduced by a polypeptide contemplated herein.

In various embodiments, the one or more genome modifications comprise an insertion or deletion of one or more nucleotides at the site of the DSB introduced by a polypeptide contemplated herein.

In further embodiments, the cell comprises a polynucleotide encoding a therapeutic protein introduced at the site of the DSB by homology directed repair.

In some embodiments, the polynucleotide encoding the therapeutic protein further comprises an RNA polymerase II promoter operably linked to the polynucleotide sequence encoding the therapeutic protein.

In particular embodiments, the RNA polymerase II promoter is selected from the group consisting of: a short EF1α promoter, a long EF1α promoter, a human ROSA 26 locus, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted U3 (MNDU3) promoter.

In various embodiments, the polynucleotide encoding the therapeutic protein further comprises a heterologous polyadenylation signal.

In various embodiments, the cell is a stem cell.

In some embodiments, the cell is a liver cell or hepatic cell.

In particular embodiments, the cell is a hepatocyte.

In certain embodiments, the cell is a stellate cell.

In particular embodiments, the cell is a Kupffer cell.

In certain embodiments, the cell is a liver endothelial cell.

In particular embodiments, the cell comprises one or more modified PCSK9 alleles.

In various embodiments, the one or more modified PCSK9 alleles are non-functional and/or have substantially reduced PCSK9 expression and/or function.

In further embodiments, a plurality of cells comprises one or more cells contemplated herein.

In some embodiments, a composition comprises one or more cells contemplated herein.

In various embodiments, composition comprises a polynucleotide that encodes a polypeptide, an mRNA, a cDNA, or a vector contemplated herein.

In some embodiments, a composition comprises one or more cells contemplated herein and a physiologically acceptable carrier.

In certain embodiments, a composition comprises a physiologically acceptable carrier and a polynucleotide that encodes a polypeptide, an mRNA, a cDNA, or a vector contemplated herein.

In particular embodiments, a composition comprises a lipid nanoparticle comprising an mRNA encoding a polypeptide contemplated herein (e.g, PPCSK9 HE or megaTAL) and an mRNA encoding Trex2.

In preferred embodiments, a composition comprises a lipid nanoparticle formulated with a PCSK9 megaTAL mRNA and a Trex2 mRNA.

In further embodiments, a method of editing a human PCSK9 gene in a cell comprises introducing a polynucleotide encoding a polypeptide contemplated herein into the cell, wherein expression of the polypeptide creates a double strand break at a target site in a human PCSK9 gene.

In particular embodiments, a method of editing a human PCSK9 gene in a cell comprises introducing a polynucleotide encoding a polypeptide contemplated herein into the cell, wherein expression of the polypeptide creates a double strand break at a target site in a human PCSK9 gene, wherein the break is repaired by non-homologous end joining (NHEJ).

In some embodiments, a method of editing a human PCSK9 gene in a cell comprises introducing a polynucleotide encoding a polypeptide contemplated herein and a donor repair template into the cell, wherein expression of the polypeptide creates a double strand break at a target site in a human PCSK9 gene and the donor repair template is incorporated into the human PCSK9 gene by homology directed repair (HDR) at the site of the double-strand break (DSB).

In various embodiments, the donor repair template encodes a therapeutic protein.

In particular embodiments, the donor repair template further comprises an RNA polymerase II promoter operably linked to the polynucleotide sequence encoding the therapeutic protein.

In certain embodiments, the RNA polymerase II promoter is selected from the group consisting of: a short EF1α promoter, a long EF1α promoter, a human ROSA 26 locus, a Ubiquitin C (UBC) promoter, a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted U3 (MNDU3) promoter.

In some embodiments, the donor repair template further comprises a heterologous polyadenylation signal.

In particular embodiments, a viral vector is used to introduce the donor repair template into the cell.

In certain embodiments, the viral vector is a recombinant adeno-associated viral vector (rAAV) or a retrovirus.

In various embodiments, the rAAV has one or more ITRs from AAV2.

In particular embodiments, the rAAV has a serotype selected from the group consisting of AAV1, AAV2, AAV3, AAV4, AAV5, AAV6, AAV7, AAV8, AAV9, and AAV10.

In some embodiments, the rAAV has an AAV2 or AAV8 serotype.

In various embodiments, the cell is a liver cell.

In some embodiments, a method of editing a human PCSK9 gene in a liver cell of a subject, comprises administering to the liver of the subject, an effective amount of a polynucleotide encoding a polypeptide, an mRNA, or a vector encoding the same contemplated herein, wherein expression of the polypeptide creates a double strand break at a target site in the human PCSK9 gene.

In certain embodiments, a method of editing a human PCSK9 gene in a liver cell of a subject, comprises administering to the liver of the subject, an effective amount of a polynucleotide encoding a polypeptide, an mRNA, or a vector encoding the same contemplated herein, wherein the break is repaired by non-homologous end joining (NHEJ).

In particular embodiments, a method of editing a human PCSK9 gene in a liver cell of a subject, comprises administering to the liver of the subject, an effective amount of a donor repair template and a polynucleotide encoding the polypeptide, an mRNA, or a vector encoding the same contemplated herein, wherein expression of the polypeptide creates a double strand break at a target site in a human PCSK9 gene and the donor repair template is incorporated into the human PCSK9 gene by homology directed repair (HDR) at the site of the double-strand break (DSB).

In various embodiments, method of treating, preventing, or ameliorating at least one symptom of a hypercholesterolemia, or condition associated therewith, comprises administering to the subject an effective amount of a composition contemplated herein.

In certain embodiments, the method further comprises administering a donor repair template to the subject.

In particular embodiments, the composition and donor repair template are administered to the liver of the subject.

In certain embodiments, the method further comprises introducing an end-processing enzyme or biologically active fragment thereof.

In particular embodiments, the end-processing enzyme or biologically active fragment thereof has 5'-3' exonuclease, 5'-3' alkaline exonuclease, 3'-5' exonuclease, 5' flap endonuclease, helicase or template-independent DNA polymerase activity.

In various embodiments, the end-processing enzyme comprises Trex2 or a biologically active fragment thereof.

In preferred embodiments, PCSK9 megaTAL mRNA is formulated with Trex2 mRNA in a lipid nanoparticle.

BRIEF DESCRIPTION OF SEVERAL VIEWS OF THE DRAWINGS

FIGS. 9A-FIG. 9F show in vitro and in vivo comparisons among PCSK9 megaTAL and Trex2 mRNA purified by silica resin, HPLC, or an in-house method that isolates polyA mRNA and decreases dsRNA. FIG. 9A shows % full length transcripts.

FIG. 9B shows % double-stranded RNA content. FIG. 9C shows in vitro toxicity. FIG. 9D shows in vivo editing as a function of % INDEL. FIG. 9E shows in vivo toxicity.

FIG. 9F shows in vivo immunogenicity.

FIGS. 11A-11I show the effects of PCSK9 editing on PCSK9 expression and serum cholesterol levels in the mice treated in Example 7. FIG. 11A shows in situ hybridization of PCSK9 transcript in fixed liver sections, 96 hours post-administration. FIG. 11B shows an automatic-quantification of the in situ hybridization using HALO software. FIG. 11C shows a graphical representation of the HALO quantification. FIG. 11D shows a dose dependent decrease in circulating PCSK9 serum protein measured by ELISA. FIG. 11E shows that decreased PCSK9 in serum correlates with increased PCSK9 gene editing. FIG. 11F shows a dose dependent decrease in serum cholesterol. FIG. 11G shows that decreased serum cholesterol correlates with increased PCSK9 gene editing. FIG. 11H shows that mice treated with 1 mg/kg of PCSK9 megaTAL and Trex2 mRNA showed sustained and significant reductions in serum PCSK9 protein. FIG. 11I shows that mice treated with 1 mg/kg of PCSK9 megaTAL and Trex2 mRNA showed sustained and significant reductions in serum cholesterol. *=p≤0.05, =p≤0.01, *=p≤0.001, n.s. (not significant)=p>0.05 (student t-test).

FIG. 12A shows that PCSK9 megaTAL and Trex2 mRNA/LNP formulations are well tolerated and resulted in only two-fold increases in transaminase levels at 24 hours post administration at lower doses, and ultimately resolved to base line levels by 96 hours for all doses. FIG. 12B shows that liver function is normal after treatment with PCSK9 megaTAL and Trex2 mRNA/LNP formulations at all doses as assessed by unchanged serum albumin levels 96 hours after mRNA/LNP administration.

FIG. 12C shows that PCSK9 megaTAL mRNA is transiently expressed as mRNA message levels in mice treated with 1 mg/kg of mRNA decrease from 4 to 96 hours post-administration.

BRIEF DESCRIPTION OF THE SEQUENCE IDENTIFIERS

Figure 1:
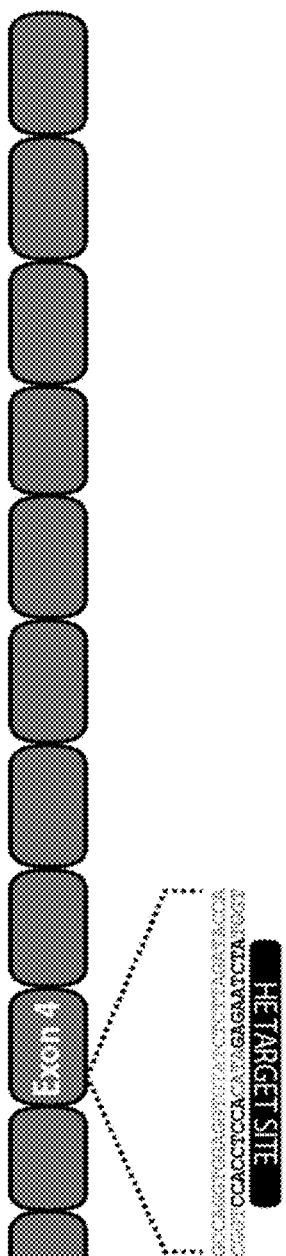
FIG. 1 shows a schematic of a PCSK9 gene and the HE target site in exon 4 (SEQ ID NOS: 61 and 62).

SEQ ID NO: 1 is an amino acid sequence of a wild type I-OnuI LAGLIDADG homing endonuclease (LHE).

SEQ ID NO: 2 is an amino acid sequence of a wild type I-OnuI LHE.

SEQ ID NO: 3 is an amino acid sequence of a biologically active fragment of a wild-type I-OnuI LHE.

SEQ ID NO: 4 is an amino acid sequence of a biologically active fragment of a wild-type I-OnuI LHE.

SEQ ID NO: 5 is an amino acid sequence of a biologically active fragment of a wild-type I-OnuI LHE.

SEQ ID NO: 6 is an amino acid sequence of an I-OnuI LHE variant reprogrammed to bind and cleave a target site in a PCSK9 gene.

SEQ ID NO: 7 is an amino acid sequence of an I-OnuI LHE variant reprogrammed to bind and cleave a target site in a PCSK9 gene.

SEQ ID NO: 8 is an amino acid sequence of a megaTAL that binds and cleaves a target site in a PCSK9 gene.

SEQ ID NO: 9 is an amino acid sequence of a megaTAL that binds and cleaves a target site in a PCSK9 gene.

SEQ ID NO: 10 is an amino acid sequence of a megaTAL that binds and cleaves a target site in a PCSK9 gene fused to murine Trex2.

SEQ ID NO: 11 is an I-OnuI LHE variant target site in exon 4 of a PCSK9 gene.

SEQ ID NO: 12 is a TALE DNA binding domain target site in exon 4 of a PCSK9 gene.

SEQ ID NO: 13 is a megaTAL target site in exon 4 of a PCSK9 gene.

SEQ ID NO: 14 is an I-OnuI LHE variant N-terminal domain target site in exon 4 of a PCSK9 gene.

SEQ ID NO: 15 is an I-OnuI LHE variant N-terminal domain target site in exon 4 of a PCSK9 gene.

SEQ ID NO: 16 is an I-OnuI LHE variant C-terminal domain target site in exon 4 of a PCSK9 gene.

SEQ ID NO: 17 is an I-OnuI LHE variant C-terminal domain target site in exon 4 of a PCSK9 gene.

SEQ ID NO: 18 is an I-OnuI LHE variant C-terminal domain target site in exon 4 of a PCSK9 gene.

SEQ ID NO: 19 is an I-OnuI LHE variant C-terminal domain target site in exon 4 of a PCSK9 gene.

SEQ ID NO: 20 is a polynucleotide sequence of a PCSK9.H7.C11 surface display plasmid.

SEQ ID NO: 21 is an mRNA sequence encoding a PCSK9.H7.C11 megaTAL.

SEQ ID NO: 22 is an mRNA sequence encoding murine Trex2.

SEQ ID NO: 23 is an amino acid sequence encoding murine Trex2.

SEQ ID NOs: 24-34 set forth the amino acid sequences of various linkers.

SEQ ID NOs: 35-59 set forth the amino acid sequences of protease cleavage sites and self-cleaving polypeptide cleavage sites.

In the foregoing sequences, X, if present, refers to any amino acid or the absence of an amino acid.

DETAILED DESCRIPTION

A. Overview

The present disclosure generally relates to, in part, improved genome editing compositions and methods of use thereof. Without wishing to be bound by any particular theory, genome editing compositions contemplated in various embodiments can be used to prevent or treat hypercholesterolemia, or condition associated therewith, or ameliorates at least one symptom thereof.

Proprotein convertase subtilisin/kexin type 9 (PCSK9) is expressed in and secreted from the liver, and believed to function primarily as an antagonist to the LDL receptor (LDLR). PCSK9 was originally identified as the cause of autosomal dominant hypercholesterolemia in some families, with gain-of-function mutations in the gene driving highly elevated LDL-C levels and premature CHD. In subsequent studies, individuals with single loss-of-function mutations in PCSK9 were found to experience a significant reduction of both LDL-C levels (~30%-40%) as well as CHD risk (88%). Notably, even individuals with two loss-of-function mutations in PCSK9—resulting in ~80% reduction in LDL-C levels—appear to suffer no adverse clinical consequences.

Genome editing compositions and methods contemplated in various embodiments comprise nuclease variants, designed to bind and cleave a target site in a proprotein convertase subtilisin/kexin type 9 (PCSK9) gene. In particular compositions genome editing compositions contemplated herein comprise a polynucleotide encoding a nuclease variant or megaTAL that binds and cleaves a target site in a PCSK9 gene. The nuclease variants contemplated in particular embodiments, can be used to introduce a double-strand break in a target polynucleotide sequence, which may be repaired by non-homologous end joining (NHEJ) in the absence of a polynucleotide template, e.g., a donor repair template, or by homology directed repair (HDR), i.e., homologous recombination, in the presence of a donor repair template. Nuclease variants contemplated in certain embodiments, can also be designed as nickases, which generate single-stranded DNA breaks that can be repaired using the cell's base-excision-repair (BER) machinery or homologous recombination in the presence of a donor repair template. NHEJ is an error-prone process that frequently results in the formation of small insertions and deletions that disrupt gene function. Homologous recombination requires homologous DNA as a template for repair and can be leveraged to create a limitless variety of modifications specified by the introduction of donor DNA containing the desired sequence at the target site, flanked on either side by sequences bearing homology to regions flanking the target site.

In one preferred embodiment, the genome editing compositions contemplated herein comprise a polynucleotide encoding a homing endonuclease variant or megaTAL that targets a PCSK9 gene.

In one preferred embodiment, the genome editing compositions contemplated herein comprise one or more polynucleotides encoding a homing endonuclease variant or megaTAL and an end-processing enzyme, e.g., Trex2.

Techniques for recombinant (i.e., engineered) DNA, peptide and oligonucleotide synthesis, immunoassays, tissue culture, transformation (e.g., electroporation, lipofection), enzymatic reactions, purification and related techniques and procedures may be generally performed as described in various general and more specific references in microbiology, molecular biology, biochemistry, molecular genetics, cell biology, virology and immunology as cited and discussed throughout the present specification. See, e.g., Sambrook et al., *Molecular Cloning: A Laboratory Manual*, 3d ed., Cold Spring Harbor Laboratory Press, Cold Spring Harbor, N.Y.; *Current Protocols in Molecular Biology* (John Wiley and Sons, updated July 2008); *Short Protocols in Molecular Biology: A Compendium of Methods from Current Protocols in Molecular Biology*, Greene Pub. Associates and Wiley-Interscience; Glover, *DNA Cloning: A Practical Approach*, vol. I & II (IRL Press, Oxford Univ. Press USA, 1985); *Current Protocols in Immunology* (Edited by: John E. Coligan, Ada M. Kruisbeek, David H. Margulies, Ethan M. Shevach, Warren Strober 2001 John Wiley & Sons, NY, NY); *Real-Time PCR: Current Technology and Applications*, Edited by Julie Logan, Kirstin Edwards and Nick Saunders, 2009, Caister Academic Press, Norfolk, UK; Anand, *Techniques for the Analysis of Complex Genomes*, (Academic Press, New York, 1992); Guthrie and Fink, *Guide to Yeast Genetics and Molecular Biology* (Academic Press, New York, 1991); Oligonucleotide Synthesis (N. Gait, Ed., 1984); Nucleic Acid The *Hybridization* (B. Hames & S. Higgins, Eds., 1985); *Transcription and Translation* (B. Hames & S. Higgins, Eds., 1984); Animal Cell Culture (R. Freshney, Ed., 1986); Perbal, *A Practical Guide to Molecular Cloning* (1984); *Next-Generation Genome Sequencing* (Janitz, 2008 Wiley-VCH); PCR Protocols (*Methods in Molecular Biology*) (Park, Ed., 3rd Edition, 2010 Humana Press); *Immobilized Cells And Enzymes* (IRL Press, 1986); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); Harlow and Lane, *Antibodies*, (Cold Spring Harbor Laboratory Press, Cold Spring Harbor, N.Y., 1998); *Immunochemical Methods In Cell And Molecular Biology* (Mayer and Walker, eds., Academic Press, London, 1987); *Handbook Of Experimental Immunology*, Volumes I-IV (D. M. Weir and CC Blackwell, eds., 1986); Roitt, *Essential Immunology*, 6th Edition, (Blackwell Scientific Publications, Oxford, 1988); *Current Protocols in Immunology* (Q. E. Coligan, A. M. Kruisbeek, D. H. Margulies, E. M.

Shevach and W. Strober, eds., 1991); *Annual Review of Immunology*; as well as monographs in journals such as *Advances in Immunology*.

B. Definitions

Prior to setting forth this disclosure in more detail, it may be helpful to an understanding thereof to provide definitions of certain terms to be used herein.

Unless defined otherwise, all technical and scientific terms used herein have the same meaning as commonly understood by those of ordinary skill in the art to which the invention belongs. Although any methods and materials similar or equivalent to those described herein can be used in the practice or testing of particular embodiments, preferred embodiments of compositions, methods and materials are described herein. For the purposes of the present disclosure, the following terms are defined below. Additional definitions are set forth throughout this disclosure.

The articles "a," "an," and "the" are used herein to refer to one or to more than one (i.e., to at least one, or to one or more) of the grammatical object of the article. By way of example, "an element" means one element or one or more elements.

The use of the alternative (e.g., "or") should be understood to mean either one, both, or any combination thereof of the alternatives.

The term "and/or" should be understood to mean either one, or both of the alternatives.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length ±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

In one embodiment, a range, e.g., 1 to 5, about 1 to 5, or about 1 to about 5, refers to each numerical value encompassed by the range. For example, in one non-limiting and merely illustrative embodiment, the range "1 to 5" is equivalent to the expression 1, 2, 3, 4, 5; or 1.0, 1.5, 2.0, 2.5, 3.0, 3.5, 4.0, 4.5, or 5.0; or 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, or 5.0.

As used herein, the term "substantially" refers to a quantity, level, value, number, frequency, percentage, dimension, size, amount, weight or length that is 80%, 85%, 90%, 91%, 92%, 93%, 94%, 95%, 96%, 97%, 98%, 99% or higher compared to a reference quantity, level, value, number, frequency, percentage, dimension, size, amount, weight or length. In one embodiment, "substantially the same" refers to a quantity, level, value, number, frequency, percentage, dimension, size, amount, weight or length that produces an effect, e.g., a physiological effect, that is approximately the same as a reference quantity, level, value, number, frequency, percentage, dimension, size, amount, weight or length.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are present that materially affect the activity or action of the listed elements.

Reference throughout this specification to "one embodiment," "an embodiment," "a particular embodiment," "a related embodiment," "a certain embodiment," "an additional embodiment," or "a further embodiment" or combinations thereof means that a particular feature, structure or characteristic described in connection with the embodiment is included in at least one embodiment. Thus, the appearances of the foregoing phrases in various places throughout this specification are not necessarily all referring to the same embodiment. Furthermore, the particular features, structures, or characteristics may be combined in any suitable manner in one or more embodiments. It is also understood that the positive recitation of a feature in one embodiment, serves as a basis for excluding the feature in a particular embodiment.

The term "ex vivo" refers generally to activities that take place outside an organism, such as experimentation or measurements done in or on living tissue in an artificial environment outside the organism, preferably with minimum alteration of the natural conditions. In particular embodiments, "ex vivo" procedures involve living cells or tissues taken from an organism and cultured or modulated in a laboratory apparatus, usually under sterile conditions, and typically for a few hours or up to about 24 hours, but including up to 48 or 72 hours, depending on the circumstances. In certain embodiments, such tissues or cells can be collected and frozen, and later thawed for ex vivo treatment. Tissue culture experiments or procedures lasting longer than a few days using living cells or tissue are typically considered to be "in vitro," though in certain embodiments, this term can be used interchangeably with ex vivo.

The term "in vivo" refers generally to activities that take place inside an organism. In one embodiment, cellular genomes are engineered, edited, or modified in vivo.

By "enhance" or "promote" or "increase" or "expand" or "potentiate" refers generally to the ability of a nuclease variant, genome editing composition, or genome edited cell contemplated herein to produce, elicit, or cause a greater response (i.e., physiological response) compared to the response caused by either vehicle or control. A measurable response may include an increase in catalytic activity, binding affinity, binding site specificity, binding site selectivity, among others apparent from the understanding in the art and the description herein. An "increased" or "enhanced" amount is typically a "statistically significant" amount, and may include an increase that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response produced by vehicle or control.

By "decrease" or "lower" or "lessen" or "reduce" or "abate" or "ablate" or "inhibit" or "dampen" refers generally to the ability of a nuclease variant, genome editing composition, or genome edited cell contemplated herein to produce, elicit, or cause a lesser response (i.e., physiological response) compared to the response caused by either vehicle or control. A measurable response may include a decrease in off-target binding affinity, off-target cleavage specificity, decreased cholesterol levels, and the like. A "decrease" or "reduced" amount is typically a "statistically significant" amount, and may include an decrease that is 1.1, 1.2, 1.5, 2, 3, 4, 5, 6, 7, 8, 9, 10, 15, 20, 30 or more times (e.g., 500, 1000 times) (including all integers and decimal points in between and above 1, e.g., 1.5, 1.6, 1.7. 1.8, etc.) the response (reference response) produced by vehicle, or control.

By "maintain," or "preserve," or "maintenance," or "no change," or "no substantial change," or "no substantial decrease" refers generally to the ability of a nuclease variant, genome editing composition, or genome edited cell contemplated herein to produce, elicit, or cause a substantially similar or comparable physiological response (i.e., downstream effects) in as compared to the response caused by either vehicle or control. A comparable response is one that is not significantly different or measurable different from the reference response.

The terms "specific binding affinity" or "specifically binds" or "specifically bound" or "specific binding" or "specifically targets" as used herein, describe binding of one molecule to another, e.g., DNA binding domain of a polypeptide binding to DNA, at greater binding affinity than background binding. A binding domain "specifically binds" to a target site if it binds to or associates with a target site with an affinity or $K_a$ (i.e., an equilibrium association constant of a particular binding interaction with units of 1/M) of, for example, greater than or equal to about $10^5$ $M^{-1}$. In certain embodiments, a binding domain binds to a target site with a $K_a$ greater than or equal to about $10^6$ $M^{-1}$, $10^7$ $M^{-1}$, $10^1$ $M^{-1}$, $10^9$ $M^{-1}$, $10^{10}$ $M^{-1}$, $10 M^{-1}$, $10^{12} M^{-1}$, or $10^{13}$ $M^{-1}$. "High affinity" binding domains refers to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, at least $10^{13}$ $M^{-1}$, or greater.

Alternatively, affinity may be defined as an equilibrium dissociation constant ($K_d$) of a particular binding interaction with units of M (e.g., $10^{-5}$ M to $10^{-13}$ M, or less). Affinities of nuclease variants comprising one or more DNA binding domains for DNA target sites contemplated in particular embodiments can be readily determined using conventional techniques, e.g., yeast cell surface display, or by binding association, or displacement assays using labeled ligands.

In one embodiment, the affinity of specific binding is about 2 times greater than background binding, about 5 times greater than background binding, about 10 times greater than background binding, about 20 times greater than background binding, about 50 times greater than background binding, about 100 times greater than background binding, or about 1000 times greater than background binding or more.

The terms "selectively binds" or "selectively bound" or "selectively binding" or "selectively targets" and describe preferential binding of one molecule to a target molecule (on-target binding) in the presence of a plurality of off-target molecules. In particular embodiments, an HE or megaTAL selectively binds an on-target DNA binding site about 5, 10, 15, 20, 25, 50, 100, or 1000 times more frequently than the HE or megaTAL binds an off-target DNA target binding site.

"On-target" refers to a target site sequence.

"Off-target" refers to a sequence similar to but not identical to a target site sequence.

A "target site" or "target sequence" is a chromosomal or extrachromosomal nucleic acid sequence that defines a portion of a nucleic acid to which a binding molecule will bind and/or cleave, provided sufficient conditions for binding and/or cleavage exist. When referring to a polynucleotide sequence or SEQ ID NO. that references only one strand of a target site or target sequence, it would be understood that the target site or target sequence bound and/or cleaved by a nuclease variant is double-stranded and comprises the reference sequence and its complement.

In a preferred embodiment, the target site is a sequence in a mouse and/or human PCSK9 gene. In particular embodiments, an HE or megaTAL can be designed to bind and cleave similar target sites in different species.

"Recombination" refers to a process of exchange of genetic information between two polynucleotides, including but not limited to, donor capture by non-homologous end joining (NHEJ) and homologous recombination. For the purposes of this disclosure, "homologous recombination (HR)" refers to the specialized form of such exchange that takes place, for example, during repair of double-strand breaks in cells via homology-directed repair (HDR) mechanisms. This process requires nucleotide sequence homology, uses a "donor" molecule as a template to repair a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"NHEJ" or "non-homologous end joining" refers to the resolution of a double-strand break in the absence of a donor repair template or homologous sequence. NHEJ can result in insertions and deletions at the site of the break. NHEJ is mediated by several sub-pathways, each of which has distinct mutational consequences. The classical NHEJ pathway (cNHEJ) requires the KU/DNA-PKcs/Lig4/XRCC4 complex, ligates ends back together with minimal processing and often leads to precise repair of the break. Alternative NHEJ pathways (altNHEJ) also are active in resolving dsDNA breaks, but these pathways are considerably more mutagenic and often result in imprecise repair of the break marked by insertions and deletions. While not wishing to be bound to any particular theory, it is contemplated that modification of dsDNA breaks by end-processing enzymes, such as, for example, exonucleases, e.g., Trex2, may increase the likelihood of imprecise repair.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible. Double-stranded cleavage can occur as a result of two distinct single-stranded cleavage events. DNA cleavage can result in the production of either blunt ends or staggered ends. In certain embodiments, polypeptides and nuclease variants, e.g., homing endonuclease variants, megaTALs, etc. contemplated herein are used for targeted double-stranded DNA cleavage. Endonuclease cleavage recognition sites may be on either DNA strand.

An "exogenous" molecule is a molecule that is not normally present in a cell, but that is introduced into a cell by one or more genetic, biochemical or other methods. Exemplary exogenous molecules include, but are not limited to small organic molecules, protein, nucleic acid, carbohydrate, lipid, glycoprotein, lipoprotein, polysaccharide, any modified derivative of the above molecules, or any complex comprising one or more of the above molecules. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, biopolymer nanoparticle, calcium phosphate co-precipitation, DEAE-dextran-mediated transfer and viral vector-mediated transfer.

An "endogenous" molecule is one that is normally present in a particular cell at a particular developmental stage under particular environmental conditions. Additional endogenous molecules can include proteins.

A "gene," refers to a DNA region encoding a gene product, as well as all DNA regions which regulate the production of the gene product, whether or not such regulatory sequences are adjacent to coding and/or transcribed sequences. A gene includes, but is not limited to, promoter sequences, enhancers, silencers, insulators, boundary elements, terminators, polyadenylation sequences, post-transcription response elements, translational regulatory sequences such as ribosome binding sites and internal ribosome entry sites, replication origins, matrix attachment sites, and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of an mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

As used herein, the term "genetically engineered" or "genetically modified" refers to the chromosomal or extra-chromosomal addition of extra genetic material in the form of DNA or RNA to the total genetic material in a cell. Genetic modifications may be targeted or non-targeted to a particular site in a cell's genome. In one embodiment, genetic modification is site specific. In one embodiment, genetic modification is not site specific.

As used herein, the term "genome editing" refers to the substitution, deletion, and/or introduction of genetic material at a target site in the cell's genome, which restores, corrects, disrupts, and/or modifies expression of a gene or gene product. Genome editing contemplated in particular embodiments comprises introducing one or more nuclease variants into a cell to generate DNA lesions at or proximal to a target site in the cell's genome, optionally in the presence of a donor repair template.

As used herein, the term "gene therapy" refers to the introduction of extra genetic material into the total genetic material in a cell that restores, corrects, or modifies expression of a gene or gene product, or for the purpose of expressing a therapeutic polypeptide. In particular embodiments, introduction of genetic material into the cell's genome by genome editing that restores, corrects, disrupts, or modifies expression of a gene or gene product, or for the purpose of expressing a therapeutic polypeptide is considered gene therapy.

Hypercholesterolemia refers to a metabolic condition characterized by the presence of excessively high cholesterol levels in the blood.

As used herein, the terms "individual" and "subject" are often used interchangeably and refer to an animal that can be treated with the nuclease variants, genome editing compositions, gene therapy vectors, genome editing vectors, genome edited cells, and methods contemplated elsewhere herein. Suitable subjects (e.g., patients) include laboratory animals (such as mouse, rat, rabbit, or guinea pig), farm animals, and domestic animals or pets (such as a cat or dog). Non-human primates and, preferably, human subjects, are included. Typical subjects include human patients that have, have been diagnosed with, or are at risk of having high cholesterol or hypercholesterolemia.

As used herein, the term "patient" refers to a subject that has, has been diagnosed with, or is at risk of having, high cholesterol or hypercholesterolemia or a condition associated therewith that can be treated with the nuclease variants, genome editing compositions, gene therapy vectors, genome editing vectors, genome edited cells, and methods contemplated elsewhere herein.

As used herein "treatment" or "treating," includes any beneficial or desirable effect on the symptoms or pathology of a disease or pathological condition, and may include even minimal reductions in one or more measurable markers of the disease or condition being treated. Treatment can optionally involve delaying of the progression of the disease or condition. "Treatment" does not necessarily indicate complete eradication or cure of the disease or condition, or associated symptoms thereof.

As used herein, "prevent," and similar words such as "prevention," "prevented," "preventing" etc., indicate an approach for preventing, inhibiting, or reducing the likelihood of the occurrence or recurrence of, a disease or condition. It also refers to delaying the onset or recurrence of a disease or condition or delaying the occurrence or recurrence of the symptoms of a disease or condition. As used herein, "prevention" and similar words also includes reducing the intensity, effect, symptoms and/or burden of a disease or condition prior to onset or recurrence of the disease or condition.

As used herein, the phrase "ameliorating at least one symptom of" refers to decreasing one or more symptoms of the disease or condition for which the subject is being treated. In particular embodiments, the disease or condition being treated is high cholesterol or hypercholesterolemia, wherein the one or more symptoms ameliorated include, but are not limited to, high cholesterol, atherosclerosis, heart disease, and the like.

As used herein, the term "amount" refers to "an amount effective" or "an effective amount" of a nuclease variant, genome editing composition, or genome edited cell sufficient to achieve a beneficial or desired prophylactic or therapeutic result, including clinical results.

A "prophylactically effective amount" refers to an amount of a nuclease variant, genome editing composition, or genome edited cell sufficient to achieve the desired prophylactic result. Typically but not necessarily, since a prophylactic dose is used in subjects prior to or at an earlier stage of disease, the prophylactically effective amount is less than the therapeutically effective amount.

A "therapeutically effective amount" of a nuclease variant, genome editing composition, or genome edited cell may vary according to factors such as the disease state, age, sex, and weight of the individual, and the ability to elicit a desired response in the individual. A therapeutically effective amount is also one in which any toxic or detrimental effects are outweighed by the therapeutically beneficial effects. The term "therapeutically effective amount" includes an amount that is effective to "treat" a subject (e.g., a patient). When a therapeutic amount is indicated, the precise amount of the compositions contemplated in particular embodiments, to be administered, can be determined by a physician in view of the specification and with consideration of individual differences in age, weight, tumor size, extent of infection or metastasis, and condition of the patient (subject).

C. Nuclease Variants

Nuclease variants contemplated in particular embodiments herein are suitable for genome editing a target site in a PCSK9 gene and comprise one or more DNA binding domains and one or more DNA cleavage domains (e.g., one or more endonuclease and/or exonuclease domains), and optionally, one or more linkers contemplated herein. The terms "reprogrammed nuclease," "engineered nuclease," or "nuclease variant" are used interchangeably and refer to a nuclease comprising one or more DNA binding domains and one or more DNA cleavage domains, wherein the nuclease has been designed and/or modified from a parental or naturally occurring nuclease, to bind and cleave a double-stranded DNA target sequence in a PCSK9 gene.

In particular embodiments, a nuclease variant binds and cleaves a target sequence in exon 4 of a PCSK9 gene, preferably at SEQ ID NO: 11 in exon 4 of a PCSK9 gene, and more preferably at the sequence "ATAC" in SEQ ID NO: 11 in exon 4 of a PCSK9 gene.

The nuclease variant may be designed and/or modified from a naturally occurring nuclease or from a previous nuclease variant. Nuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5'exonuclease (e.g., Trex2), 5' flap endonuclease, helicase, template-dependent DNA polymerases or template-independent DNA polymerase activity.

Illustrative examples of nuclease variants that bind and cleave a target sequence in the PCSK9 gene include, but are not limited to homing endonuclease (meganuclease) variants and megaTALs.

1. Homing Endonuclease (Meganuclease) Variants

In various embodiments, a homing endonuclease or meganuclease is reprogrammed to introduce a double-strand break (DSB) in a target site in a mouse and/or human PCSK9 gene. In particular embodiments, a homing endonuclease variant introduces a double strand break in exon 4 of a PCSK9 gene, preferably at SEQ ID NO: 11 in exon 4 of a PCSK9 gene, and more preferably at the sequence "ATAC" in SEQ ID NO: 11 in exon 4 of a PCSK9 gene.

"Homing endonuclease" and "meganuclease" are used interchangeably and refer to naturally-occurring homing endonucleases that recognize 12-45 base-pair cleavage sites and are commonly grouped into five families based on sequence and structure motifs: LAGLIDADG, GIY-YIG, HNH, His-Cys box, and PD-(D/E)XK.

A "reference homing endonuclease" or "reference meganuclease" refers to a wild type homing endonuclease or a homing endonuclease found in nature. In one embodiment, a "reference homing endonuclease" refers to a wild type homing endonuclease that has been modified to increase basal activity.

An "engineered homing endonuclease," "reprogrammed homing endonuclease," "homing endonuclease variant," "engineered meganuclease," "reprogrammed meganuclease," or "meganuclease variant" refers to a homing endonuclease comprising one or more DNA binding domains and one or more DNA cleavage domains, wherein the homing endonuclease has been designed and/or modified from a parental or naturally occurring homing endonuclease, to bind and cleave a DNA target sequence in a PCSK9 gene. The homing endonuclease variant may be designed and/or modified from a naturally occurring homing endonuclease or from another homing endonuclease variant. Homing endonuclease variants contemplated in particular embodiments may further comprise one or more additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template dependent DNA polymerase or template-independent DNA polymerase activity.

Homing endonuclease (HE) variants do not exist in nature and can be obtained by recombinant DNA technology or by random mutagenesis. HE variants may be obtained by making one or more amino acid alterations, e.g., mutating, substituting, adding, or deleting one or more amino acids, in a naturally occurring HE or HE variant. In particular embodiments, a HE variant comprises one or more amino acid alterations to the DNA recognition interface.

HE variants contemplated in particular embodiments may further comprise one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. In particular embodiments, HE variants are introduced into a T cell with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase or template-independent DNA polymerase activity. The HE variant and 3' processing enzyme may be introduced separately, e.g., in different vectors or separate mRNAs, or together, e.g., as a fusion protein, or in a polycistronic construct separated by a viral self-cleaving peptide or an IRES element.

A "DNA recognition interface" refers to the HE amino acid residues that interact with nucleic acid target bases as well as those residues that are adjacent. For each HE, the DNA recognition interface comprises an extensive network of side chain-to-side chain and side chain-to-DNA contacts, most of which is necessarily unique to recognize a particular nucleic acid target sequence. Thus, the amino acid sequence of the DNA recognition interface corresponding to a particular nucleic acid sequence varies significantly and is a feature of any natural or HE variant. By way of non-limiting example, a HE variant contemplated in particular embodiments may be derived by constructing libraries of HE variants in which one or more amino acid residues localized in the DNA recognition interface of the natural HE (or a previously generated HE variant) are varied. The libraries may be screened for target cleavage activity against each predicted PCSK9 target site using cleavage assays (see e.g., Jarjour et al., 2009. *Nuc. Acids Res.* 37(20): 6871-6880).

LAGLIDADG homing endonucleases (LHE) are the most well studied family of homing endonucleases, are primarily encoded in archaea and in organellar DNA in green algae and fungi, and display the highest overall DNA recognition specificity. LHEs comprise one or two LAGLIDADG catalytic motifs per protein chain and function as homodimers or single chain monomers, respectively. Structural studies of LAGLIDADG proteins identified a highly conserved core structure (Stoddard 2005), characterized by an αββαββα fold, with the LAGLIDADG motif belonging to the first helix of this fold. The highly efficient and specific cleavage of LHE's represent a protein scaffold to derive novel, highly specific endonucleases.

However, engineering LHEs to bind and cleave a non-natural or non-canonical target site requires selection of the appropriate LHE scaffold, examination of the target locus, selection of putative target sites, and extensive alteration of the LHE to alter its DNA contact points and cleavage specificity, at up to two-thirds of the base-pair positions in a target site.

In one embodiment, LHEs from which reprogrammed LHEs or LHE variants may be designed include, but are not limited to I-CreI and I-SceI.

Illustrative examples of LHEs from which reprogrammed LHEs or LHE variants may be designed include, but are not limited to I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-Ncrl, I-NcrMI, I-OheMI, I-OnuI, I-OsoMI, I-OsoMII, I-OsoMIII, I-OsoMIV, I-PanMI, I-PanMII, I-PanMIII, I-PnoMI, I-ScuMI, I-SmaMI, I-SscMI, and I-Vdil41I.

In one embodiment, the reprogrammed LHE or LHE variant is selected from the group consisting of: an I-CpaMI variant, an I-HjeMI variant, an I-OnuI variant, an I-PanMI variant, and an I-SmaMI variant.

In one embodiment, the reprogrammed LHE or LHE variant is an I-OnuI variant. See e.g., SEQ ID NOs: 6-7.

In one embodiment, reprogrammed I-OnuI LHEs or I-OnuI variants targeting the PCSK9 gene were generated from a natural I-OnuI or biologically active fragment thereof (SEQ ID NOs: 1-5). In a preferred embodiment, reprogrammed I-OnuI LHEs or I-OnuI variants targeting a PCSK9 gene were generated from an existing I-OnuI variant. In one embodiment, reprogrammed I-OnuI LHEs were generated against a PCSK9 gene target site set forth in SEQ ID NO: 11.

In a particular embodiment, the reprogrammed I-OnuI LHE or I-OnuI variant that binds and cleaves a PCSK9 gene comprises one or more amino acid substitutions in the DNA recognition interface. In particular embodiments, the I-OnuI LHE that binds and cleaves a PCSK9 gene comprises at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity with the DNA recognition interface of I-OnuI (Taekuchi et al. 2011. *Proc Natl Acad Sci U.S.A* 2011 Aug. 9; 108(32): 13077-13082) or an I-OnuI LHE variant as set forth in any one of SEQ ID NOs: 6-7, biologically active fragments thereof, and/or further variants thereof.

In one embodiment, the I-OnuI LHE that binds and cleaves a PCSK9 gene comprises at least 70%, more preferably at least 80%, more preferably at least 85%, more preferably at least 90%, more preferably at least 95%, more preferably at least 97%, more preferably at least 99% sequence identity with the DNA recognition interface of I-OnuI (Taekuchi et al. 2011. *Proc Natl Acad Sci U.S.A* 2011 Aug. 9; 108(32): 13077-13082) or an I-OnuI LHE variant as set forth in any one of SEQ ID NOs: 6-7, biologically active fragments thereof, and/or further variants thereof.

In a particular embodiment, an I-OnuI LHE variant that binds and cleaves a PCSK9 gene comprises one or more amino acid substitutions or modifications in the DNA recognition interface of an I-OnuI as set forth in any one of SEQ ID NOs: 1-7, biologically active fragments thereof, and/or further variants thereof.

In a particular embodiment, an I-OnuI LHE variant that binds and cleaves a PCSK9 gene comprises one or more amino acid substitutions or modifications in the DNA recognition interface, particularly in the subdomains situated from positions 24-50, 68 to 82, 180 to 203 and 223 to 240 of I-OnuI (SEQ ID NOs: 1-5) or an I-OnuI variant as set forth in any one of SEQ ID NOs: 6-7, biologically active fragments thereof, and/or further variants thereof.

In a particular embodiment, an I-OnuI LHE that binds and cleaves a PCSK9 gene comprises one or more amino acid substitutions or modifications in the DNA recognition interface at amino acid positions selected from the group consisting of 24, 26, 28, 30, 32, 34, 35, 36, 37, 38, 40, 42, 44, 46, 48, 68, 70, 72, 75, 76, 78, 80, 82, 180, 182, 184, 186, 188, 189, 190, 191, 192, 193, 195, 197, 199, 201, 203, 223, 225, 227, 229, 231, 232, 234, 236, 238, and 240 of I-OnuI (SEQ ID NOs: 1-5) or an I-OnuI variant as set forth in any one of SEQ ID NOs: 6-7, biologically active fragments thereof, and/or further variants thereof.

In a particular embodiment, an I-OnuI LHE variant that binds and cleaves a PCSK9 gene comprising 5, 10, 15, 20, 25, 30, 35, or 40 or more amino acid substitutions or modifications in the DNA recognition interface, particularly in the subdomains situated from positions 24-50, 68 to 82, 180 to 203 and 223 to 240 of I-OnuI (SEQ ID NOs: 1-5) or an I-OnuI variant as set forth in any one of SEQ ID NOs: 6-7, biologically active fragments thereof, and/or further variants thereof.

In a particular embodiment, an I-OnuI LHE variant that binds and cleaves a PCSK9 gene comprises 5, 10, 15, 20, 25, 30, 35, or 40 or more amino acid substitutions or modifications in the DNA recognition interface at amino acid positions selected from the group consisting of 24, 26, 28, 30, 32, 34, 35, 36, 37, 38, 40, 42, 44, 46, 48, 68, 70, 72, 75, 76, 78, 80, 82, 180, 182, 184, 186, 188, 189, 190, 191, 192, 193, 195, 197, 199, 201, 203, 223, 225, 227, 229, 231, 232, 234, 236, 238, and 240 of I-OnuI (SEQ IDNOs: 1-5) or an I-OnuI variant as set forth in any one of SEQ ID NOs: 6-7, biologically active fragments thereof, and/or further variants thereof.

In one embodiment, an I-OnuI LHE variant that binds and cleaves a PCSK9 gene comprises one or more amino acid substitutions or modifications at additional positions situated anywhere within the entire I-OnuI sequence. The residues which may be substituted and/or modified include but are not limited to amino acids that contact the nucleic acid target or that interact with the nucleic acid backbone or with the nucleotide bases, directly or via a water molecule. In one non-limiting example, an I-OnuI LHE variant contemplated herein that binds and cleaves a PCSK9 gene comprises one or more substitutions and/or modifications, preferably at least 5, preferably at least 10, preferably at least 15, preferably at least 20, more preferably at least 25, more preferably at least 30, even more preferably at least 35, or even more preferably at least 40 or more amino acid substitutions in at least one position selected from the position group consisting of positions: 24, 26, 28, 30, 32, 34, 35, 36, 37, 38, 40, 42, 44, 46, 48, 61, 68, 70, 72, 75, 76, 78, 80, 82, 116, 138, 143, 159, 168, 178, 180, 182, 184, 186, 188, 189, 190, 191, 192, 193, 195, 197, 199, 203, 207, 223, 225, 227, 232, and 236 of I-OnuI (SEQ ID NOs: 1-5) or an I-OnuI variant as set forth in any one of SEQ ID NOs: 6-7, biologically active fragments thereof, and/or further variants thereof.

In certain embodiments, the HE variant cleaves a PCSK9 exon 4 target site and comprises at least 5, at least 15, preferably at least 25, more preferably at least 35, or even more preferably at least 40 or more of the following amino acid substitutions: S24C, L26M, R28N, R30W, N32K, K34R, S35T, S36R, V37A, G38K, S40Y, E42A, G44R, Q46E, T48A, Q61R, V68K, A70R, S72I, N75R, A76V, S78K, K80V, T82G, V116L, L138M, T143N, S159P, F168L, E178D, C180Y, F182G, N184E, I186M, S188R, K189T, S190T, K191G, L192T, G193H, Q195T, Q197R, V199R, T203A, K207R, Y223R, K225S, K227R, F232Y, and D236E of I-OnuI (SEQ ID NOs: 1-5) or an I-OnuI variant as set forth in any one of SEQ ID NOs: 6-7, biologically active fragments thereof, and/or further variants thereof.

In some embodiments, the HE variant cleaves a PCSK9 target site and comprises at least 5, at least 15, preferably at least 25, more preferably at least 35, or even more preferably at least 40 or more of the following amino acid substitutions: S24C, L26M, R28N, R30W, N32K, K34R, S35T, S36R, V37A, G38K, S40Y, E42A, G44R, Q46E, T48A, Q61R, V68K, A70R, S72I, N75R, A76V, S78K, K80V, T82G, V116L, L138M, T143N, S159P, F168L, E178D, C180Y, F182G, N184E, I186M, S188R, S190T, K191G, L192T, G193H, Q195T, Q197R, V199R, T203A, K207R, Y223R, K225S, K227R, F232Y, and D236E of I-OnuI (SEQ ID NOs: 1-5) or an I-OnuI variant as set forth in any one of SEQ ID NOs: 6-7, biologically active fragments thereof, and/or further variants thereof.

In particular embodiments, the HE variant cleaves a PCSK9 target site and comprises at least 5, at least 15, preferably at least 25, more preferably at least 35, or even more preferably at least 40 or more of the following amino acid substitutions: S24C, L26M, R28N, R30W, N32K, K34R, S35T, S36R, V37A, G38K, S40Y, E42A, G44R, Q46E, T48A, Q61R, V68K, A70R, S72I, N75R, A76V, S78K, K80V, T82G, V116L, L138M, T143N, S159P, F168L, E178D, C180Y, F182G, N184E, I186M, S188R, K189T, S190T, K191G, L192T, G193H, Q195T, Q197R, V199R, K207R, Y223R, K225S, K227R, F232Y, and D236E of I-OnuI (SEQ ID NOs: 1-5) or an I-OnuI variant as set forth in any one of SEQ ID NOs: 6-7, biologically active fragments thereof, and/or further variants thereof.

In particular embodiments, an I-OnuI LHE variant that binds and cleaves a mouse and/or human PCSK9 gene comprises an amino acid sequence that is at least 80%, preferably at least 85%, more preferably at least 90%, or even more preferably at least 95% identical to the amino acid sequence set forth in any one of SEQ ID NOs: 6-7, or a biologically active fragment thereof.

In particular embodiments, an I-OnuI LHE variant comprises an amino acid sequence set forth in any one of SEQ ID NOs: 6-7, or a biologically active fragment thereof.

In particular embodiments, an I-OnuI LHE variant comprises an amino acid sequence set forth in SEQ ID NO: 6, or a biologically active fragment thereof.

In particular embodiments, an I-OnuI LHE variant comprises an amino acid sequence set forth in SEQ ID NO: 7, or a biologically active fragment thereof.

2. MegaTALs

In various embodiments, a megaTAL comprising a homing endonuclease variant is reprogrammed to introduce a double-strand break (DSB) in a target site in a PCSK9 gene. In particular embodiments, a megaTAL introduces a DSB in exon 4 of a PCSK9 gene, preferably at SEQ ID NO: 11 in exon 4 of a PCSK9 gene, and more preferably at the sequence "ATAC" in SEQ ID NO: 11 in exon 4 of a PCSK9 gene.

A "megaTAL" refers to a polypeptide comprising a TALE DNA binding domain and a homing endonuclease variant that binds and cleaves a DNA target sequence in a PCSK9 gene, and optionally comprises one or more linkers and/or additional functional domains, e.g., an end-processing enzymatic domain of an end-processing enzyme that exhibits 5'-3' exonuclease, 5'-3' alkaline exonuclease, 3'-5' exonuclease (e.g., Trex2), 5' flap endonuclease, helicase or template-independent DNA polymerase activity.

In particular embodiments, a megaTAL can be introduced into a cell along with an end-processing enzyme that exhibits 5'-3' exonuclease, 5'-3' alkaline exonuclease, 3'-5' exonuclease (e.g., Trex2), 5' flap endonuclease, helicase, template-dependent DNA polymerase, or template-independent DNA polymerase activity. The megaTAL and 3' processing enzyme may be introduced separately, e.g., in different vectors or separate mRNAs, or together, e.g., as a fusion protein, or in a polycistronic construct separated by a viral self-cleaving peptide or an IRES element.

A "TALE DNA binding domain" is the DNA binding portion of transcription activator-like effectors (TALE or TAL-effectors), which mimics plant transcriptional activators to manipulate the plant transcriptome (see e.g., Kay et al., 2007. Science 318:648-651). TALE DNA binding domains contemplated in particular embodiments are engineered de novo or from naturally occurring TALEs, e.g., AvrBs3 from *Xanthomonas* campestrispv. vesicatoria, *Xanthomonas gardneri*, *Xanthomonas translucens*, *Xanthomonas axonopodis*, *Xanthomonas perforans*, *Xanthomonas alfalfa*, *Xanthomonas citri*, *Xanthomonas euvesicatoria*, and *Xanthomonas oryzae* and brg11 and hpx17 from *Ralstonia solanacearum*. Illustrative examples of TALE proteins for deriving and designing DNA binding domains are disclosed in U.S. Pat. No. 9,017,967, and references cited therein, all of which are incorporated herein by reference in their entireties.

In particular embodiments, a megaTAL comprises a TALE DNA binding domain comprising one or more repeat units that are involved in binding of the TALE DNA binding domain to its corresponding target DNA sequence. A single "repeat unit" (also referred to as a "repeat") is typically 33-35 amino acids in length. Each TALE DNA binding domain repeat unit includes 1 or 2 DNA-binding residues making up the Repeat Variable Di-Residue (RVD), typically at positions 12 and/or 13 of the repeat. The natural (canonical) code for DNA recognition of these TALE DNA binding domains has been determined such that an HD sequence at positions 12 and 13 leads to a binding to cytosine (C), NG binds to T, NI to A, NN binds to G or A, and NG binds to T. In certain embodiments, non-canonical (atypical) RVDs are contemplated.

Illustrative examples of non-canonical RVDs suitable for use in particular megaTALs contemplated in particular embodiments include, but are not limited to HH, KH, NH, NK, NQ, RH, RN, SS, NN, SN, KN for recognition of guanine (G); NI, KI, RI, HI, SI for recognition of adenine (A); NG, HG, KG, RG for recognition of thymine (T); RD, SD, HD, ND, KD, YG for recognition of cytosine (C); NV, HN for recognition of A or G; and H*, HA, KA, N*, NA, NC, NS, RA, S*for recognition of A or T or G or C, wherein (*) means that the amino acid at position 13 is absent. Additional illustrative examples of RVDs suitable for use in particular megaTALs contemplated in particular embodiments further include those disclosed in U.S. Pat. No. 8,614,092, which is incorporated herein by reference in its entirety.

In particular embodiments, a megaTAL contemplated herein comprises a TALE DNA binding domain comprising 3 to 30 repeat units. In certain embodiments, a megaTAL comprises 3, 4, 5, 6, 7, 8, 9, 10, 11, 12, 13, 14, 15, 16, 17, 18, 19, 20, 21, 22, 23, 24, 25, 26, 27, 28, 29, or 30 TALE DNA binding domain repeat units. In a preferred embodiment, a megaTAL contemplated herein comprises a TALE DNA binding domain comprising 5-15 repeat units, more preferably 7-15 repeat units, more preferably 9-15 repeat units, and more preferably 9, 10, 11, 12, 13, 14, or 15 repeat units.

In particular embodiments, a megaTAL contemplated herein comprises a TALE DNA binding domain comprising 3 to 30 repeat units and an additional single truncated TALE repeat unit comprising 20 amino acids located at the C-terminus of a set of TALE repeat units, i.e., an additional C-terminal half-TALE DNA binding domain repeat unit (amino acids-20 to -1 of the C-cap disclosed elsewhere herein, infra). Thus, in particular embodiments, a megaTAL contemplated herein comprises a TALE DNA binding domain comprising 3.5 to 30.5 repeat units. In certain embodiments, a megaTAL comprises 3.5, 4.5, 5.5, 6.5, 7.5, 8.5, 9.5, 10.5, 11.5, 12.5, 13.5, 14.5, 15.5, 16.5, 17.5, 18.5, 19.5, 20.5, 21.5, 22.5, 23.5, 24.5, 25.5, 26.5, 27.5, 28.5, 29.5, or 30.5 TALE DNA binding domain repeat units. In a preferred embodiment, a megaTAL contemplated herein comprises a TALE DNA binding domain comprising 5.5-15.5 repeat units, more preferably 7.5-15.5 repeat units, more preferably 9.5-15.5 repeat units, and more preferably 9.5, 10.5, 11.5, 12.5, 13.5, 14.5, or 15.5 repeat units.

In particular embodiments, a megaTAL comprises a TAL effector architecture comprising an "N-terminal domain (NTD)" polypeptide, one or more TALE repeat domains/units, a "C-terminal domain (CTD)" polypeptide, and a homing endonuclease variant. In some embodiments, the NTD, TALE repeats, and/or CTD domains are from the same species. In other embodiments, one or more of the NTD, TALE repeats, and/or CTD domains are from different species.

As used herein, the term "N-terminal domain (NTD)" polypeptide refers to the sequence that flanks the N-terminal portion or fragment of a naturally occurring TALE DNA binding domain. The NTD sequence, if present, may be of any length as long as the TALE DNA binding domain repeat units retain the ability to bind DNA. In particular embodiments, the NTD polypeptide comprises at least 120 to at least 140 or more amino acids N-terminal to the TALE DNA binding domain (0 is amino acid 1 of the most N-terminal repeat unit). In particular embodiments, the NTD polypeptide comprises at least about 120, 121, 122, 123, 124, 125, 126, 127, 128, 129, 130, 131, 132, 133, 134, 135, 136, 137, 138, 139, or at least 140 amino acids N-terminal to the TALE DNA binding domain. In one embodiment, a megaTAL contemplated herein comprises an NTD polypeptide of at least about amino acids+1 to +122 to at least about +1 to +137 of a Xanthomonas TALE protein (0 is amino acid 1 of the most N-terminal repeat unit). In particular embodiments, the NTD polypeptide comprises at least about 122, 123, 124, 125, 126, 127, 128, 129, 130, 131, 132, 133, 134, 135, 136, or 137 amino acids N-terminal to the TALE DNA binding domain of a Xanthomonas TALE protein. In one embodiment, a megaTAL contemplated herein comprises an NTD polypeptide of at least amino acids+1 to +121 of a Ralstonia TALE protein (0 is amino acid 1 of the most N-terminal repeat unit). In particular embodiments, the NTD polypeptide comprises at least about 121, 122, 123, 124, 125, 126, 127, 128, 129, 130, 131, 132, 133, 134, 135, 136, or 137 amino acids N-terminal to the TALE DNA binding domain of a Ralstonia TALE protein.

As used herein, the term "C-terminal domain (CTD)" polypeptide refers to the sequence that flanks the C-terminal portion or fragment of a naturally occurring TALE DNA binding domain. The CTD sequence, if present, may be of any length as long as the TALE DNA binding domain repeat units retain the ability to bind DNA. In particular embodiments, the CTD polypeptide comprises at least 20 to at least 85 or more amino acids C-terminal to the last full repeat of the TALE DNA binding domain (the first 20 amino acids are the half-repeat unit C-terminal to the last C-terminal full repeat unit). In particular embodiments, the CTD polypeptide comprises at least about 20, 21, 22, 23, 24, 25, 26, 27, 28, 29, 30, 31, 32, 33, 34, 35, 36, 37, 38, 39, 40, 41, 42, 443, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, or at least 85 amino acids C-terminal to the last full repeat of the TALE DNA binding domain.

In one embodiment, a megaTAL contemplated herein comprises a CTD polypeptide of at least about amino acids-20 to -1 of a Xanthomonas TALE protein (-20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a Xanthomonas TALE protein. In one embodiment, a megaTAL contemplated herein comprises a CTD polypeptide of at least about amino acids-20 to -1 of a Ralstonia TALE protein (-20 is amino acid 1 of a half-repeat unit C-terminal to the last C-terminal full repeat unit). In particular embodiments, the CTD polypeptide comprises at least about 20, 19, 18, 17, 16, 15, 14, 13, 12, 11, 10, 9, 8, 7, 6, 5, 4, 3, 2, or 1 amino acids C-terminal to the last full repeat of the TALE DNA binding domain of a Ralstonia TALE protein.

In particular embodiments, a megaTAL contemplated herein, comprises a fusion polypeptide comprising a TALE DNA binding domain engineered to bind a target sequence, a homing endonuclease reprogrammed to bind and cleave a target sequence, and optionally an NTD and/or CTD polypeptide, optionally joined to each other with one or more linker polypeptides contemplated elsewhere herein. Without wishing to be bound by any particular theory, it is contemplated that a megaTAL comprising TALE DNA binding domain, and optionally an NTD and/or CTD polypeptide is fused to a linker polypeptide which is further fused to a homing endonuclease variant. Thus, the TALE DNA binding domain binds a DNA target sequence that is within about 1, 2, 3, 4, 5, 6, 7, 8, 9, 10, 11, 12, 13, 14, or 15 nucleotides away from the target sequence bound by the DNA binding domain of the homing endonuclease variant. In this way, the megaTALs contemplated herein, increase the specificity and efficiency of genome editing.

In one embodiment, a megaTAL comprises a homing endonuclease variant and a TALE DNA binding domain that binds a nucleotide sequence that is within about 4, 5, or 6 nucleotides, preferably 5 or 6 nucleotides, and more preferably 6 nucleotides, upstream of the binding site of the reprogrammed homing endonuclease.

In one embodiment, a megaTAL comprises a homing endonuclease variant and a TALE DNA binding domain that binds the nucleotide sequence set forth in SEQ ID NO: 12, which is 6 nucleotides upstream (i.e., there are 5 nucleotides between the TALE binding site and the HE binding site) of the nucleotide sequence bound and cleaved by the homing endonuclease variant (SEQ ID NO: 11). In preferred embodiments, the megaTAL target sequence is SEQ ID NO: 13.

In particular embodiments, a megaTAL contemplated herein, comprises one or more TALE DNA binding repeat units and an LHE variant designed or reprogrammed from an LHE selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanIIII, I-PnoMI, I-ScuMI, I-SmaMI, I-SscMI, I-Vdi141I and variants thereof, or preferably I-CpaMI, I-HjeMI, I-OnuI, I-PanMI, SmaMI and variants thereof, or more preferably I-OnuI and variants thereof.

In particular embodiments, a megaTAL contemplated herein, comprises an NTD, one or more TALE DNA binding repeat units, a CTD, and an LHE variant selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MeMI, I-NcrII, I-NcrI, I-NcrMI, I-OheMI, I-OnuI, I-OsoMI, I-OsoMII, I-OsoMIII, I-OsoMIV, I-PanNI, I-PanII, I-PanMIII, I-PnoMI, I-ScuMI, I-SmaMI, I-SscMI, I-Vdi141I and variants thereof, or preferably I-CpaMI, I-HjeMI, I-OnuI, I-PanII, SmaMI and variants thereof, or more preferably I-OnuI and variants thereof.

In particular embodiments, a megaTAL contemplated herein, comprises an NTD, about 9.5 to about 15.5 TALE DNA binding repeat units, and an LHE variant selected from the group consisting of: I-AabMI, I-AaeMI, I-AniI, I-ApaMI, I-CapIII, I-CapIV, I-CkaMI, I-CpaMI, I-CpaMII, I-CpaMIII, I-CpaMIV, I-CpaMV, I-CpaV, I-CraMI, I-EjeMI, I-GpeMI, I-GpiI, I-GzeMI, I-GzeMII, I-GzeMIII, I-HjeMI, I-LtrII, I-LtrI, I-LtrWI, I-MpeMI, I-MveMI, I-NcrII, I-NcrI, I-NcrMI, I-OheMI, I-OnuI, I-OsoMI, I-OsoMII, I-OsoMIII, I-OsoMIV, I-PanMI, I-PanMII, I-PanIIII, I-PnoMI, I-ScuMI, I-SmaMI, I-SscMI, I-Vdi141I and variants thereof, or preferably I-CpaMI, I-HjeMI, I-OnuI, I-PanMI, SmaMI and variants thereof, or more preferably I-OnuI and variants thereof.

In particular embodiments, a megaTAL contemplated herein, comprises an NTD of about 122 amino acids to 137 amino acids, about 9.5, about 10.5, about 11.5, about 12.5, about 13.5, about 14.5, or about 15.5 binding repeat units, a CTD of about 20 amino acids to about 85 amino acids, and an I-OnuI LHE variant. In particular embodiments, any one of, two of, or all of the NTD, DNA binding domain, and CTD can be designed from the same species or different species, in any suitable combination.

In particular embodiments, a megaTAL contemplated herein, comprises the amino acid sequence set forth in any one of SEQ ID NOs: 8-9.

In particular embodiments, a megaTAL-Trex2 fusion protein contemplated herein, comprises the amino acid sequence set forth in SEQ ID NO: 10.

In certain embodiments, a megaTAL comprises a TALE DNA binding domain and an I-OnuI LHE variant binds and cleaves the nucleotide sequence set forth in SEQ ID NO: 11 or SEQ ID NO: 13.

3. End-Processing Enzymes

Genome editing compositions and methods contemplated in particular embodiments comprise editing cellular genomes using a nuclease variant and one or more copies of an end-processing enzyme. In particular embodiments, a single polynucleotide encodes a homing endonuclease variant and an end-processing enzyme, separated by a linker, a self-cleaving peptide sequence, e.g., 2A sequence, or by an RES sequence. In particular embodiments, genome editing compositions comprise a polynucleotide encoding a nuclease variant and a separate polynucleotide encoding an end-processing enzyme. In particular embodiments, genome editing compositions comprise a polynucleotide encoding a homing endonuclease variant end-processing enzyme single polypeptide fusion in addition to a tandem copy of the end-processing enzyme separated by a self-cleaving peptide.

The term "end-processing enzyme" refers to an enzyme that modifies the exposed ends of a polynucleotide chain. The polynucleotide may be double-stranded DNA (dsDNA), single-stranded DNA (ssDNA), RNA, double-stranded hybrids of DNA and RNA, and synthetic DNA (for example, containing bases other than A, C, G, and T). An end-processing enzyme may modify exposed polynucleotide chain ends by adding one or more nucleotides, removing one or more nucleotides, removing or modifying a phosphate group and/or removing or modifying a hydroxyl group. An end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents.

In particular embodiments, genome editing compositions and methods contemplated in particular embodiments comprise editing cellular genomes using a homing endonuclease variant or megaTAL and a DNA end-processing enzyme.

The term "DNA end-processing enzyme" refers to an enzyme that modifies the exposed ends of DNA. A DNA end-processing enzyme may modify blunt ends or staggered ends (ends with 5' or 3' overhangs). A DNA end-processing enzyme may modify single stranded or double stranded DNA. A DNA end-processing enzyme may modify ends at endonuclease cut sites or at ends generated by other chemical or mechanical means, such as shearing (for example by passing through fine-gauge needle, heating, sonicating, mini bead tumbling, and nebulizing), ionizing radiation, ultraviolet radiation, oxygen radicals, chemical hydrolysis and chemotherapy agents. DNA end-processing enzyme may modify exposed DNA ends by adding one or more nucleotides, removing one or more nucleotides, removing or modifying a phosphate group and/or removing or modifying a hydroxyl group.

Illustrative examples of DNA end-processing enzymes suitable for use in particular embodiments contemplated herein include, but are not limited to: 5'-3' exonucleases, 5'-3' alkaline exonucleases, 3'-5' exonucleases, 5' flap endonucleases, helicases, phosphatases, hydrolases and template-independent DNA polymerases.

Additional illustrative examples of DNA end-processing enzymes suitable for use in particular embodiments contemplated herein include, but are not limited to, Trex2, Trex1, Trex1 without transmembrane domain, Apollo, Artemis, DNA2, Exo1, ExoT, ExoIII, Fen1, Fan1, MreII, Rad2, Rad9, TdT (terminal deoxynucleotidyl transferase), PNKP, RecE, RecJ, RecQ, Lambda exonuclease, Sox, Vaccinia DNA polymerase, exonuclease I, exonuclease III, exonuclease VII, NDK1, NDK5, NDK7, NDK8, WRN, T7-exonuclease Gene 6, avian myeloblastosis virus integration protein (IN), Bloom, Antartic Phophatase, Alkaline Phosphatase, Poly nucleotide Kinase (PNK), ApeI, Mung Bean nuclease, Hex1, TTRAP (TDP2), Sgsl, Sae2, CUP, Pol mu, Pol lambda, MUS81, EME1, EME2, SLX1, SLX4 and UL-12.

In particular embodiments, genome editing compositions and methods for editing cellular genomes contemplated herein comprise polypeptides comprising a homing endonuclease variant or megaTAL and an exonuclease. The term "exonuclease" refers to enzymes that cleave phosphodiester bonds at the end of a polynucleotide chain via a hydrolyzing reaction that breaks phosphodiester bonds at either the 3' or 5' end.

Illustrative examples of exonucleases suitable for use in particular embodiments contemplated herein include, but are not limited to: hExoI, Yeast ExoI, *E. coli* ExoI, hTREX2, mouse TREX2, rat TREX2, hTREX1, mouse TREX1, rat TREX1, and Rat TREX1.

In particular embodiments, the DNA end-processing enzyme is a 3' or 5' exonuclease, preferably Trex 1 or Trex2, more preferably Trex2, and even more preferably human or mouse Trex2.

D. Target Sites

Nuclease variants contemplated in particular embodiments can be designed to bind to any suitable target sequence and can have a novel binding specificity, compared to a naturally-occurring nuclease. In particular embodiments, the target site is a regulatory region of a gene including, but not limited to promoters, enhancers, repressor elements, and the like. In particular embodiments, the target site is a coding region of a gene or a splice site. In certain embodiments, nuclease variants are designed to down-regulate or decrease expression of a gene. In particular embodiments, a nuclease variant and donor repair template can be designed to repair or delete a desired target sequence.

In various embodiments, nuclease variants bind to and cleave a target sequence in a proprotein convertase subtilisin/kexin type 9 (PCSK9) gene. PCSK9 is also referred to as FH3, HCHOLA3 (hypercholesterolemia, autosomal dominant 3), NARC-1 or NARC1 (neural apoptosis regulated convertase 1), PC9 and proprotein convertase PC9. PCSK9 is a serine protease that reduces both hepatic and extrahepatic low-density lipoprotein (LDL) receptor (LDLR; levels and increases plasma LDL cholesterol.

In particular embodiments, a homing endonuclease variant or megaTAL introduces a double-strand break (DSB) in a target site in a PCSK9 gene. In particular embodiments, a homing endonuclease variant or megaTAL introduces a DSB in exon 4 of a PCSK9 gene, preferably at SEQ ID NO: 11 in exon 4 of a PCSK9 gene, and more preferably at the sequence "ATAC" in SEQ ID NO: 11 in exon 4 of a PCSK9 gene.

In a preferred embodiment, a homing endonuclease variant or megaTAL cleaves double-stranded DNA and introduces a DSB into the polynucleotide sequence set forth in SEQ ID NO: 11 or 13.

E. Donor Repair Templates

Nuclease variants may be used to introduce a DSB in a target sequence; the DSB may be repaired through homology directed repair (HDR) mechanisms in the presence of one or more donor repair templates.

In various embodiments, the donor repair template comprises one or more polynucleotides encoding a polypeptide.

In various embodiments, it is contemplated that providing a cell an engineered nuclease in the presence of a plurality of donor repair templates yields genome edited cells with increased therapeutic efficacy In particular embodiments, the donor repair template is used to insert a sequence into the genome. In particular preferred embodiments, the donor repair template is used to repair or modify a sequence in the genome.

In various embodiments, a donor repair template is introduced into a hepatic cell, by transducing the cell with an adeno-associated virus (AAV), retrovirus, e.g., lentivirus, IDLV, etc., herpes simplex virus, adenovirus, or vaccinia virus vector comprising the donor repair template.

In particular embodiments, the donor repair template comprises one or more homology arms that flank the DSB site.

As used herein, the term "homology arms" refers to a nucleic acid sequence in a donor repair template that is identical, or nearly identical, to DNA sequence flanking the DNA break introduced by the nuclease at a target site. In one embodiment, the donor repair template comprises a 5' homology arm that comprises a nucleic acid sequence that is identical or nearly identical to the DNA sequence 5' of the DNA break site. In one embodiment, the donor repair template comprises a 3' homology arm that comprises a nucleic acid sequence that is identical or nearly identical to the DNA sequence 3' of the DNA break site. In a preferred embodiment, the donor repair template comprises a 5' homology arm and a 3' homology arm. The donor repair template may comprise homology to the genome sequence immediately adjacent to the DSB site, or homology to the genomic sequence within any number of base pairs from the DSB site. In one embodiment, the donor repair template comprises a nucleic acid sequence that is homologous to a genomic sequence about 5 bp, about 10 bp, about 25 bp, about 50 bp, about 100 bp, about 250 bp, about 500 bp, about 1000 bp, about 2500 bp, about 5000 bp, about 10000 bp or more, including any intervening length of homologous sequence.

Illustrative examples of suitable lengths of homology arms contemplated in particular embodiments, may be independently selected, and include but are not limited to: about 100 bp, about 200 bp, about 300 bp, about 400 bp, about 500 bp, about 600 bp, about 700 bp, about 800 bp, about 900 bp, about 1000 bp, about 1100 bp, about 1200 bp, about 1300 bp, about 1400 bp, about 1500 bp, about 1600 bp, about 1700 bp, about 1800 bp, about 1900 bp, about 2000 bp, about 2100 bp, about 2200 bp, about 2300 bp, about 2400 bp, about 2500 bp, about 2600 bp, about 2700 bp, about 2800 bp, about 2900 bp, or about 3000 bp, or longer homology arms, including all intervening lengths of homology arms.

Additional illustrative examples of suitable homology arm lengths include, but are not limited to: about 100 bp to about 3000 bp, about 200 bp to about 3000 bp, about 300 bp to about 3000 bp, about 400 bp to about 3000 bp, about 500 bp to about 3000 bp, about 500 bp to about 2500 bp, about 500 bp to about 2000 bp, about 750 bp to about 2000 bp, about 750 bp to about 1500 bp, or about 1000 bp to about 1500 bp, including all intervening lengths of homology arms.

In a particular embodiment, the lengths of the 5' and 3' homology arms are independently selected from about 500 bp to about 1500 bp. In one embodiment, the 5'homology arm is about 1500 bp and the 3' homology arm is about 1000 bp. In one embodiment, the 5'homology arm is between about 200 bp to about 600 bp and the 3' homology arm is between about 200 bp to about 600 bp. In one embodiment, the 5'homology arm is about 200 bp and the 3' homology arm is about 200 bp. In one embodiment, the 5'homology arm is about 300 bp and the 3' homology arm is about 300 bp. In one embodiment, the 5'homology arm is about 400 bp and the 3' homology arm is about 400 bp.

In one embodiment, the 5'homology arm is about 500 bp and the 3' homology arm is about 500 bp. In one embodiment, the 5'homology arm is about 600 bp and the 3' homology arm is about 600 bp.

Donor repair templates may further comprises one or more polynucleotides such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, and polynucleotides encoding self-cleaving polypeptides, epitope tags, contemplated elsewhere herein.

In one embodiment, the donor repair template comprises a polynucleotide comprising a PCSK9 gene or portion thereof and is designed to introduce one or more mutations in a genomic PCSK9 sequence such that a mutant PCSK9 gene product is expressed. In one embodiment, the mutant PCSK9 has decreased activity.

In various embodiments, the donor repair template comprises a 5' homology arm, an RNA polymerase II promoter, one or more polynucleotides encoding a therapeutic polypeptide, and a 3' homology arm. In particular embodiments, the polynucleotide encodes a therapeutic polypeptide selected from the group consisting of: insulin, glucagon, growth hormone (GH), parathyroid hormone (PTH), growth hormone releasing factor (GRF), follicle stimulating hormone (FSH), luteinizing hormone (LH), human chorionic gonadotropin (hCG), vascular endothelial growth factor (VEGF), angiopoietins, angiostatin, granulocyte colony stimulating factor (GCSF), erythropoietin (EPO), connective tissue growth factor (CTGF), basic fibroblast growth factor (bFGF), acidic fibroblast growth factor (aFGF), epidermal growth factor (EGF), transforming growth factor.alpha. (TGFa), platelet-derived growth factor (PDGF), insulin growth factors I and II (IGF-I and IGF-II), TGFb, activins, inhibins, bone morphogenic protein (BMP), nerve growth factor (NGF), brain-derived neurotrophic factor (BDNF), neurotrophins NT-3 and NT4/5, ciliary neurotrophic factor (CNTF), glial cell line derived neurotrophic factor (GDNF), neurturin, agrin, netrin-1 and netrin-2, hepatocyte growth factor (HGF), ephrins, noggin, sonic hedgehog and tyrosine hydroxylase.

In various embodiments, a target site is modified with a donor repair template comprising a 5' homology arm, one or more polynucleotides encoding self-cleaving viral peptide, e.g., T2A, polynucleotide encoding a polypeptide, optionally a poly(A) signal or self-cleaving peptide, and a 3' homology arm, wherein expression of the one or more polynucleotides is governed by the endogenous PCSK9 promoter.

F. Polypeptides

Various polypeptides are contemplated herein, including, but not limited to, homing endonuclease variants, megaTALs, and fusion polypeptides. In preferred embodiments, a polypeptide comprises the amino acid sequence set forth in SEQ ID NOs: 1-10. "Polypeptide," "polypeptide fragment," "peptide" and "protein" are used interchangeably, unless specified to the contrary, and according to conventional meaning, i.e., as a sequence of amino acids. In one embodiment, a "polypeptide" includes fusion polypeptides and other variants. Polypeptides can be prepared using any of a variety of well-known recombinant and/or synthetic techniques. Polypeptides are not limited to a specific length, e.g., they may comprise a full-length protein sequence, a fragment of a full-length protein, or a fusion protein, and may include post-translational modifications of the polypeptide, for example, glycosylations, acetylations, phosphorylations and the like, as well as other modifications known in the art, both naturally occurring and non-naturally occurring.

An "isolated protein," "isolated peptide," or "isolated polypeptide" and the like, as used herein, refer to in vitro synthesis, isolation, and/or purification of a peptide or polypeptide molecule from a cellular environment, and from association with other components of the cell, i.e., it is not significantly associated with in vivo substances.

Illustrative examples of polypeptides contemplated in particular embodiments include, but are not limited to homing endonuclease variants, megaTALs, end-processing nucleases, fusion polypeptides and variants thereof.

Polypeptides include "polypeptide variants." Polypeptide variants may differ from a naturally occurring polypeptide in one or more amino acid substitutions, deletions, additions and/or insertions. Such variants may be naturally occurring or may be synthetically generated, for example, by modifying one or more amino acids of the above polypeptide sequences. For example, in particular embodiments, it may be desirable to improve the biological properties of a homing endonuclease, megaTAL or the like that binds and cleaves a target site in the mouse and/or human PCSK9 gene by introducing one or more substitutions, deletions, additions and/or insertions into the polypeptide. In particular embodiments, polypeptides include polypeptides having at least about 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% amino acid identity to any of the reference sequences contemplated herein, typically where the variant maintains at least one biological activity of the reference sequence.

Polypeptides variants include biologically active "polypeptide fragments." Illustrative examples of biologically active polypeptide fragments include DNA binding domains, nuclease domains, and the like. As used herein, the term "biologically active fragment" or "minimal biologically active fragment" refers to a polypeptide fragment that retains at least 100%, at least 90%, at least 80%, at least 70%, at least 60%, at least 50%, at least 40%, at least 30%, at least 20%, at least 10%, or at least 5% of the naturally occurring polypeptide activity. In preferred embodiments, the biological activity is binding affinity and/or cleavage activity for a target sequence. In certain embodiments, a polypeptide fragment can comprise an amino acid chain at least 5 to about 1700 amino acids long. It will be appreciated that in certain embodiments, fragments are at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more amino acids long. In particular embodiments, a polypeptide comprises a biologically active fragment of a homing endonuclease variant. In particular embodiments, the polypeptides set forth herein may comprise one or more amino acids denoted as "X." "X" if present in an amino acid SEQ ID NO, refers to any amino acid. One or more "X" residues may be present at the N- and C-terminus of an amino acid sequence set forth in particular SEQ ID NOs contemplated herein. If the "X" amino acids are not present the remaining amino acid sequence set forth in a SEQ ID NO may be considered a biologically active fragment.

In particular embodiments, a polypeptide comprises a biologically active fragment of a homing endonuclease variant, e.g., SEQ ID NOs: 3-7, or a megaTAL (SEQ ID NOs: 8-10). The biologically active fragment may comprise an N-terminal truncation and/or C-terminal truncation. In a particular embodiment, a biologically active fragment lacks or comprises a deletion of the 1, 2, 3, 4, 5, 6, 7, or 8 N-terminal amino acids of a homing endonuclease variant compared to a corresponding wild type homing endonuclease sequence, more preferably a deletion of the 4 N-terminal amino acids of a homing endonuclease variant compared to a corresponding wild type homing endonuclease sequence. In a particular embodiment, a biologically active fragment lacks or comprises a deletion of the 1, 2, 3, 4, or 5 C-terminal amino acids of a homing endonuclease variant compared to a corresponding wild type homing endonuclease sequence, more preferably a deletion of the 2 C-terminal amino acids of a homing endonuclease variant compared to a corresponding wild type homing endonuclease sequence. In a particular preferred embodiment, a biologically active fragment lacks or comprises a deletion of the 4 N-terminal amino acids and 2 C-terminal amino acids of a homing endonuclease variant compared to a corresponding wild type homing endonuclease sequence.

In a particular embodiment, an I-OnuI variant comprises a deletion of 1, 2, 3, 4, 5, 6, 7, or 8 of the following N-terminal amino acids: M, A, Y, M, S, R, R, E; and/or a deletion of the following 1 or 2 C-terminal amino acids: F, V.

In a particular embodiment, an I-OnuI variant comprises a deletion or substitution of 1, 2, 3, 4, 5, 6, 7, or 8 of the following N-terminal amino acids: M, A, Y, M, S, R, R, E; and/or a deletion or substitution of the following 1 or 2 C-terminal amino acids: F, V.

In a particular embodiment, an I-OnuI variant comprises a deletion of 1, 2, 3, 4, 5, 6, 7, or 8 of the following N-terminal amino acids: M, A, Y, M, S, R, R, E; and/or a deletion of the following 1, 2, 3, 4, or 5 C-terminal amino acids: R, G, S, F, V.

In a particular embodiment, an I-OnuI variant comprises a deletion or substitution of 1, 2, 3, 4, 5, 6, 7, or 8 of the following N-terminal amino acids: M, A, Y, M, S, R, R, E; and/or a deletion or substitution of the following 1, 2, 3, 4, or 5 C-terminal amino acids: R, G, S, F, V.

As noted above, polypeptides may be altered in various ways including amino acid substitutions, deletions, truncations, and insertions. Methods for such manipulations are generally known in the art. For example, amino acid sequence variants of a reference polypeptide can be prepared by mutations in the DNA. Methods for mutagenesis and nucleotide sequence alterations are well known in the art. See, for example, Kunkel (1985, *Proc. Natl. Acad. Sci. USA.* 82: 488-492), Kunkel et al., (1987, *Methods in Enzymol,* 154: 367-382), U.S. Pat. No. 4,873,192, Watson, J. D. et al., (Molecular Biology of the Gene, Fourth Edition, Benjamin/Cummings, Menlo Park, Calif., 1987) and the references cited therein. Guidance as to appropriate amino acid substitutions that do not affect biological activity of the protein of interest may be found in the model of Dayhoff et al., (1978) *Atlas of Protein Sequence and Structure (Natl. Biomed Res. Found.,* Washington, D.C.).

In certain embodiments, a variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Modifications may be made in the structure of the polynucleotides and polypeptides contemplated in particular embodiments, polypeptides include polypeptides having at least about and still obtain a functional molecule that encodes a variant or derivative polypeptide with desirable characteristics. When it is desired to alter the amino acid sequence of a polypeptide to create an equivalent, or even an improved, variant polypeptide, one skilled in the art, for example, can change one or more of the codons of the encoding DNA sequence, e.g., according to Table 1.

TABLE 1

Amino Acid Codons

| Amino Acids | One letter code | Three letter code | Codons | | | |
|---|---|---|---|---|---|---|
| Alanine | A | Ala | GCA | GCC | GCG | GCU |
| Cysteine | C | Cys | UGC | UGU | | |
| Aspartic acid | D | Asp | GAC | GAU | | |
| Glutamic acid | E | Glu | GAA | GAG | | |
| Phenylalanine | F | Phe | UUC | UUU | | |
| Glycine | G | Gly | GGA | GGC | GGG | GGU |
| Histidine | H | His | CAC | CAU | | |
| Isoleucine | I | Iso | AUA | AUC | AUU | |
| Lysine | K | Lys | AAA | AAG | | |
| Leucine | L | Leu | UUA | UUG | CUA | CUC | CUG | CUU |
| Methionine | M | Met | AUG | | | |
| Asparagine | N | Asn | AAC | AAU | | |
| Proline | P | Pro | CCA | CCC | CCG | CCU |
| Glutamine | Q | Gln | CAA | CAG | | |
| Arginine | R | Arg | AGA | AGG | CGA | CGC | CGG | CGU |
| Serine | S | Ser | AGC | AGU | UCA | UCC | UCG | UCU |
| Threonine | T | Thr | ACA | ACC | ACG | ACU |
| Valine | V | Val | GUA | GUC | GUG | GUU |
| Tryptophan | W | Trp | UGG | | | |
| Tyrosine | Y | Tyr | UAC | UAU | | |

Guidance in determining which amino acid residues can be substituted, inserted, or deleted without abolishing biological activity can be found using computer programs well known in the art, such as DNASTAR, DNA Strider, Geneious, Mac Vector, or Vector NTI software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains. Naturally occurring amino acids are generally divided into four families: acidic (aspartate, glutamate), basic (lysine, arginine, histidine), non-polar (alanine, valine, leucine, isoleucine, proline, phenylalanine, methionine, tryptophan), and uncharged polar (glycine, asparagine, glutamine, cysteine, serine, threonine, tyrosine) amino acids. Phenylalanine, tryptophan, and tyrosine are sometimes classified jointly as aromatic amino acids. In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224).

In one embodiment, where expression of two or more polypeptides is desired, the polynucleotide sequences encoding them can be separated by and IRES sequence as disclosed elsewhere herein.

Polypeptides contemplated in particular embodiments include fusion polypeptides. In particular embodiments, fusion polypeptides and polynucleotides encoding fusion polypeptides are provided. Fusion polypeptides and fusion proteins refer to a polypeptide having at least two, three, four, five, six, seven, eight, nine, or ten polypeptide segments.

In another embodiment, two or more polypeptides can be expressed as a fusion protein that comprises one or more self-cleaving polypeptide sequences as disclosed elsewhere herein.

In one embodiment, a fusion protein contemplated herein comprises one or more DNA binding domains and one or more nucleases, and one or more linker and/or self-cleaving polypeptides.

In one embodiment, a fusion protein contemplated herein comprises nuclease variant; a linker or self-cleaving peptide; and an end-processing enzyme including but not limited to a 5'-3' exonuclease, a 5'-3' alkaline exonuclease, and a 3'-5' exonuclease (e.g., Trex2).

Fusion polypeptides can comprise one or more polypeptide domains or segments including, but not limited to signal peptides, cell permeable peptide domains (CPP), DNA binding domains, nuclease domains, etc., epitope tags (e.g., maltose binding protein ("MBP"), glutathione S transferase (GST), HIS6, MYC, FLAG, V5, VSV-G, and HA), polypeptide linkers, and polypeptide cleavage signals. Fusion polypeptides are typically linked C-terminus to N-terminus, although they can also be linked C-terminus to C-terminus, N-terminus to N-terminus, or N-terminus to C-terminus. In particular embodiments, the polypeptides of the fusion protein can be in any order. Fusion polypeptides or fusion proteins can also include conservatively modified variants, polymorphic variants, alleles, mutants, subsequences, and interspecies homologs, so long as the desired activity of the fusion polypeptide is preserved. Fusion polypeptides may be produced by chemical synthetic methods or by chemical linkage between the two moieties or may generally be prepared using other standard techniques. Ligated DNA sequences comprising the fusion polypeptide are operably linked to suitable transcriptional or translational control elements as disclosed elsewhere herein.

Fusion polypeptides may optionally comprise a linker that can be used to link the one or more polypeptides or domains within a polypeptide. A peptide linker sequence may be employed to separate any two or more polypeptide components by a distance sufficient to ensure that each polypeptide folds into its appropriate secondary and tertiary structures so as to allow the polypeptide domains to exert their desired functions. Such a peptide linker sequence is incorporated into the fusion polypeptide using standard techniques in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39-46, 1985; Murphy et al., *Proc. Natl. Acad. Sci. USA* 83:8258-8262, 1986; U.S. Pat. Nos. 4,935,233 and 4,751,180. Linker sequences are not required when a particular fusion polypeptide segment contains non-essential N-terminal amino acid regions that can be used to separate the functional domains and prevent steric interference. Preferred linkers are typically flexible amino acid subsequences which are synthesized as part of a recombinant fusion protein. Linker polypeptides can be between 1 and 200 amino acids in length, between 1 and 100 amino acids in length, or between 1 and 50 amino acids in length, including all integer values in between.

Exemplary linkers include, but are not limited to the following amino acid sequences: glycine polymers (G)n; glycine-serine polymers (Gi-5S1-5)n, where n is an integer of at least one, two, three, four, or five; glycine-alanine polymers; alanine-serine polymers; GGG (SEQ ID NO: 24); DGGGS (SEQ ID NO: 25); TGEKP (SEQ ID NO: 26) (see e.g., Liu et al., *PNAS* 5525-5530 (1997)); GGRR (SEQ ID NO: 27) (Pomerantz et al. 1995, supra); (GGGGS)$_n$ wherein n=1, 2, 3, 4 or 5 (SEQ ID NO: 28) (Kim et al., *PNAS* 93, 1156-1160 (1996.); EGKSSGSGSESKVD (SEQ ID NO: 29) (Chaudhary et al., 1990, *Proc. Natl. Acad. Sci. U.S.A.* 87:1066-1070); KESGSVSSEQLAQFRSLD (SEQ ID NO: 30) (Bird et al., 1988, *Science* 242:423-426), GGRRGGGS (SEQ ID NO: 31); LRQRDGERP (SEQ ID NO: 32); LRQKDGGGSERP (SEQ ID NO: 33); LRQKD(GGGS)$_2$ERP (SEQ ID NO: 34).

Alternatively, flexible linkers can be rationally designed using a computer program capable of modeling both DNA-binding sites and the peptides themselves (Desjarlais & Berg, *PNAS* 90:2256-2260 (1993), *PNAS* 91:11099-11103 (1994) or by phage display methods.

Fusion polypeptides may further comprise a polypeptide cleavage signal between each of the polypeptide domains described herein or between an endogenous open reading frame and a polypeptide encoded by a donor repair template. In addition, a polypeptide cleavage site can be put into any linker peptide sequence. Exemplary polypeptide cleavage signals include polypeptide cleavage recognition sites such as protease cleavage sites, nuclease cleavage sites (e.g., rare restriction enzyme recognition sites, self-cleaving ribozyme recognition sites), and self-cleaving viral oligopeptides (see deFelipe and Ryan, 2004. *Traffic,* 5(8); 616-26).

Suitable protease cleavages sites and self-cleaving peptides are known to the skilled person (see, e.g., in Ryan et al., 1997. *J Gener. Virol.* 78, 699-722; Scymczak et al. (2004) Nature Biotech. 5, 589-594). Exemplary protease cleavage sites include, but are not limited to the cleavage sites of potyvirus NIa proteases (e.g., tobacco etch virus protease), potyvirus HC proteases, potyvirus P1 (P35) proteases, byovirus NIa proteases, byovirus RNA-2-encoded proteases, aphthovirus L proteases, enterovirus 2A proteases, rhinovirus 2A proteases, picorna 3C proteases, comovirus 24K proteases, nepovirus 24K proteases, RTSV (rice tungro spherical virus) 3C-like protease, PYVF (parsnip yellow fleck virus) 3C-like protease, heparin, thrombin, factor Xa and enterokinase. Due to its high cleavage stringency, TEV (tobacco etch virus) protease cleavage sites are preferred in one embodiment, e.g., EXXYXQ(G/S) (SEQ ID NO: 35), for example, ENLYFQG (SEQ ID NO: 36) and ENLYFQS (SEQ ID NO: 37), wherein X represents any amino acid (cleavage by TEV occurs between Q and G or Q and S).

In certain embodiments, the self-cleaving polypeptide site comprises a 2A or 2A-like site, sequence or domain (Donnelly et al., 2001. *J. Gen. Virol.* 82:1027-1041). In a particular embodiment, the viral 2A peptide is an aphthovirus 2A peptide, a potyvirus 2A peptide, or a cardiovirus 2A peptide.

In one embodiment, the viral 2A peptide is selected from the group consisting of: a foot-and-mouth disease virus (FMDV) (F2A) peptide, an equine rhinitis A virus (ERAV) (E2A) peptide, a Thosea asigna virus (TaV) (T2A) peptide, a porcine teschovirus-1 (PTV-1) (P2A) peptide, a Theilovirus 2A peptide, and an encephalomyocarditis virus 2A peptide.

Illustrative examples of 2A sites are provided in Table 2.

TABLE 2

Exemplary 2A sites include the following sequences:

| | |
|---|---|
| SEQ ID NO: 38 | GSGATNFSLLKQAGDVEENPGP |
| SEQ ID NO: 39 | ATNFSLLKQAGDVEENPGP |
| SEQ ID NO: 40 | LLKQAGDVEENPGP |
| SEQ ID NO: 41 | GSGEGRGSLLTCGDVEENPGP |
| SEQ ID NO: 42 | EGRGSLLTCGDVEENPGP |
| SEQ ID NO: 43 | LLTCGDVEENPGP |
| SEQ ID NO: 44 | GSGQCTNYALLKLAGDVESNPGP |
| SEQ ID NO: 45 | QCTNYALLKLAGDVESNPGP |
| SEQ ID NO: 46 | LLKLAGDVESNPGP |
| SEQ ID NO: 47 | GSGVKQTLNFDLLKLAGDVESNPGP |
| SEQ ID NO: 48 | VKQTLNFDLLKLAGDVESNPGP |
| SEQ ID NO: 49 | LLKLAGDVESNPGP |
| SEQ ID NO: 50 | LLNFDLLKLAGDVESNPGP |
| SEQ ID NO: 51 | TLNFDLLKLAGDVESNPGP |
| SEQ ID NO: 52 | LLKLAGDVESNPGP |
| SEQ ID NO: 53 | NFDLLKLAGDVESNPGP |
| SEQ ID NO: 54 | QLLNFDLLKLAGDVESNPGP |
| SEQ ID NO: 55 | APVKQTLNFDLLKLAGDVESNPGP |
| SEQ ID NO: 56 | VTELLYRMKRAETYCPRPLLAIHPTEARHKQKIVAPVKQT |
| SEQ ID NO: 57 | LNFDLLKLAGDVESNPGP |
| SEQ ID NO: 58 | LLAIHPTEARHKQKIVAPVKQTLNFDLLKLAGDVESNPGP |
| SEQ ID NO: 59 | EARHKQKIVAPVKQTLNFDLLKLAGDVESNPGP |

G. Polynucleotides

In particular embodiments, polynucleotides encoding one or more homing endonuclease variants, megaTALs, end-processing enzymes, and fusion polypeptides contemplated herein are provided. As used herein, the terms "polynucleotide" or "nucleic acid" refer to deoxyribonucleic acid (DNA), ribonucleic acid (RNA) and DNA/RNA hybrids. Polynucleotides may be single-stranded or double-stranded and either recombinant, synthetic, or isolated. Polynucleotides include, but are not limited to: pre-messenger RNA (pre-mRNA), messenger RNA (mRNA), RNA, short interfering RNA (siRNA), short hairpin RNA (shRNA), microRNA (miRNA), ribozymes, genomic RNA (gRNA), plus strand RNA (RNA(+)), minus strand RNA (RNA(−)), tracrRNA, crRNA, single guide RNA (sgRNA), synthetic RNA, synthetic mRNA, genomic DNA (gDNA), PCR amplified DNA, complementary DNA (cDNA), synthetic DNA, or recombinant DNA. In particular embodiments, polynucleotides include polynucleotide fragments that encode one or more biologically active polypeptide fragments or variants. Polynucleotides refer to a polymeric form of nucleotides of at least 5, at least 10, at least 15, at least 20, at least 25, at least 30, at least 40, at least 50, at least 100, at least 200, at least 300, at least 400, at least 500, at least 1000, at least 5000, at least 10000, or at least 15000 or more nucleotides in length, either ribonucleotides or deoxyribonucleotides or a modified form of either type of nucleotide, as well as all intermediate lengths. It will be readily understood that "intermediate lengths," in this context, means any length between the quoted values, such as 6, 7, 8, 9, etc., 101, 102, 103, etc.; 151, 152, 153, etc.; 201, 202, 203, etc. In particular embodiments, polynucleotides or variants have at least or about 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to a reference sequence.

In particular embodiments, polynucleotides may be codon-optimized. As used herein, the term "codon-optimized" refers to substituting codons in a polynucleotide encoding a polypeptide in order to increase the expression, stability and/or activity of the polypeptide. Factors that influence codon optimization include, but are not limited to one or more of (i) variation of codon biases between two or more organisms or genes or synthetically constructed bias tables, (ii) variation in the degree of codon bias within an organism, gene, or set of genes, (iii) systematic variation of codons including context, (iv) variation of codons according to their decoding tRNAs, (v) variation of codons according to GC %, either overall or in one position of the triplet, (vi) variation in degree of similarity to a reference sequence for example a naturally occurring sequence, (vii) variation in the codon frequency cutoff, (viii) structural properties of mRNAs transcribed from the DNA sequence, (ix) prior knowledge about the function of the DNA sequences upon which design of the codon substitution set is to be based, (x) systematic variation of codon sets for each amino acid, and/or (xi) isolated removal of spurious translation initiation sites.

As used herein the term "nucleotide" refers to a heterocyclic nitrogenous base in N-glycosidic linkage with a phosphorylated sugar. Nucleotides are understood to include natural bases, and a wide variety of art-recognized modified bases. Such bases are generally located at the 1' position of a nucleotide sugar moiety. Nucleotides generally comprise a base, sugar and a phosphate group. In ribonucleic acid (RNA), the sugar is a ribose, and in deoxyribonucleic acid (DNA) the sugar is a deoxyribose, i.e., a sugar lacking a hydroxyl group that is present in ribose. Exemplary natural nitrogenous bases include the purines, adenosine (A) and guanidine (G), and the pyrimidines, cytidine (C) and thymidine (T) (or in the context of RNA, uracil (U)). The C-1 atom of deoxyribose is bonded to N-1 of a pyrimidine or N-9 of a purine. Nucleotides are usually mono, di- or triphosphates. The nucleotides can be unmodified or modified at the sugar, phosphate and/or base moiety, (also referred to interchangeably as nucleotide analogs, nucleotide derivatives, modified nucleotides, non-natural nucleotides, and non-standard nucleotides; see for example, WO 92/07065 and WO 93/15187). Examples of modified nucleic acid bases are summarized by Limbach et al., (1994, *Nucleic Acids Res.* 22, 2183-2196).

A nucleotide may also be regarded as a phosphate ester of a nucleoside, with esterification occurring on the hydroxyl group attached to C-5 of the sugar. As used herein, the term "nucleoside" refers to a heterocyclic nitrogenous base in N-glycosidic linkage with a sugar. Nucleosides are recognized in the art to include natural bases, and also to include well known modified bases. Such bases are generally located at the 1' position of a nucleoside sugar moiety. Nucleosides generally comprise a base and sugar group. The nucleosides can be unmodified or modified at the sugar, and/or base moiety, (also referred to interchangeably as nucleoside analogs, nucleoside derivatives, modified nucleosides, non-natural nucleosides, or non-standard nucleosides). As also noted above, examples of modified nucleic acid bases are summarized by Limbach et al., (1994, *Nucleic Acids Res.* 22, 2183-2196).

Illustrative examples of polynucleotides include, but are not limited to polynucleotides encoding SEQ ID NOs: 1-10, and polynucleotide sequences set forth in SEQ ID NOs: 11-20.

In various illustrative embodiments, polynucleotides contemplated herein include, but are not limited to polynucleotides encoding homing endonuclease variants, megaTALs, end-processing enzymes, fusion polypeptides, and expression vectors, viral vectors, and transfer plasmids comprising polynucleotides contemplated herein.

As used herein, the terms "polynucleotide variant" and "variant" and the like refer to polynucleotides displaying substantial sequence identity with a reference polynucleotide sequence or polynucleotides that hybridize with a reference sequence under stringent conditions that are defined hereinafter. These terms also encompass polynucleotides that are distinguished from a reference polynucleotide by the addition, deletion, substitution, or modification of at least one nucleotide. Accordingly, the terms "polynucleotide variant" and "variant" include polynucleotides in which one or more nucleotides have been added or deleted, or modified, or replaced with different nucleotides. In this regard, it is well understood in the art that certain alterations inclusive of mutations, additions, deletions and substitutions can be made to a reference polynucleotide whereby the altered polynucleotide retains the biological function or activity of the reference polynucleotide.

Polynucleotide variants include polynucleotide fragments that encode biologically active polypeptide fragments or variants. As used herein, the term "polynucleotide fragment" refers to a polynucleotide fragment at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 150, 200, 250, 300, 350, 400, 450, 500, 550, 600, 650, 700, 750, 800, 850, 900, 950, 1000, 1100, 1200, 1300, 1400, 1500, 1600, 1700 or more nucleotides in length that encodes a polypeptide variant that retains at least 100%, at least 90%, at least 80%, at least 70%, at least 60%, at least 50%, at least 40%, at least 30%, at least 20%, at least 10%, or at least 5% of the naturally occurring polypeptide activity. Polynucleotide fragments refer to a polynucleotide that encodes a polypeptide that has an amino-terminal deletion, a carboxyl-terminal deletion, and/or an internal deletion or substitution of one or more amino acids of a naturally-occurring or recombinantly-produced polypeptide.

In one embodiment, a polynucleotide comprises a nucleotide sequence that hybridizes to a target nucleic acid sequence under stringent conditions. To hybridize under "stringent conditions" describes hybridization protocols in which nucleotide sequences at least 60% identical to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

The recitations "sequence identity" or, for example, comprising a "sequence 50% identical to," as used herein, refer to the extent that sequences are identical on a nucleotide-by-nucleotide basis or an amino acid-by-amino acid basis over a window of comparison. Thus, a "percentage of sequence identity" may be calculated by comparing two optimally aligned sequences over the window of comparison, determining the number of positions at which the identical nucleic acid base (e.g., A, T, C, G, I) or the identical amino acid residue (e.g., Ala, Pro, Ser, Thr, Gly, Val, Leu, Ile, Phe, Tyr, Trp, Lys, Arg, His, Asp, Glu, Asn, Gln, Cys and Met) occurs in both sequences to yield the number of matched positions, dividing the number of matched positions by the total number of positions in the window of comparison (i.e., the window size), and multiplying the result by 100 to yield the percentage of sequence identity. Included are nucleotides and polypeptides having at least about 50%, 55%, 60%, 65%, 70%, 75%, 80%, 85%, 90%, 95%, 96%, 97%, 98%, 99% or 100% sequence identity to any of the reference sequences described herein, typically where the polypeptide variant maintains at least one biological activity of the reference polypeptide.

Terms used to describe sequence relationships between two or more polynucleotides or polypeptides include "reference sequence," "comparison window," "sequence identity," "percentage of sequence identity," and "substantial identity". A "reference sequence" is at least 12 but frequently 15 to 18 and often at least 25 monomer units, inclusive of nucleotides and amino acid residues, in length. Because two polynucleotides may each comprise (1) a sequence (i.e., only a portion of the complete polynucleotide sequence) that is similar between the two polynucleotides, and (2) a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window" refers to a conceptual segment of at least 6 contiguous positions, usually about 50 to about 100, more usually about 100 to about 150 in which a sequence is compared to a reference sequence of the same number of contiguous positions after the two sequences are optimally aligned. The comparison window may comprise additions or deletions (i.e., gaps) of about 20% or less as compared to the reference sequence (which does not comprise additions or deletions) for optimal alignment of the two sequences. Optimal alignment of sequences for aligning a comparison window may be conducted by computerized implementations of algorithms (GAP, BESTFIT, FASTA, and TFASTA in the Wisconsin Genetics Software Package Release 7.0, Genetics Computer Group, 575 Science Drive Madison, Wis., USA) or by inspection and the best alignment (i.e., resulting in the highest percentage homology over the comparison window) generated by any of the various methods selected. Reference also may be made to the BLAST family of programs as for example disclosed by Altschul et al., 1997, *Nucl. Acids Res.* 25:3389. A detailed discussion of sequence analysis can be found in Unit 19.3 of Ausubel et al., *Current Protocols in Molecular Biology*, John Wiley & Sons Inc., 1994-1998, Chapter 15.

An "isolated polynucleotide," as used herein, refers to a polynucleotide that has been purified from the sequences which flank it in a naturally-occurring state, e.g., a DNA fragment that has been removed from the sequences that are normally adjacent to the fragment. In particular embodiments, an "isolated polynucleotide" refers to a complementary DNA (cDNA), a recombinant polynucleotide, a synthetic polynucleotide, or other polynucleotide that does not exist in nature and/or that has been made by the hand of man.

In various embodiments, a polynucleotide comprises an mRNA encoding a polypeptide contemplated herein including, but not limited to, a homing endonuclease variant, a megaTAL, and an end-processing enzyme. In certain embodiments, the mRNA comprises a cap, one or more nucleotides, and a poly(A) tail.

As used herein, the terms "5' cap" or "5' cap structure" or "5' cap moiety" refer to a chemical modification, which has been incorporated at the 5' end of an mRNA. The 5' cap is involved in nuclear export, mRNA stability, and translation.

In particular embodiments, an mRNA contemplated herein comprises a 5' cap comprising a 5'-ppp-5'-triphosphate linkage between a terminal guanosine cap residue and the 5'-terminal transcribed sense nucleotide of the mRNA molecule. This 5'-guanylate cap may then be methylated to generate an N7-methyl-guanylate residue.

Illustrative examples of 5' cap suitable for use in particular embodiments of the mRNA polynucleotides contemplated herein include, but are not limited to: unmethylated 5' cap analogs, e.g., G(5')ppp(5')G, G(5')ppp(5')C, G(5')ppp(5')A; methylated 5' cap analogs, e.g., m$^7$G(5')ppp(5')G, m$^7$G(5')ppp(5')C, and m$^7$G(5')ppp(5')A; dimethylated 5' cap analogs, e.g., m$^{2,7}$G(5')ppp(5')G, m$^{2,7}$G(5')ppp(5')C, and m$^{2,7}$G(5')ppp(5')A; trimethylated 5' cap analogs, e.g., m$^{2,2,7}$G(5')ppp(5')G, m$^{2,2,7}$G(5')ppp(5')C, and m$^{2,2,7}$G(5')ppp(5')A; dimethylated symmetrical 5' cap analogs, e.g., m$^7$G(5')pppm$^7$(5')G, m$^7$G(5')pppm$^7$(5')C, and m$^7$G(5')pppm$^7$(5')A; and anti-reverse 5' cap analogs, e.g., Anti-Reverse Cap Analog (ARCA) cap, designated 3'O-Me-m$^7$G(5')ppp(5')G, 2'O-Me-m$^7$G(5')ppp(5')G, 2'O-Me-m$^7$G(5')ppp(5')C, 2'O-Me-m$^7$G(5')ppp(5')A, m$^7$2'd(5')ppp(5')G, m$^7$2'd(5')ppp(5')C, m$^7$2'd(5')ppp(5')A, 3'O-Me-m$^7$G(5')ppp(5')C, 3'O-Me-m$^7$G(5')ppp(5')A, m$^7$3'd(5')ppp(5')G, m$^7$3'd(5')ppp(5')C, m$^7$3'd(5')ppp(5')A and their tetraphosphate derivatives) (see, e.g., Jemielity et al., RNA, 9: 1108-1122 (2003)).

In particular embodiments, mRNAs comprise a 5' cap that is a 7-methyl guanylate ("m$^7$G") linked via a triphosphate bridge to the 5'-end of the first transcribed nucleotide, resulting in m$^7$G(5')ppp(5')N, where N is any nucleoside.

In some embodiments, mRNAs comprise a 5' cap wherein the cap is a Cap0 structure (Cap0 structures lack a 2'-O-methyl residue of the ribose attached to bases 1 and 2), a Cap1 structure (Cap1 structures have a 2'-O-methyl residue at base 2), or a Cap2 structure (Cap2 structures have a 2'-O-methyl residue attached to both bases 2 and 3).

In one embodiment, an mRNA comprises a m$^7$G(5')ppp(5')G cap.

In one embodiment, an mRNA comprises an ARCA cap.

In particular embodiments, an mRNA contemplated herein comprises one or more modified nucleosides.

In one embodiment, an mRNA comprises one or more modified nucleosides selected from the group consisting of pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyl-adenine, 2-methylthio-adenine, 2-methoxy-adenine, inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methyl-guanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more modified nucleosides selected from the group consisting of: pseudouridine, pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine.

In one embodiment, an mRNA comprises one or more modified nucleosides selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine.

In one embodiment, an mRNA comprises one or more modified nucleosides selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine.

In one embodiment, an mRNA comprises one or more modified nucleosides selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methyl-inosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In one embodiment, an mRNA comprises one or more pseudouridines, one or more 5-methyl-cytosines, and/or one or more 5-methyl-cytidines.

In one embodiment, an mRNA comprises one or more pseudouridines.

In one embodiment, an mRNA comprises one or more 5-methyl-cytidines.

In one embodiment, an mRNA comprises one or more 5-methyl-cytosines.

In particular embodiments, an mRNA contemplated herein comprises a poly(A) tail to help protect the mRNA from exonuclease degradation, stabilize the mRNA, and facilitate translation. In certain embodiments, an mRNA comprises a 3' poly(A) tail structure.

In particular embodiments, the length of the poly(A) tail is at least about 10, 25, 50, 75, 100, 150, 200, 250, 300, 350, 400, 450, or at least about 500 or more adenine nucleotides or any intervening number of adenine nucleotides. In particular embodiments, the length of the poly(A) tail is at least about 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, or 275 or more adenine nucleotides.

In particular embodiments, the length of the poly(A) tail is about 10 to about 500 adenine nucleotides, about 50 to about 500 adenine nucleotides, about 100 to about 500 adenine nucleotides, about 150 to about 500 adenine nucleotides, about 200 to about 500 adenine nucleotides, about 250 to about 500 adenine nucleotides, about 300 to about 500 adenine nucleotides, about 50 to about 450 adenine nucleotides, about 50 to about 400 adenine nucleotides, about 50 to about 350 adenine nucleotides, about 100 to about 500 adenine nucleotides, about 100 to about 450 adenine nucleotides, about 100 to about 400 adenine nucleotides, about 100 to about 350 adenine nucleotides, about 100 to about 300 adenine nucleotides, about 150 to about 500 adenine nucleotides, about 150 to about 450 adenine nucleotides, about 150 to about 400 adenine nucleotides, about 150 to about 350 adenine nucleotides, about 150 to about 300 adenine nucleotides, about 150 to about 250 adenine nucleotides, about 150 to about 200 adenine nucleotides, about 200 to about 500 adenine nucleotides, about 200 to about 450 adenine nucleotides, about 200 to about 400 adenine nucleotides, about 200 to about 350 adenine nucleotides, about 200 to about 300 adenine nucleotides, about 250 to about 500 adenine nucleotides, about 250 to about 450 adenine nucleotides, about 250 to about 400 adenine nucleotides, about 250 to about 350 adenine nucleotides, or about 250 to about 300 adenine nucleotides or any intervening range of adenine nucleotides.

Terms that describe the orientation of polynucleotides include: 5' (normally the end of the polynucleotide having a free phosphate group) and 3' (normally the end of the polynucleotide having a free hydroxyl (OH) group). Polynucleotide sequences can be annotated in the 5' to 3' orientation or the 3' to 5' orientation. For DNA and mRNA, the 5' to 3' strand is designated the "sense," "plus," or "coding" strand because its sequence is identical to the sequence of the pre-messenger (pre-mRNA) [except for uracil (U) in RNA, instead of thymine (T) in DNA]. For DNA and mRNA, the complementary 3' to 5' strand which is the strand transcribed by the RNA polymerase is designated as "template," "antisense," "minus," or "non-coding" strand. As used herein, the term "reverse orientation" refers to a 5' to 3' sequence written in the 3' to 5' orientation or a 3' to 5' sequence written in the 5' to 3' orientation.

The terms "complementary" and "complementarity" refer to polynucleotides (i.e., a sequence of nucleotides) related by the base-pairing rules. For example, the complementary strand of the DNA sequence 5' A G T C A T G 3' is 3' T C A G T A C 5'. The latter sequence is often written as the reverse complement with the 5' end on the left and the 3' end on the right, 5' C A T G A C T 3'. A sequence that is equal to its reverse complement is said to be a palindromic sequence. Complementarity can be "partial," in which only some of the nucleic acids' bases are matched according to the base pairing rules. Or, there can be "complete" or "total" complementarity between the nucleic acids.

The term "nucleic acid cassette" or "expression cassette" as used herein refers to genetic sequences within the vector which can express an RNA, and subsequently a polypeptide. In one embodiment, the nucleic acid cassette contains a gene(s)-of-interest, e.g., a polynucleotide(s)-of-interest. In another embodiment, the nucleic acid cassette contains one or more expression control sequences, e.g., a promoter, enhancer, poly(A) sequence, and a gene(s)-of-interest, e.g., a polynucleotide(s)-of-interest. Vectors may comprise 1, 2, 3, 4, 5, 6, 7, 8, 9 or 10 or more nucleic acid cassettes. The nucleic acid cassette is positionally and sequentially oriented within the vector such that the nucleic acid in the cassette can be transcribed into RNA, and when necessary, translated into a protein or a polypeptide, undergo appropriate post-translational modifications required for activity in the transformed cell, and be translocated to the appropriate compartment for biological activity by targeting to appropriate intracellular compartments or secretion into extracellular compartments. Preferably, the cassette has its 3' and 5' ends adapted for ready insertion into a vector, e.g., it has restriction endonuclease sites at each end. In a preferred embodiment, the nucleic acid cassette contains the sequence of a therapeutic gene used to treat, prevent, or ameliorate a genetic disorder. The cassette can be removed and inserted into a plasmid or viral vector as a single unit.

Polynucleotides include polynucleotide(s)-of-interest. As used herein, the term "polynucleotide-of-interest" refers to a polynucleotide encoding a polypeptide or fusion polypeptide or a polynucleotide that serves as a template for the transcription of an inhibitory polynucleotide, as contemplated herein.

Moreover, it will be appreciated by those of ordinary skill in the art that, as a result of the degeneracy of the genetic code, there are many nucleotide sequences that may encode a polypeptide, or fragment of variant thereof, as contemplated herein. Some of these polynucleotides bear minimal homology to the nucleotide sequence of any native gene. Nonetheless, polynucleotides that vary due to differences in codon usage are specifically contemplated in particular embodiments, for example polynucleotides that are optimized for human and/or primate codon selection. In one embodiment, polynucleotides comprising particular allelic sequences are provided. Alleles are endogenous polynucleotide sequences that are altered as a result of one or more mutations, such as deletions, additions and/or substitutions of nucleotides.

In a certain embodiment, a polynucleotide-of-interest comprises a donor repair template.

In a certain embodiment, a polynucleotide-of-interest comprises an inhibitory polynucleotide including, but not limited to, an siRNA, an miRNA, an shRNA, a ribozyme or another inhibitory RNA.

In one embodiment, a donor repair template encoding an inhibitory RNA comprises one or more regulatory sequences, such as, for example, a strong constitutive pol III, e.g., human or mouse U6 snRNA promoter, the human and mouse H1 RNA promoter, or the human tRNA-val promoter, or a strong constitutive pol II promoter, as described elsewhere herein.

The polynucleotides contemplated in particular embodiments, regardless of the length of the coding sequence itself, may be combined with other DNA sequences, such as promoters and/or enhancers, untranslated regions (UTRs), Kozak sequences, polyadenylation signals, additional restriction enzyme sites, multiple cloning sites, internal ribosomal entry sites (IRES), recombinase recognition sites (e.g., LoxP, FRT, and Att sites), termination codons, transcriptional termination signals, post-transcription response elements, and polynucleotides encoding self-cleaving polypeptides, epitope tags, as disclosed elsewhere herein or as known in the art, such that their overall length may vary considerably. It is therefore contemplated in particular embodiments that a polynucleotide fragment of almost any length may be employed, with the total length preferably being limited by the ease of preparation and use in the intended recombinant DNA protocol.

Polynucleotides can be prepared, manipulated, expressed and/or delivered using any of a variety of well-established techniques known and available in the art. In order to express a desired polypeptide, a nucleotide sequence encoding the polypeptide, can be inserted into appropriate vector. A desired polypeptide can also be expressed by delivering an mRNA encoding the polypeptide into the cell.

Illustrative examples of vectors include, but are not limited to plasmid, autonomously replicating sequences, and transposable elements, e.g., Sleeping Beauty, PiggyBac.

Additional illustrative examples of vectors include, without limitation, plasmids, phagemids, cosmids, artificial chromosomes such as yeast artificial chromosome (YAC), bacterial artificial chromosome (BAC), or P1-derived artificial chromosome (PAC), bacteriophages such as lambda phage or M13 phage, and animal viruses.

Illustrative examples of viruses useful as vectors include, without limitation, retrovirus (including lentivirus), adenovirus, adeno-associated virus, herpesvirus (e.g., herpes simplex virus), poxvirus, baculovirus, papillomavirus, and papovavirus (e.g., SV40).

Illustrative examples of expression vectors include, but are not limited to pClneo vectors (Promega) for expression in mammalian cells; pLenti4/V5-DEST™, pLenti6/V5-DEST™, and pLenti6.2/V5-GW/lacZ (Invitrogen) for lentivirus-mediated gene transfer and expression in mammalian cells. In particular embodiments, coding sequences of polypeptides disclosed herein can be ligated into such expression vectors for the expression of the polypeptides in mammalian cells.

In particular embodiments, the vector is an episomal vector or a vector that is maintained extrachromosomally. As used herein, the term "episomal" refers to a vector that is able to replicate without integration into host's chromosomal DNA and without gradual loss from a dividing host cell also meaning that said vector replicates extrachromosomally or episomally.

"Expression control sequences," "control elements," or "regulatory sequences" present in an expression vector are those non-translated regions of the vector-origin of replication, selection cassettes, promoters, enhancers, translation initiation signals (Shine Dalgarno sequence or Kozak sequence) introns, post-transcriptional regulatory elements, a polyadenylation sequence, 5' and 3' untranslated regions- which interact with host cellular proteins to carry out transcription and translation. Such elements may vary in their strength and specificity. Depending on the vector system and host utilized, any number of suitable transcription and translation elements, including ubiquitous promoters and inducible promoters may be used.

In particular embodiments, a polynucleotide comprises a vector, including but not limited to expression vectors and viral vectors. A vector may comprise one or more exogenous, endogenous, or heterologous control sequences such as promoters and/or enhancers. An "endogenous control sequence" is one which is naturally linked with a given gene in the genome. An "exogenous control sequence" is one which is placed in juxtaposition to a gene by means of genetic manipulation (i.e., molecular biological techniques) such that transcription of that gene is directed by the linked enhancer/promoter. A "heterologous control sequence" is an exogenous sequence that is from a different species than the cell being genetically manipulated. A "synthetic" control sequence may comprise elements of one more endogenous and/or exogenous sequences, and/or sequences determined in vitro or in silico that provide optimal promoter and/or enhancer activity for the particular therapy.

The term "promoter" as used herein refers to a recognition site of a polynucleotide (DNA or RNA) to which an RNA polymerase binds. An RNA polymerase initiates and transcribes polynucleotides operably linked to the promoter. In particular embodiments, promoters operative in mammalian cells comprise an AT-rich region located approximately 25 to 30 bases upstream from the site where transcription is initiated and/or another sequence found 70 to 80 bases upstream from the start of transcription, a CNCAAT region where N may be any nucleotide.

The term "enhancer" refers to a segment of DNA which contains sequences capable of providing enhanced transcription and in some instances can function independent of their orientation relative to another control sequence. An enhancer can function cooperatively or additively with promoters and/or other enhancer elements. The term "promoter/enhancer" refers to a segment of DNA which contains sequences capable of providing both promoter and enhancer functions.

The term "operably linked", refers to a juxtaposition wherein the components described are in a relationship permitting them to function in their intended manner. In one embodiment, the term refers to a functional linkage between a nucleic acid expression control sequence (such as a promoter, and/or enhancer) and a second polynucleotide sequence, e.g., a polynucleotide-of-interest, wherein the expression control sequence directs transcription of the nucleic acid corresponding to the second sequence.

As used herein, the term "constitutive expression control sequence" refers to a promoter, enhancer, or promoter/enhancer that continually or continuously allows for transcription of an operably linked sequence. A constitutive expression control sequence may be a "ubiquitous" promoter, enhancer, or promoter/enhancer that allows expression in a wide variety of cell and tissue types or a "cell specific," "cell type specific," "cell lineage specific," or "tissue specific" promoter, enhancer, or promoter/enhancer that allows expression in a restricted variety of cell and tissue types, respectively.

Illustrative ubiquitous expression control sequences suitable for use in particular embodiments include, but are not limited to, a cytomegalovirus (CMV) immediate early promoter, a viral simian virus 40 (SV40) (e.g., early or late), a Moloney murine leukemia virus (MoMLV) LTR promoter, a Rous sarcoma virus (RSV) LTR, a herpes simplex virus (HSV) (thymidine kinase) promoter, H5, P7.5, and P11 promoters from vaccinia virus, a short elongation factor 1-alpha (EF1a-short) promoter, a long elongation factor 1-alpha (EF1a-long) promoter, early growth response 1 (EGR1), ferritin H (FerH), ferritin L (FerL), Glyceraldehyde 3-phosphate dehydrogenase (GAPDH), eukaryotic translation initiation factor 4A1 (EIF4A1), heat shock 70 kDa protein 5 (HSPA5), heat shock protein 90 kDa beta, member 1 (HSP90B1), heat shock protein 70 kDa (HSP70), β-kinesin (β-KIN), the human ROSA 26 locus (Irions et al., *Nature Biotechnology* 25, 1477-1482 (2007)), a Ubiquitin C promoter (UBC), a phosphoglycerate kinase-1 (PGK) promoter, a cytomegalovirus enhancer/chicken β-actin (CAG) promoter, a β-actin promoter and a myeloproliferative sarcoma virus enhancer, negative control region deleted, dl587rev primer-binding site substituted U3 (MNDU3) promoter (Haas et al., 2003. *Journal of Virology.* 77(17):9439-9450).

In a particular embodiment, it may be desirable to use a cell, cell type, cell lineage or tissue specific expression control sequence to achieve cell type specific, lineage specific, or tissue specific expression of a desired polynucleotide sequence (e.g., to express a particular nucleic acid encoding a polypeptide in only a subset of cell types, cell lineages, or tissues or during specific stages of development).

As used herein, "conditional expression" may refer to any type of conditional expression including, but not limited to, inducible expression; repressible expression; expression in cells or tissues having a particular physiological, biological, or disease state, etc. This definition is not intended to exclude cell type or tissue specific expression. Certain embodiments provide conditional expression of a polynucleotide-of-interest, e.g., expression is controlled by subjecting a cell, tissue, organism, etc., to a treatment or condition that causes the polynucleotide to be expressed or that causes an increase or decrease in expression of the polynucleotide encoded by the polynucleotide-of-interest.

Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, *Gene*, 323:67), the cumate inducible gene switch (WO 2002/088346), tetracycline-dependent regulatory systems, etc.

Conditional expression can also be achieved by using a site-specific DNA recombinase. According to certain embodiments, polynucleotides comprises at least one (typically two) site(s) for recombination mediated by a site-specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, six, seven, eight, nine, ten or more.), which may be wild-type proteins (see Landy, Current Opinion in Biotechnology 3:699-707 (1993)), or mutants, derivatives (e.g., fusion proteins containing the recombination protein sequences or fragments thereof), fragments, and variants thereof. Illustrative examples of recombinases suitable for use in particular embodiments include, but are not limited to: Cre, Int, IF, Xis, Flp, Fis, Hin, Gin, ΦC31, Cin, Tn3 resolvase, TndX, XerC, XerD, TnpX, Hjc, Gin, SpCCE1, and ParA.

The polynucleotides may comprise one or more recombination sites for any of a wide variety of site specific recombinases. It is to be understood that the target site for a site specific recombinase is in addition to any site(s) required for integration of a vector, e.g., a retroviral vector or lentiviral vector. As used herein, the terms "recombination sequence," "recombination site," or "site specific recombination site" refer to a particular nucleic acid sequence to which a recombinase recognizes and binds.

For example, one recombination site for Cre recombinase is loxP which is a 34 base pair sequence comprising two 13 base pair inverted repeats (serving as the recombinase binding sites) flanking an 8 base pair core sequence (see FIG. 1 of Sauer, B., *Current Opinion in Biotechnology* 5:521-527 (1994)). Other exemplary loxP sites include, but are not limited to: lox511 (Hoess et al., 1996; Bethke and Sauer, 1997), lox5171 (Lee and Saito, 1998), lox2272 (Lee and Saito, 1998), m2 (Langer et al., 2002), lox71 (Albert et al., 1995), and lox66 (Albert et al., 1995).

Suitable recognition sites for the FLP recombinase include, but are not limited to: FRT (McLeod, et al., 1996), $F_1$, $F_2$, $F_3$ (Schlake and Bode, 1994), $F_4$, $F_5$ (Schlake and Bode, 1994), FRT(LE) (Senecoff et al., 1988), FRT(RE) (Senecoff et al., 1988).

Other examples of recognition sequences are the attB, attP, attL, and attR sequences, which are recognized by the recombinase enzyme λ Integrase, e.g., phi-c31. The φC31 SSR mediates recombination only between the heterotypic sites attB (34 bp in length) and attP (39 bp in length) (Groth et al., 2000). attB and attP, named for the attachment sites for the phage integrase on the bacterial and phage genomes, respectively, both contain imperfect inverted repeats that are likely bound by φC31 homodimers (Groth et al., 2000). The product sites, attL and attR, are effectively inert to further φC31-mediated recombination (Belteki et al., 2003), making the reaction irreversible. For catalyzing insertions, it has been found that attB-bearing DNA inserts into a genomic attP site more readily than an attP site into a genomic attB site (Thyagarajan et al., 2001; Belteki et al., 2003). Thus, typical strategies position by homologous recombination an attP-bearing "docking site" into a defined locus, which is then partnered with an attB-bearing incoming sequence for insertion.

In one embodiment, a polynucleotide contemplated herein comprises a donor repair template polynucleotide flanked by a pair of recombinase recognition sites. In particular embodiments, the repair template polynucleotide is flanked by LoxP sites, FRT sites, or att sites.

In particular embodiments, polynucleotides contemplated herein, include one or more polynucleotides-of-interest that encode one or more polypeptides. In particular embodiments, to achieve efficient translation of each of the plurality of polypeptides, the polynucleotide sequences can be separated by one or more IRES sequences or polynucleotide sequences encoding self-cleaving polypeptides.

As used herein, an "internal ribosome entry site" or "IRES" refers to an element that promotes direct internal ribosome entry to the initiation codon, such as ATG, of a cistron (a protein encoding region), thereby leading to the cap-independent translation of the gene. See, e.g., Jackson et al., 1990. *Trends Biochem Sci* 15(12):477-83) and Jackson and Kaminski. 1995. *RNA* 1(10):985-1000. Examples of IRES generally employed by those of skill in the art include those described in U.S. Pat. No. 6,692,736. Further examples of "IRES" known in the art include, but are not limited to IRES obtainable from picornavirus (Jackson et al., 1990) and IRES obtainable from viral or cellular mRNA sources, such as for example, immunoglobulin heavy-chain binding protein (BiP), the vascular endothelial growth factor (VEGF) (Huez et al. 1998. *Mol. Cell. Biol.* 18(11):6178-6190), the fibroblast growth factor 2 (FGF-2), and insulin-like growth factor (IGFII), the translational initiation factor eIF4G and yeast transcription factors TFIID and HAP4, the encephelomycarditis virus (EMCV) which is commercially available from Novagen (Duke et al., 1992. J. Virol 66(3): 1602-9) and the VEGF IRES (Huez et al., 1998. Mol Cell Biol 18(11):6178-90). IRES have also been reported in viral genomes of Picornaviridae, Dicistroviridae and Flaviviridae species and in HCV, Friend murine leukemia virus (FrMLV) and Moloney murine leukemia virus (MMLV).

In one embodiment, the IRES used in polynucleotides contemplated herein is an EMCV IRES.

In particular embodiments, the polynucleotides comprise polynucleotides that have a consensus Kozak sequence and that encode a desired polypeptide. As used herein, the term "Kozak sequence" refers to a short nucleotide sequence that greatly facilitates the initial binding of mRNA to the small subunit of the ribosome and increases translation. The consensus Kozak sequence is (GCC)RCCATGG (SEQ ID NO:60), where R is a purine (A or G) (Kozak, 1986. Cell. 44(2):283-92, and Kozak, 1987. *Nucleic Acids Res.* 15(20): 8125-48).

Elements directing the efficient termination and polyadenylation of the heterologous nucleic acid transcripts increases heterologous gene expression. Transcription termination signals are generally found downstream of the polyadenylation signal. In particular embodiments, vectors comprise a polyadenylation sequence 3' of a polynucleotide encoding a polypeptide to be expressed. The term "polyA site" or "polyA sequence" as used herein denotes a DNA sequence which directs both the termination and polyadenylation of the nascent RNA transcript by RNA polymerase II. Polyadenylation sequences can promote mRNA stability by addition of a polyA tail to the 3' end of the coding sequence and thus, contribute to increased translational efficiency. Cleavage and polyadenylation is directed by a poly(A) sequence in the RNA. The core poly(A) sequence for mammalian pre-mRNAs has two recognition elements flanking a cleavage-polyadenylation site. Typically, an almost invariant AAUAAA hexamer lies 20-50 nucleotides upstream of a more variable element rich in U or GU residues. Cleavage of the nascent transcript occurs between these two elements and is coupled to the addition of up to 250 adenosines to the 5' cleavage product. In particular embodiments, the core poly(A) sequence is an ideal polyA sequence (e.g., AATAAA, ATTAAA, AGTAAA). In particular embodiments, the poly(A) sequence is an SV40 polyA sequence, a bovine growth hormone polyA sequence (BGHpA), a rabbit β-globin polyA sequence (rβgpA), variants thereof, or another suitable heterologous or endogenous polyA sequence known in the art.

In some embodiments, a polynucleotide or cell harboring the polynucleotide utilizes a suicide gene, including an inducible suicide gene to reduce the risk of direct toxicity and/or uncontrolled proliferation. In specific embodiments, the suicide gene is not immunogenic to the host harboring the polynucleotide or cell. A certain example of a suicide gene that may be used is caspase-9 or caspase-8 or cytosine deaminase. Caspase-9 can be activated using a specific chemical inducer of dimerization (CID).

In certain embodiments, polynucleotides comprise gene segments that cause the genetically modified cells contemplated herein to be susceptible to negative selection in vivo. "Negative selection" refers to an infused cell that can be eliminated as a result of a change in the in vivo condition of the individual. The negative selectable phenotype may result from the insertion of a gene that confers sensitivity to an administered agent, for example, a compound. Negative selection genes are known in the art, and include, but are not limited to: the herpes simplex virus type I thymidine kinase (HSV-I TK) gene which confers ganciclovir sensitivity; the cellular hypoxanthine phosphribosyltransferase (HPRT) gene, the cellular adenine phosphoribosyltransferase (APRT) gene, and bacterial cytosine deaminase.

In some embodiments, genetically modified cells comprise a polynucleotide further comprising a positive marker that enables the selection of cells of the negative selectable phenotype in vitro. The positive selectable marker may be a gene, which upon being introduced into the host cell, expresses a dominant phenotype permitting positive selection of cells carrying the gene. Genes of this type are known in the art, and include, but are not limited to hygromycin-B phosphotransferase gene (hph) which confers resistance to hygromycin B, the amino glycoside phosphotransferase gene (neo or aph) from Tn5 which codes for resistance to the antibiotic G418, the dihydrofolate reductase (DHFR) gene, the adenosine deaminase gene (ADA), and the multi-drug resistance (MDR) gene.

In one embodiment, a positive selectable marker and a negative selectable marker are linked such that loss of the negative selectable marker necessarily also is accompanied by loss of the positive selectable marker. In a particular embodiment, the positive and negative selectable markers are fused so that loss of one obligatorily leads to loss of the other. An example of a fused polynucleotide that yields as an expression product a polypeptide that confers both the desired positive and negative selection features described above is a hygromycin phosphotransferase thymidine kinase fusion gene (HyTK). Expression of this gene yields a polypeptide that confers hygromycin B resistance for positive selection in vitro, and ganciclovir sensitivity for negative selection in vivo. See also the publications of PCT US91/08442 and PCT/US94/05601, by S. D. Lupton, describing the use of bifunctional selectable fusion genes derived from fusing a dominant positive selectable markers with negative selectable markers.

Preferred positive selectable markers are derived from genes selected from the group consisting of hph, nco, and gpt, and preferred negative selectable markers are derived from genes selected from the group consisting of cytosine deaminase, HSV-I TK, VZV TK, HPRT, APRT and gpt. Exemplary bifunctional selectable fusion genes contemplated in particular embodiments include, but are not limited to genes wherein the positive selectable marker is derived from hph or neo, and the negative selectable marker is derived from cytosine deaminase or a TK gene or selectable marker.

In particular embodiments, polynucleotides encoding one or more nuclease variants, megaTALs, end-processing enzymes, or fusion polypeptides may be introduced into hepatic cells, by both non-viral and viral methods. In particular embodiments, delivery of one or more polynucleotides encoding nucleases and/or donor repair templates may be provided by the same method or by different methods, and/or by the same vector or by different vectors.

The term "vector" is used herein to refer to a nucleic acid molecule capable transferring or transporting another nucleic acid molecule. The transferred nucleic acid is generally linked to, e.g., inserted into, the vector nucleic acid molecule. A vector may include sequences that direct autonomous replication in a cell, or may include sequences sufficient to allow integration into host cell DNA. In particular embodiments, non-viral vectors are used to deliver one or more polynucleotides contemplated herein to a T cell.

Illustrative examples of non-viral vectors include, but are not limited to plasmids (e.g., DNA plasmids or RNA plasmids), transposons, cosmids, and bacterial artificial chromosomes.

Illustrative methods of non-viral delivery of polynucleotides contemplated in particular embodiments include, but are not limited to: electroporation, sonoporation, lipofection, microinjection, biolistics, virosomes, liposomes, immunoliposomes, nanoparticles, polycation or lipid:nucleic acid conjugates, naked DNA, artificial virions, DEAE-dextran-mediated transfer, gene gun, and heat-shock.

Illustrative examples of polynucleotide delivery systems suitable for use in particular include, but are not limited to those provided by Amaxa Biosystems, Maxcyte, Inc., BTX Molecular Delivery Systems, and Copernicus Therapeutics Inc. Lipofection reagents are sold commercially (e.g., Transfectam™ and Lipofectin™). Cationic and neutral lipids that are suitable for efficient receptor-recognition lipofection of polynucleotides have been described in the literature. See e.g., Liu et al. (2003) *Gene Therapy.* 10:180-187; and Balazs et al. (2011) *Journal of Drug Delivery.* 2011:1-12. Antibody-targeted, bacterially derived, non-living nanocell-based delivery is also contemplated in particular embodiments.

Viral vectors comprising polynucleotides contemplated in particular embodiments can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., liver cells) or induced pluripotent stem cells, followed by reimplantation of the cells into a patient.

In one embodiment, viral vectors comprising nuclease variants and/or donor repair templates are administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Illustrative examples of viral vector systems suitable for use in particular embodiments contemplated herein include, but are not limited to adeno-associated virus (AAV), retrovirus, herpes simplex virus, adenovirus, and vaccinia virus vectors.

In various embodiments, one or more polynucleotides encoding a nuclease variant and/or donor repair template are introduced into a hepatic cell, by transducing the cell with a recombinant adeno-associated virus (rAAV), comprising the one or more polynucleotides.

AAV is a small (~26 nm) replication-defective, primarily episomal, non-enveloped virus. AAV can infect both dividing and non-dividing cells and may incorporate its genome into that of the host cell. Recombinant AAV (rAAV) are typically composed of, at a minimum, a transgene and its regulatory sequences, and 5' and 3' AAV inverted terminal repeats (ITRs). The ITR sequences are about 145 bp in length. In particular embodiments, the rAAV comprises ITRs and capsid sequences isolated from AAV1, AAV2, AAV3, AAV4, AAV5, AAV6, AAV7, AAV8, AAV9, or AAV10.

In some embodiments, a chimeric rAAV is used the ITR sequences are isolated from one AAV serotype and the capsid sequences are isolated from a different AAV serotype. For example, a rAAV with ITR sequences derived from AAV2 and capsid sequences derived from AAV6 is referred to as AAV2/AAV6. In particular embodiments, the rAAV vector may comprise ITRs from AAV2, and capsid proteins from any one of AAV1, AAV2, AAV3, AAV4, AAV5, AAV6, AAV7, AAV8, AAV9, or AAV10. In a preferred embodiment, the rAAV comprises ITR sequences derived from AAV2 and capsid sequences derived from AAV6. In a preferred embodiment, the rAAV comprises ITR sequences derived from AAV2 and capsid sequences derived from AAV2.

In some embodiments, engineering and selection methods can be applied to AAV capsids to make them more likely to transduce cells of interest.

Construction of rAAV vectors, production, and purification thereof have been disclosed, e.g., in U.S. Pat. Nos. 9,169,494; 9,169,492; 9,012,224; 8,889,641; 8,809,058; and 8,784,799, each of which is incorporated by reference herein, in its entirety.

In various embodiments, one or more polynucleotides encoding a nuclease variant and/or donor repair template are introduced into a hepatic cell, by transducing the cell with a retrovirus, e.g., lentivirus, comprising the one or more polynucleotides.

As used herein, the term "retrovirus" refers to an RNA virus that reverse transcribes its genomic RNA into a linear double-stranded DNA copy and subsequently covalently integrates its genomic DNA into a host genome. Illustrative retroviruses suitable for use in particular embodiments, include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus.

As used herein, the term "lentivirus" refers to a group (or genus) of complex retroviruses. Illustrative lentiviruses include, but are not limited to: HIV (human immunodeficiency virus; including HIV type 1, and HIV 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV). In one embodiment, HIV based vector backbones (i.e., HIV cis-acting sequence elements) are preferred.

In various embodiments, a lentiviral vector contemplated herein comprises one or more LTRs, and one or more, or all, of the following accessory elements: a cPPT/FLAP, a Psi (Ψ) packaging signal, an export element, poly (A) sequences, and may optionally comprise a WPRE or HPRE, an insulator element, a selectable marker, and a cell suicide gene, as discussed elsewhere herein.

In particular embodiments, lentiviral vectors contemplated herein may be integrative or non-integrating or integration defective lentivirus. As used herein, the term "integration defective lentivirus" or "IDLV" refers to a lentivirus having an integrase that lacks the capacity to integrate the viral genome into the genome of the host cells. Integration-incompetent viral vectors have been described in patent application WO 2006/010834, which is herein incorporated by reference in its entirety.

Illustrative mutations in the HIV-1 pol gene suitable to reduce integrase activity include, but are not limited to: H12N, H12C, H16C, H16V, S81R, D41A, K42A, H51A, Q53C, D55V, D64E, D64V, E69A, K71A, E85A, E87A, D116N, D1161, D116A, N120G, N1201, N120E, E152G, E152A, D35E, K156E, K156A, E157A, K159E, K159A, K160A, R166A, D167A, E170A, H171A, K173A, K186Q, K186T, K188T, E198A, R199c, R199T, R199A, D202A, K211A, Q214L, Q216L, Q221 L, W235F, W235E, K236S, K236A, K246A, G247W, D253A, R262A, R263A and K264H.

In one embodiment, the HIV-1 integrase deficient pol gene comprises a D64V, D1161, Dl16A, E152G, or E152A mutation; D64V, Dl161, and E152G mutations; or D64V, Dl16A, and E152A mutations.

In one embodiment, the HIV-1 integrase deficient pol gene comprises a D64V mutation.

The term "long terminal repeat (LTR)" refers to domains of base pairs located at the ends of retroviral DNAs which, in their natural sequence context, are direct repeats and contain U3, R and U5 regions.

As used herein, the term "FLAP element" or "cPPT/FLAP" refers to a nucleic acid whose sequence includes the central polypurine tract and central termination sequences (cPPT and CTS) of a retrovirus, e.g., HIV-1 or HIV-2. Suitable FLAP elements are described in U.S. Pat. No. 6,682,907 and in Zennou, et al., 2000, *Cell*, 101:173. In another embodiment, a lentiviral vector contains a FLAP element with one or more mutations in the cPPT and/or CTS elements. In yet another embodiment, a lentiviral vector comprises either a cPPT or CTS element. In yet another embodiment, a lentiviral vector does not comprise a cPPT or CTS element.

As used herein, the term "packaging signal" or "packaging sequence" refers to psi [Ψ] sequences located within the retroviral genome which are required for insertion of the viral RNA into the viral capsid or particle, see e.g., Clever et al., 1995. *J. of Virology, Vol.* 69, No. 4; pp. 2101-2109.

The term "export element" refers to a cis-acting post-transcriptional regulatory element which regulates the transport of an RNA transcript from the nucleus to the cytoplasm of a cell. Examples of RNA export elements include, but are not limited to, the human immunodeficiency virus (HIV) rev response element (RRE) (see e.g., Cullen et al., 1991. *J. Virol.* 65: 1053; and Cullen et al., 1991. *Cell* 58: 423), and the hepatitis B virus post-transcriptional regulatory element (HPRE).

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid at the protein, e.g., woodchuck hepatitis virus posttranscriptional regulatory element (WPRE; Zufferey et al., 1999, *J. Virol.*, 73:2886); the posttranscriptional regulatory element present in hepatitis B virus (HPRE) (Huang et al., *Mol. Cell. Biol.*, 5:3864); and the like (Liu et al., 1995, *Genes Dev.*, 9:1766).

Lentiviral vectors preferably contain several safety enhancements as a result of modifying the LTRs. "Self-inactivating" (SIN) vectors refers to replication-defective vectors, e.g., in which the right (3') LTR enhancer-promoter region, known as the U3 region, has been modified (e.g., by deletion or substitution) to prevent viral transcription beyond the first round of viral replication. An additional safety enhancement is provided by replacing the U3 region of the 5' LTR with a heterologous promoter to drive transcription of the viral genome during production of viral particles. Examples of heterologous promoters which can be used include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters.

The terms "pseudotype" or "pseudotyping" as used herein, refer to a virus whose viral envelope proteins have been substituted with those of another virus possessing preferable characteristics. For example, HIV can be pseudotyped with vesicular stomatitis virus G-protein (VSV-G) envelope proteins, which allows HIV to infect a wider range of cells because HIV envelope proteins (encoded by the env gene) normally target the virus to $CD4^+$ presenting cells.

In certain embodiments, lentiviral vectors are produced according to known methods. See e.g., Kutner et al., *BMC Biotechnol.* 2009; 9:10. doi: 10.1186/1472-6750-9-10; Kutner et al. *Nat. Protoc.* 2009; 4(4):495-505. doi: 10.1038/nprot.2009.22.

According to certain specific embodiments contemplated herein, most or all of the viral vector backbone sequences are derived from a lentivirus, e.g., HIV-1. However, it is to be understood that many different sources of retroviral and/or lentiviral sequences can be used, or combined and numerous substitutions and alterations in certain of the lentiviral sequences may be accommodated without impairing the ability of a transfer vector to perform the functions described herein. Moreover, a variety of lentiviral vectors are known in the art, see Naldini et al., (1996a, 1996b, and 1998); Zufferey et al., (1997); Dull et al., 1998, U.S. Pat. Nos. 6,013,516; and 5,994,136, many of which may be adapted to produce a viral vector or transfer plasmid contemplated herein.

In various embodiments, one or more polynucleotides encoding a nuclease variant and/or donor repair template are introduced into a hepatic cell by transducing the cell with an adenovirus comprising the one or more polynucleotides.

Adenoviral based vectors are capable of very high transduction efficiency in many cell types and do not require cell division. With such vectors, high titer and high levels of expression have been obtained. This vector can be produced in large quantities in a relatively simple system. Most adenovirus vectors are engineered such that a transgene replaces the Ad Ela, Elb, and/or E3 genes; subsequently the replication defective vector is propagated in human 293 cells that supply deleted gene function in trans. Ad vectors can transduce multiple types of tissues in vivo, including non-dividing, differentiated cells such as those found in liver, kidney and muscle. Conventional Ad vectors have a large carrying capacity.

Generation and propagation of the current adenovirus vectors, which are replication deficient, may utilize a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones & Shenk, 1978), the current adenovirus vectors, with the help of 293 cells, carry foreign DNA in either the E1, the D3 or both regions (Graham & Prevec, 1991). Adenovirus vectors have been used in eukaryotic gene expression (Levrero et al., 1991; Gomez-Foix et al., 1992) and vaccine development (Grunhaus & Horwitz, 1992; Graham & Prevec, 1992). Studies in administering recombinant adenovirus to different tissues include trachea instillation (Rosenfeld et al., 1991; Rosenfeld et al., 1992), muscle injection (Ragot et al., 1993), peripheral intravenous injections (Herz & Gerard, 1993) and stereotactic inoculation into the brain (Le Gal La Salle et al., 1993). An example of the use of an Ad vector in a clinical trial involved polynucleotide therapy for antitumor immunization with intramuscular injection (Sterman et al., *Hum. Gene Ther.* 7:1083-9 (1998)).

In various embodiments, one or more polynucleotides encoding nuclease variant and/or donor repair template are introduced into a hepatic cell by transducing the cell with a herpes simplex virus, e.g., HSV-1, HSV-2, comprising the one or more polynucleotides.

The mature HSV virion consists of an enveloped icosahedral capsid with a viral genome consisting of a linear double-stranded DNA molecule that is 152 kb. In one embodiment, the HSV based viral vector is deficient in one or more essential or non-essential HSV genes. In one embodiment, the HSV based viral vector is replication deficient. Most replication deficient HSV vectors contain a deletion to remove one or more intermediate-early, early, or late HSV genes to prevent replication. For example, the HSV vector may be deficient in an immediate early gene selected from the group consisting of ICP4, ICP22, ICP27, ICP47, and a combination thereof. Advantages of the HSV vector are its ability to enter a latent stage that can result in long-term DNA expression and its large viral DNA genome that can accommodate exogenous DNA inserts of up to 25 kb. HSV-based vectors are described in, for example, U.S. Pat. Nos. 5,837,532, 5,846,782, and 5,804,413, and International Patent Applications WO 91/02788, WO 96/04394, WO 98/15637, and WO 99/06583, each of which are incorporated by reference herein in its entirety.

H. Genome Edited Cells

The genome edited cells manufactured by the methods contemplated in particular embodiments comprise one or more gene edits in a PCSK9 gene and provide improved cell-based therapeutics for the prevention, treatment, or amelioration of at least one symptom, of a cardiovascular disease, high cholesterol or hypercholesterolemia or condition associated therewith.

Genome edited cells contemplated in particular embodiments may be autologous/autogeneic ("self") or non-autologous ("non-self," e.g., allogeneic, syngeneic or xenogeneic). "Autologous," as used herein, refers to cells from the same subject. "Allogeneic," as used herein, refers to cells of the same species that differ genetically to the cell in comparison. "Syngeneic," as used herein, refers to cells of a different subject that are genetically identical to the cell in comparison. "Xenogeneic," as used herein, refers to cells of a different species to the cell in comparison. In preferred embodiments, the cells are obtained from a mammalian subject. In a more preferred embodiment, the cells are obtained from a primate subject, optionally a non-human primate. In the most preferred embodiment, the cells are obtained from a human subject.

An "isolated cell" refers to a non-naturally occurring cell, e.g., a cell that does not exist in nature, a modified cell, an engineered cell, etc., that has been obtained from an in vivo tissue or organ and is substantially free of extracellular matrix.

As used herein, the term "population of cells" refers to a plurality of cells that may be made up of any number and/or combination of homogenous or heterogeneous cell types, as described elsewhere herein Illustrative examples of cell types whose genome can be edited using the compositions and methods contemplated herein include, but are not limited to, cell lines, primary cells, stem cells, progenitor cells, and differentiated cells, and mixtures thereof.

In preferred embodiments, the genome editing compositions are used to edit cells in tissues or organs in vivo.

In preferred embodiments, the genome editing compositions are used to edit liver cells in vivo.

In preferred embodiments, the compositions and methods contemplated herein are used to edit liver cells.

Illustrative examples of liver cells or hepatic cells that may be edited using the compositions and methods contemplated herein include, but are not limited to hepatocytes, stellate cells, Kupffer cells, and liver endothelial cells.

In particular embodiments, a cell comprises an edited PCSK9 gene, wherein the edit is a DSB repaired by NHEJ. In particular embodiments, the edit is an insertion or deletion (INDEL) of about 1, 2, 3, 4, 5, 6, 7, 8, 9, 10, 11, 12, 13, 14 15, 16, 17, 18, 19, 20, 21, 22, 23, 24, 25 or more nucleotides in a coding sequence of the PCSK9 gene, preferably in exon 4 of the PCSK9 gene, more preferably at SEQ ID NO: 11 (or SEQ ID NO: 13) in exon 4 of the PCSK9 gene.

In particular embodiments, a cell comprises an edited PCSK9 gene comprising a donor repair template incorporated at a DSB repaired by HDR.

In particular embodiments, a cell comprises an edited PCSK9 gene comprising a donor repair template comprising a PCSK9 gene or portion thereof and is designed to introduce one or more mutations in a genomic PCSK9 sequence to modify PCSK9 expression or activity, and preferably, to decrease or eliminate PCSK9 expression and/or activity.

I. Compositions and Formulations

The compositions contemplated in particular embodiments may comprise one or more polypeptides, polynucleotides, vectors comprising same, and genome editing compositions and genome edited cell compositions, as contemplated herein. The genome editing compositions and methods contemplated in particular embodiments are useful for editing a target site in a subtilisin/kexin type 9 (PCSK9) gene in a cell or a population of cells. In preferred embodiments, a genome editing composition is used to edit a PCSK9 gene in a hepatic cell.

In various embodiments, the compositions contemplated herein comprise a nuclease variant, and optionally an end-processing enzyme, e.g., a 3'-5' exonuclease (Trex2). The nuclease variant may be in the form of an mRNA that is introduced into a cell via polynucleotide delivery methods disclosed supra, e.g., electroporation, lipid nanoparticles, etc. In one embodiment, a composition comprising an mRNA encoding a homing endonuclease variant or megaTAL, and optionally a 3'-5' exonuclease, is introduced in a cell via polynucleotide delivery methods disclosed supra. The composition may be used to generate a genome edited cell or population of genome edited cells by error prone NHEJ.

In various embodiments, the compositions contemplated herein comprise a donor repair template. The composition may be delivered to a cell that expresses or will express nuclease variant, and optionally an end-processing enzyme. In one embodiment, the composition may be delivered to a cell that expresses or will express a homing endonuclease variant or megaTAL, and optionally a 3'-5' exonuclease. Expression of the gene editing enzymes in the presence of the donor repair template can be used to generate a genome edited cell or population of genome edited cells by HDR.

In particular embodiments, the compositions contemplated herein comprise a nuclease variant, and optionally, a donor repair template. In particular embodiments, the compositions contemplated herein comprise a nuclease variant, an end-processing enzyme, and optionally, a donor repair template. The nuclease variant and/or end-processing enzyme may be in the form of an mRNA that is introduced into the cell via polynucleotide delivery methods disclosed supra.

In particular embodiments, the compositions contemplated herein comprise a homing endonuclease variant or megaTAL, and optionally, a donor repair template. In particular embodiments, the compositions contemplated herein comprise a homing endonuclease variant or megaTAL, a 3'-5' exonuclease, and optionally, a donor repair template. The homing endonuclease variant, megaTAL, and/or 3'-5' exonuclease may be in the form of an mRNA that is introduced into the cell via polynucleotide delivery methods disclosed supra.

Compositions include, but are not limited to pharmaceutical compositions. A "pharmaceutical composition" refers to a composition formulated in pharmaceutically-acceptable or physiologically-acceptable solutions for administration to a cell or an animal, either alone, or in combination with one or more other modalities of therapy. It will also be understood that, if desired, the compositions may be administered in combination with other agents as well, such as, e.g., cytokines, growth factors, hormones, small molecules, chemotherapeutics, pro-drugs, drugs, antibodies, or other various pharmaceutically-active agents. There is virtually no limit to other components that may also be included in the compositions, provided that the additional agents do not adversely affect the composition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "pharmaceutically acceptable carrier" refers to a diluent, adjuvant, excipient, or vehicle with which the therapeutic cells are administered. Illustrative examples of pharmaceutical carriers can be sterile liquids, such as cell culture media, water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. Suitable pharmaceutical excipients in particular embodiments, include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Except insofar as any conventional media or agent is incompatible with the active ingredient, its use in the therapeutic compositions is contemplated. Supplementary active ingredients can also be incorporated into the compositions.

In one embodiment, a composition comprising a pharmaceutically acceptable carrier is suitable for administration to a subject. In particular embodiments, a composition comprising a carrier is suitable for parenteral administration, e.g., intravascular (intravenous or intraarterial), intraperitoneal or intramuscular administration. In particular embodiments, a composition comprising a pharmaceutically acceptable carrier is suitable for intraventricular, intraspinal, or intrathecal administration. Pharmaceutically acceptable carriers include sterile aqueous solutions, cell culture media, or dispersions. The use of such media and agents for pharmaceutically active substances is well known in the art. Except insofar as any conventional media or agent is incompatible with the transduced cells, use thereof in the pharmaceutical compositions is contemplated.

The pharmaceutically acceptable carrier must be of sufficiently high purity and of sufficiently low toxicity to render it suitable for administration to the human subject being treated. It further should maintain or increase the stability of the composition. The pharmaceutically acceptable carrier can be liquid or solid and is selected, with the planned manner of administration in mind, to provide for the desired bulk, consistency, etc., when combined with other components of the composition. For example, the pharmaceutically acceptable carrier can be, without limitation, a binding agent (e.g., pregelatinized maize starch, polyvinylpyrrolidone or hydroxypropyl methylcellulose, etc.), a filler (e.g., lactose and other sugars, microcrystalline cellulose, pectin, gelatin, calcium sulfate, ethyl cellulose, polyacrylates, calcium hydrogen phosphate, etc.), a lubricant (e.g., magnesium stearate, talc, silica, colloidal silicon dioxide, stearic acid, metallic stearates, hydrogenated vegetable oils, corn starch, polyethylene glycols, sodium benzoate, sodium acetate, etc.), a disintegrant (e.g., starch, sodium starch glycolate, etc.), or a wetting agent (e.g., sodium lauryl sulfate, etc.). Other suitable pharmaceutically acceptable carriers for the compositions contemplated herein include, but are not limited to, water, salt solutions, alcohols, polyethylene glycols, gelatins, amyloses, magnesium stearates, talcs, silicic acids, viscous paraffins, hydroxymethylcelluloses, polyvinylpyrrolidones and the like.

Such carrier solutions also can contain buffers, diluents and other suitable additives. The term "buffer" as used herein refers to a solution or liquid whose chemical makeup neutralizes acids or bases without a significant change in pH. Examples of buffers contemplated herein include, but are not limited to, Dulbecco's phosphate buffered saline (PBS), Ringer's solution, 5% dextrose in water (D5W), normal/physiologic saline (0.9% NaCl).

The pharmaceutically acceptable carriers may be present in amounts sufficient to maintain a pH of the composition of about 7. Alternatively, the composition has a pH in a range from about 6.8 to about 7.4, e.g., 6.8, 6.9, 7.0, 7.1, 7.2, 7.3, and 7.4. In still another embodiment, the composition has a pH of about 7.4.

Compositions contemplated herein may comprise a non-toxic pharmaceutically acceptable medium. The compositions may be a suspension. The term "suspension" as used herein refers to non-adherent conditions in which cells are not attached to a solid support. For example, cells maintained as a suspension may be stirred or agitated and are not adhered to a support, such as a culture dish.

In certain embodiments, a pharmaceutically acceptable carrier is substantially free of natural proteins of human or animal origin, and suitable for storing a composition comprising a population of genome edited T cells. The therapeutic composition is intended to be administered into a human patient, and thus is substantially free of cell culture components such as bovine serum albumin, horse serum, and fetal bovine serum.

In some embodiments, compositions are formulated in a pharmaceutically acceptable cell culture medium. Such compositions are suitable for administration to human subjects. In particular embodiments, the pharmaceutically acceptable cell culture medium is a serum free medium.

Serum-free medium has several advantages over serum containing medium, including a simplified and better defined composition, a reduced degree of contaminants, elimination of a potential source of infectious agents, and lower cost. In various embodiments, the serum-free medium is animal-free, and may optionally be protein-free. Optionally, the medium may contain biopharmaceutically acceptable recombinant proteins. "Animal-free" medium refers to medium wherein the components are derived from non-animal sources. Recombinant proteins replace native animal proteins in animal-free medium and the nutrients are obtained from synthetic, plant or microbial sources. "Protein-free" medium, in contrast, is defined as substantially free of protein.

Illustrative examples of serum-free media used in particular compositions includes, but is not limited to QBSF-60 (Quality Biological, Inc.), StemPro-34 (Life Technologies), and X-VIVO 10.

In particular embodiments, the composition is substantially free of *mycoplasma*, endotoxin, and microbial contamination. By "substantially free" with respect to endotoxin is meant that there is less endotoxin per dose of cells than is allowed by the FDA for a biologic, which is a total endotoxin of 5 EU/kg body weight per day, which for an average 70 kg person is 350 EU per total dose of cells. In particular embodiments, compositions comprising hepatic cells transduced with a retroviral vector contemplated herein contain about 0.5 EU/mL to about 5.0 EU/mL, or about 0.5 EU/mL, 1.0 EU/mL, 1.5 EU/mL, 2.0 EU/mL, 2.5 EU/mL, 3.0 EU/mL, 3.5 EU/mL, 4.0 EU/mL, 4.5 EU/mL, or 5.0 EU/mL.

In certain embodiments, compositions and formulations suitable for the delivery of polynucleotides are contemplated including, but not limited to, one or more mRNAs encoding one or more reprogrammed nucleases, and optionally end-processing enzymes.

Exemplary formulations for ex vivo delivery may also include the use of various transfection agents known in the art, such as calcium phosphate, electroporation, heat shock and various liposome formulations (i.e., lipid-mediated transfection). Liposomes, are lipid bilayers entrapping a fraction of aqueous fluid. DNA spontaneously associates to the external surface of cationic liposomes (by virtue of its charge) and these liposomes will interact with the cell membrane.

In particular embodiments, formulation of pharmaceutically-acceptable carrier solutions is well-known to those of skill in the art, as is the development of suitable dosing and treatment regimens for using the particular compositions described herein in a variety of treatment regimens, including e.g., enteral and parenteral, e.g., intravascular, intravenous, intrarterial, intraosseously, intraventricular, intracerebral, intracranial, intraspinal, intrathecal, and intramedullary administration and formulation. It would be understood by the skilled artisan that particular embodiments contemplated herein may comprise other formulations, such as those that are well known in the pharmaceutical art, and are described, for example, in *Remington: The Science and Practice of Pharmacy*, volume I and volume II 22$^{nd}$ Edition. Edited by Loyd V. Allen Jr. Philadelphia, Pa.: Pharmaceutical Press; 2012, which is incorporated by reference herein, in its entirety.

All publications, patent applications, and issued patents cited in this specification are herein incorporated by reference as if each individual publication, patent application, or issued patent were specifically and individually indicated to be incorporated by reference.

Although the foregoing embodiments have been described in some detail by way of illustration and example for purposes of clarity of understanding, it will be readily apparent to one of ordinary skill in the art in light of the teachings contemplated herein that certain changes and modifications may be made thereto without departing from the spirit or scope of the appended claims. The following examples are provided by way of illustration only and not by way of limitation. Those of skill in the art will readily recognize a variety of noncritical parameters that could be changed or modified to yield essentially similar results.

EXAMPLES

Example 1

Figure 2:
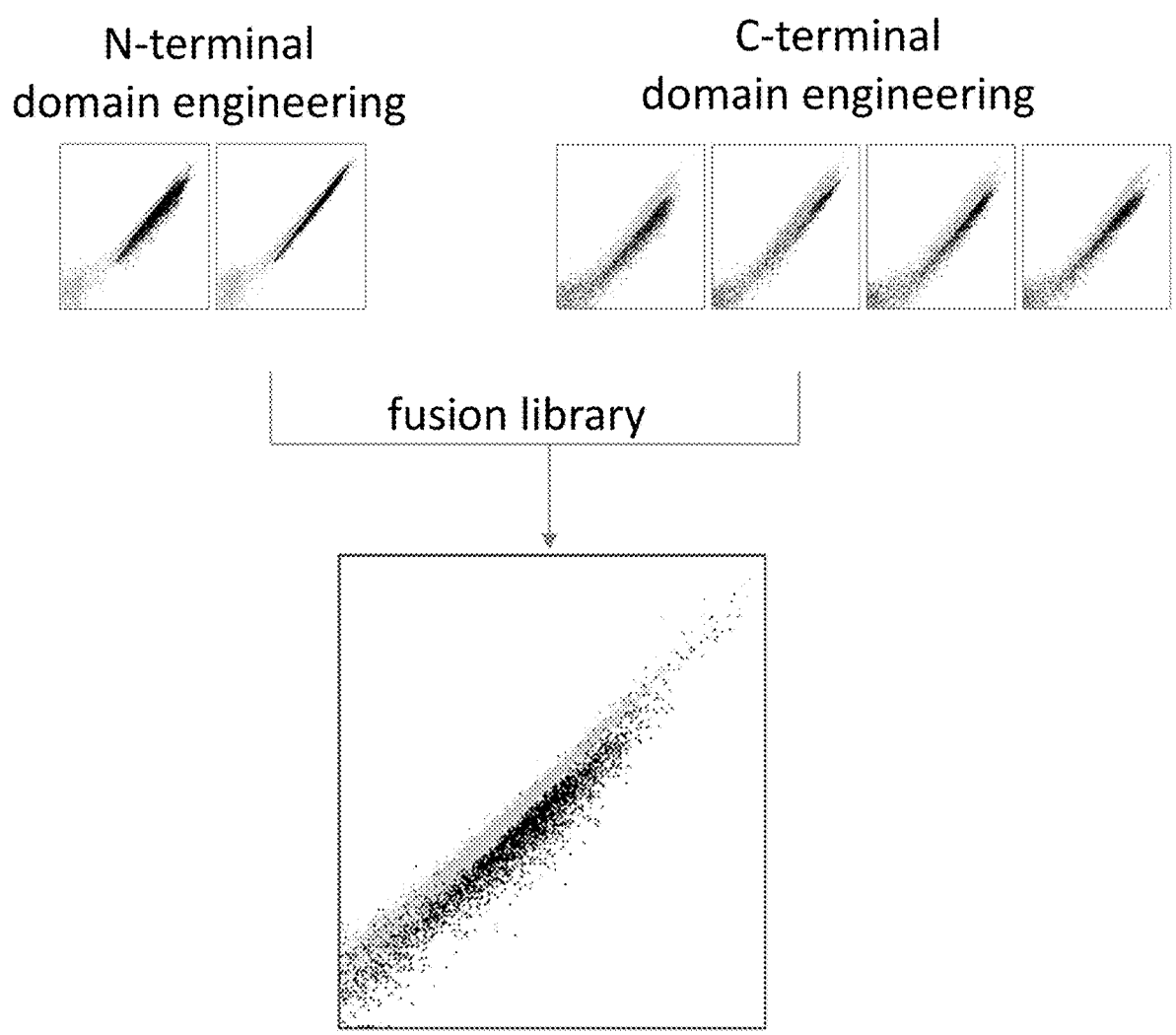
FIG. 2 shows how the PCSK9 HE was reprogrammed via engineering of the NTD and CTD against chimeric 'half-sites' through three rounds of sorting, followed by fusion of the reprogrammed domains and screening against the complete PCSK9 target site to isolate a fully reprogrammed HE.

Reprogramming I-OnuI to Disrupt a Proprotein Convertase Subtilisin/Kexin Type 9 (PCSK9) Gene I-OnuI was reprogrammed to target exon 4 of a PCSK9 gene (FIG. 1) by constructing modular libraries containing variable amino acid residues in the DNA recognition interface. To construct the variants, degenerate codons were incorporated into I-OnuI DNA binding domains using oligonucleotides. The oligonucleotides encoding the degenerate codons were used as PCR templates to generate variant libraries by gap recombination in the yeast strain *S. cerevisiae*. Each variant library spanned either the N- or C-terminal I-OnuI DNA recognition domain and contained ~$10^7$ to $10^8$ unique transformants. The resulting surface display libraries were screened by flow cytometry for cleavage activity against target sites comprising the corresponding domains' "half-sites" (SEQ ID NOs: 14-19), as shown in FIG. 2.

Yeast displaying the N- and C-terminal domain reprogrammed I-OnuI HEs were purified and the plasmid DNA was extracted. PCR reactions were performed to amplify the reprogrammed domains, which were subsequently fused and transformed into S. cerevisiae to create a library of reprogrammed domain combinations. Fully reprogrammed I-OnuI variants that recognize the complete target site (SEQ ID NO: 11) present in exon 4 of a PCSK9 gene were identified from this library and purified.

Example 2

Reprogrammed I-OnuI Homing Endonucleases that Target Exon 4 of the PCSK9 Gene

Figure 3:
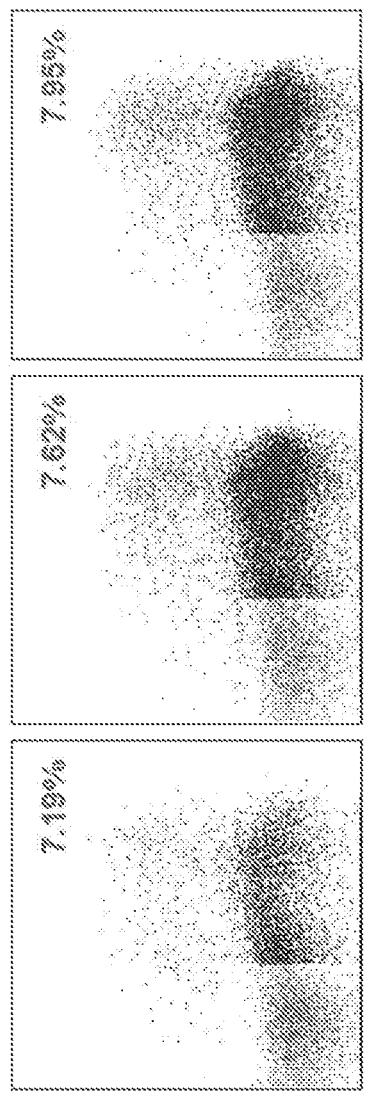
FIG. 3 shows the activity of a PCSK9 HE variant in a chromosomal reporter assay, and increased activity by subsequent refinement of PCSK9.H7 to achieve a more active variant (PCSK9.H7.C11) through mutagenesis and screening under more stringent conditions.
Figure 3:
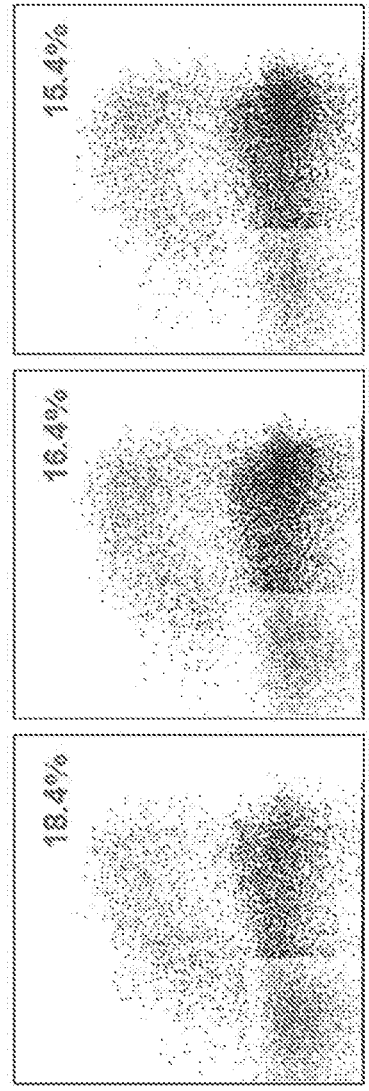

The activity of reprogrammed I-OnuI HEs that target exon 4 of the PCSK9 gene was measured using a chromosomally integrated fluorescent reporter system (Certo et. al., 2011). Fully reprogrammed I-OnuI HEs that bind and cleave the PCSK9 target sequence were cloned into mammalian expression plasmids and then individually transfected into a HEK 293T fibroblast cell line that contained the PCSK9 target sequence upstream of an out-of-frame gene encoding the fluorescent mCherry protein. Cleavage of the embedded target site by the HE and the accumulation of indels following DNA repair via the non-homologous end joining (NHEJ) pathway results in approximately one out of three repaired loci placing the fluorescent reporter gene back "in-frame". The percentage of mCherry fluorescing HEK 293T cells is therefore used a readout of endonuclease activity at the chromosomally embedded target sequence. The fully reprogrammed I-OnuI HEs that bind and cleave the PCSK9 target sequence showed a moderate efficiency of mCherry expression in a cellular chromosomal context. FIG. 3 (top panels).

A secondary I-OnuI variant library was next generated by performing random mutagenesis on the PCSK9.H7 HE variant (e.g., SEQ ID NO: 6). Display-based flow sorting was performed under more stringent cleavage conditions in an effort to isolate variants with improved catalytic efficiency. FIG. 3 (bottom panel). This process led to variant PCSK9.H7.C11 (SEQ ID NO: 7) with an approximately 2-fold higher rate of mCherry expressing cells.

Figure 4:
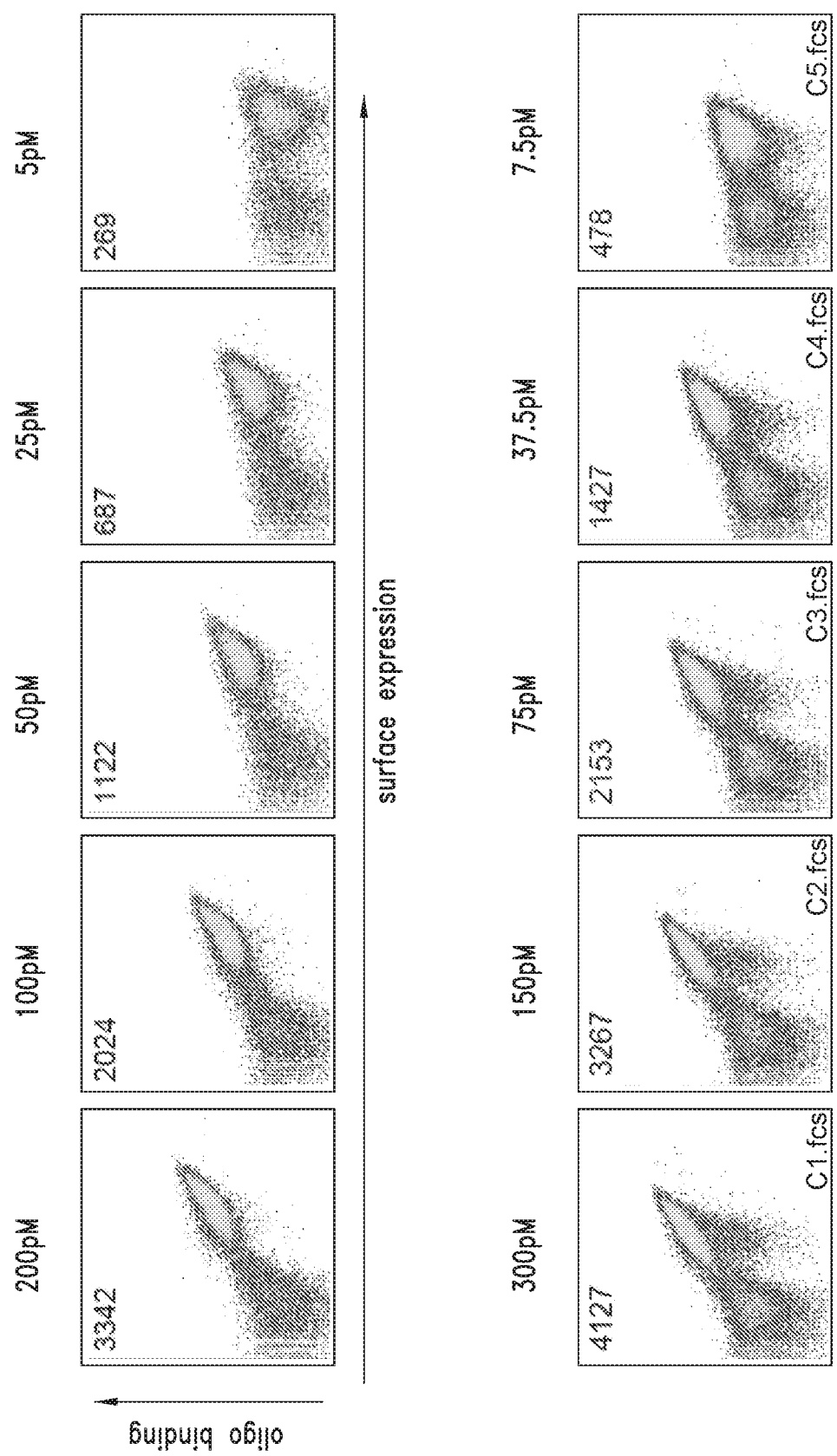
FIG. 4 shows that the refined PCSK9.H7.C11 HE variant has sub-nanomolar affinity properties as measured using a yeast surface display based substrate titration assay.
Figure 5:
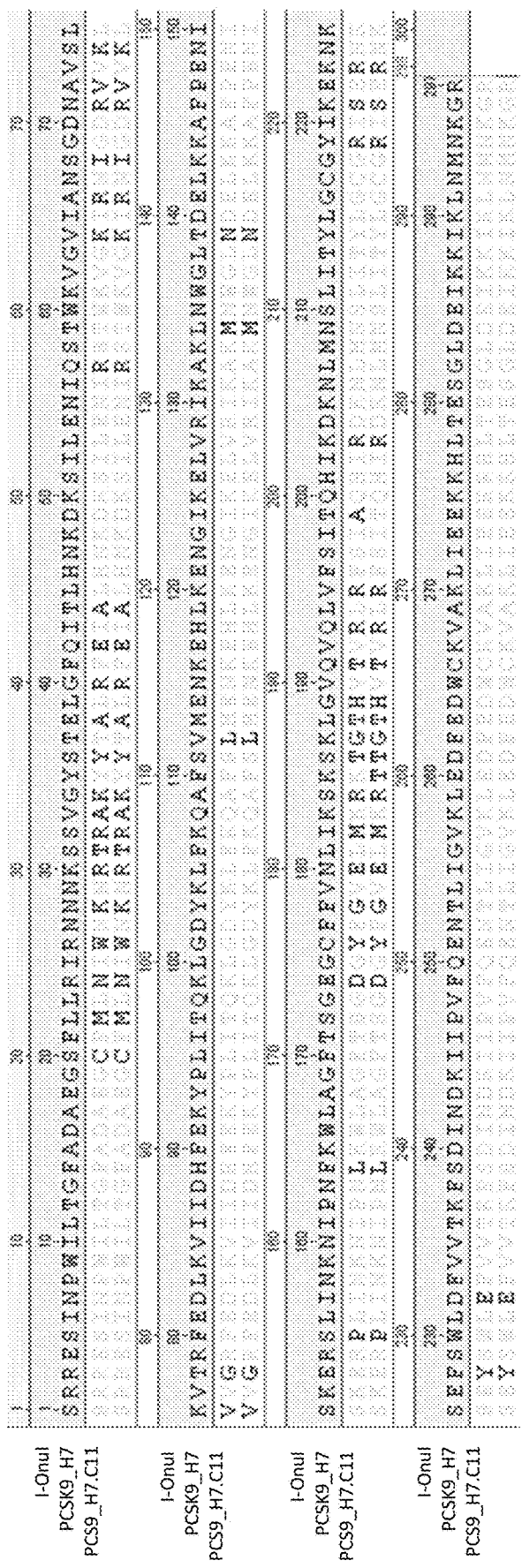
FIG. 5 shows an alignment of pre- and post-refined PCSK9 HEs (SEQ ID NOS: 64 and 65) to the wild-type I-OnuI protein (SEQ ID NO:63), highlighting non-identical positions.

PCSK9.H7.C11 has two amino acid mutations relative to the parental variant, both of which are located within the DNA recognition interface. PCSK9.H7.C11 has sub-nanomolar affinity for the exon 4 target site. FIG. 4. FIG. 5 shows the relative alignments of representative I-OnuI variants as well as the positional information of the residues comprising the DNA recognition interface.

Example 3

Efficient Disruption of Exon 4 of PCSK9

Figure 6A:
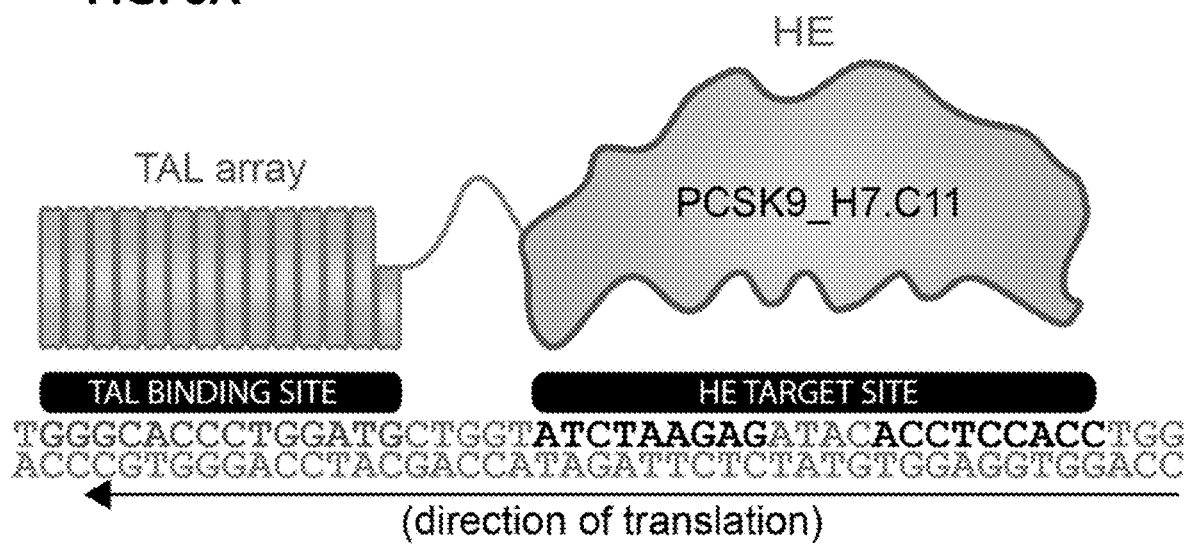
FIG. 6A shows the binding site (SEQ ID NOS: 66 and 67) for the TAL RVDs fused to the PCSK9.H7.C11 HE variant to generate a PCSK9.H7.C11 megaTAL.

The PCSK9.H7.C11 HE variant was formatted as a megaTAL (SEQ ID NO: 9) by appending an N-terminal 13.5 unit TAL array, corresponding to a 14 base pair TAL array target site (SEQ ID NO: 12), to the N-terminus of the meganuclease domain. FIG. 6A. The megaTAL target site sequence is set forth in SEQ ID NO: 13. Another PCSK9.H7.C11 megaTAL comprises a C-terminal fusion to Trex2 via a linker sequence (SEQ ID NO: 10).

Figure 6B:
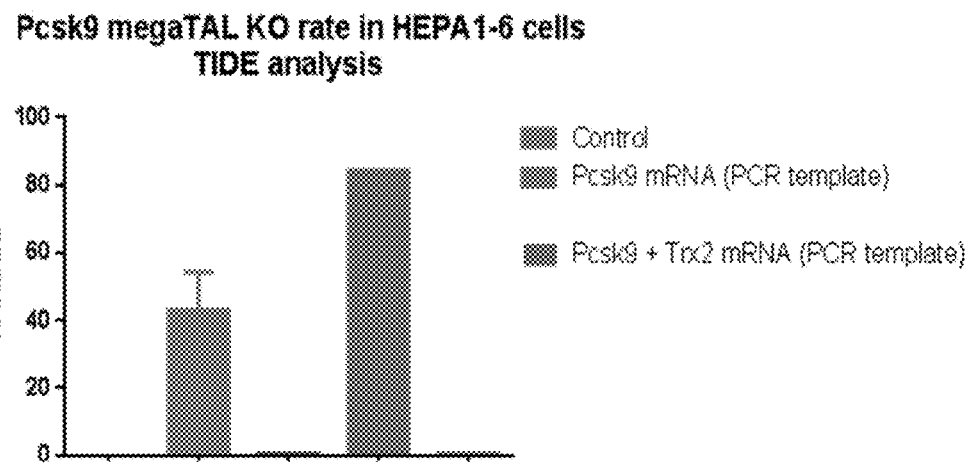
FIG. 6B shows that co-delivery of PCSK9.H7.C11 megaTAL and TREX2 into HEPA 1-6 cells results in a high editing rate at the target site (80%).

PCSK9.H7.C11 megaTAL mRNA was introduced into HEPA1-6 cells both in the presence and absence of Trex2 mRNA. Genomic DNA was isolated followed by PCR amplification across the PCSK9 exon 4 target site. The frequency of indels was measured using Tracking of Indels by DEcomposition (TIDE, see Brinkman et al., 2014). FIG. 6B. shows a representative TIDE analysis.

Example 4

In Vitro Activity of PCSK9 MegaTAL in the Presence and Absence of Trex2

Figure 7:
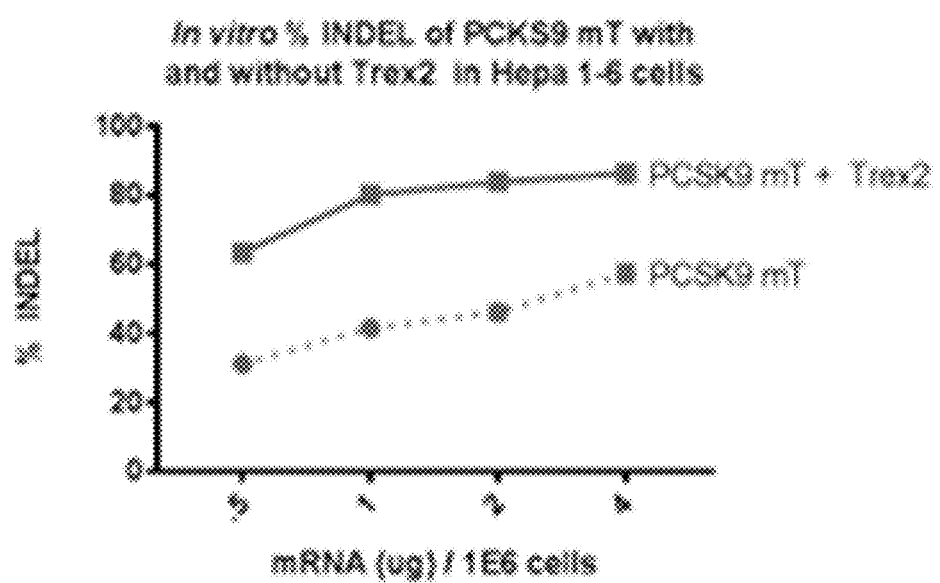
FIG. 7 shows that a PCSK9 megaTAL is highly active in vitro when mRNA encoding the megaTAL is electroporated into Hepa1-6 cells (dotted line). INDEL rates were doubled by the inclusion of Trex2 3'-5' exonuclease mRNA (solid line).

PCSK9 megaTAL activity alone and in the presence of Trex2 3' was determined in an in vitro activity assay using mouse liver epithelial cells (Hepa1-6, ATCC CRL-1830) (FIG. 7). $10^6$ Hepa1-6 cells were electroporated in duplicate with 0.5, 1, 2 or 4 µg of PCSK9 megaTAL mRNA with or without an equal molar ratio of Trex2 mRNA using a Neon electroporation system (100 µl tip) following the manufacturers recommended protocol. Electroporated cells were cultured in a 12 well tissue culture plate and grown for 48 hours at 37° C. degrees. After culture, genomic DNA was isolated from the cells using Qiagen's Blood and Tissue DNAasy Kit (Cat: 69581), per the manufactures recommended protocol.

Isolated genomic DNA was used as a template to amplify across the PCSK9 megaTAL DNA binding domain to quantify the presence of INDELs using Tracking of INDEL by decomposition (TIDE) analysis (Brinkman et al., 2014). Forward primer (5'-GCATATGTTTGGGAGGTTGG-3') and reverse primer (5'-CCTTGACAGTTGAGCACACG-3') were used to amplify the region around the PCSK9 megaTAL binding site.

The highest dose of PCSK9 megaTAL generated about 60% INDELs in the absence of Trex2. In the presence of Trex2, editing rates nearly doubled at low doses and increased to about 80% INDELs at high doses.

Example 5

In Vivo Activity of PCSK9 MegaTAL in the Presence and Absence of Trex2

Figure 8:
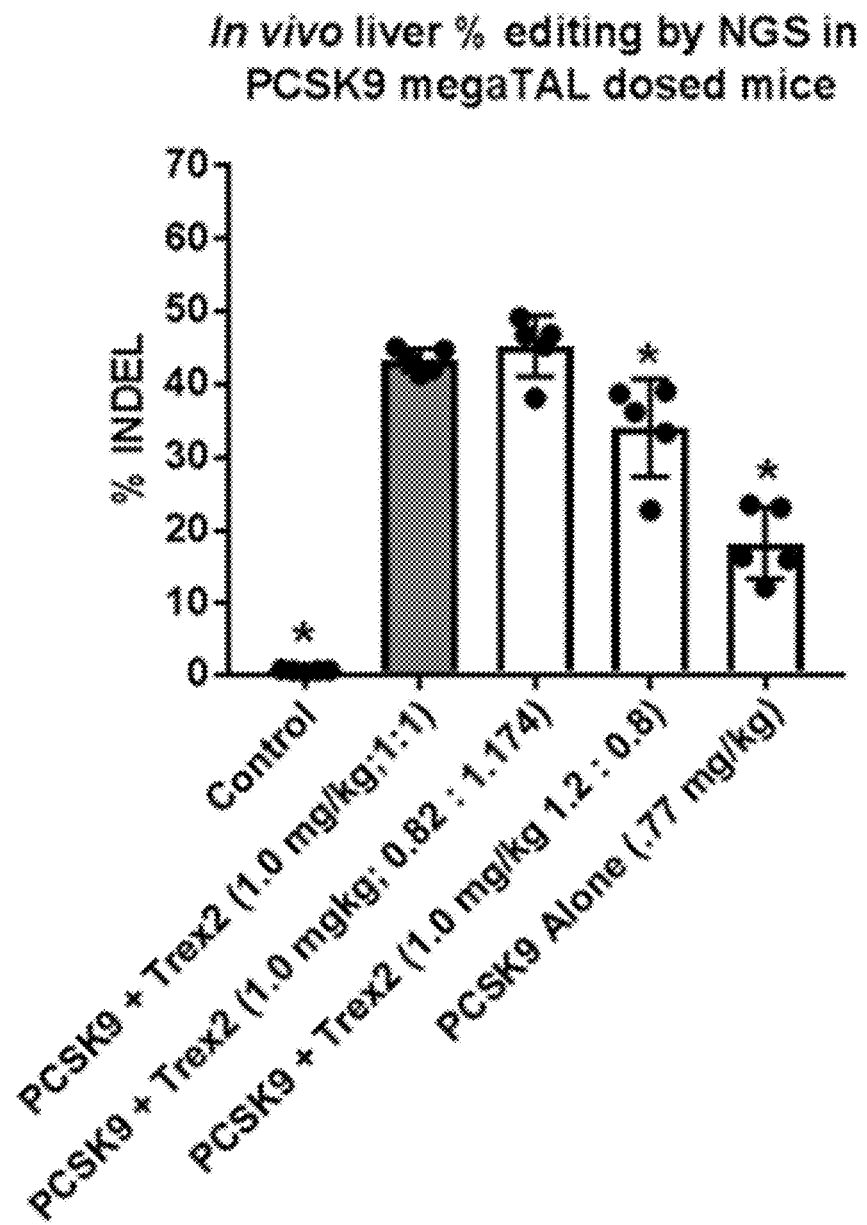
FIG. 8 shows the INDEL rates in liver cells of Balb/C mice dosed by tail vein injection with PCSK9 megaTAL and Trex2 mRNA formulated at different molar ratios (1:1, 0.82:1.174 and 1.2:0.8, respectively) or with PCSK9 megaTAL mRNA alone. Student test significance was calculated using the 1:1 ratio cohort as the comparator (dark bar). *=p≤0.05.

The in vivo activity of PCSK9 megaTAL alone or in combination with Trex2 at difference molar ratios was determined. PCSK9 megaTAL and Trex2 mRNAs were mixed in 1.0:1.0, 0.82:11.174 or 1.2:0.8 molar ratios. The PCSK9 megaTAL mRNA alone and PCSK9 megaTAL and Trex2 mRNA mixes were formulated in lipid nano-particles (LNP) by Acuitas Therapeutics Inc. mRNA/LNP formulations where diluted in phosphate buffered saline (PBS) and administered to Balb/C mice (5 per condition) via tail vein injection at a dose of 1 mg/kg for each condition, except the PCSK9 megaTAL alone condition, which was dosed at 0.77 mg/kg to ensure that the same total amount of PCSK9 megaTAL mRNA was being delivered to animals as those receiving the 1.0:1.0 molar ratio dose. PBS vehicle was used as a negative control condition. 96 hours post-administration, animals were euthanized. Genomic DNA was isolated from the livers of these mice using the Qiagen's Blood and Tissue DNAasy Kit (Cat: 69581), per manufactures recommended protocol. Editing was by measured by calculating the INDEL frequency at the PCSK9 megaTAL cut site using next-generation amplicon sequencing with forward primer (5'-ACACTCTTTCCCTACACGACGCTCTTCC-GATCTAGCAATAGTGTTAACCCAGGAA CT-3') and reverse primer (5'-GTGACTGGAGTTCA-GACGTGTGCTCTTCCGATCTTGTTGAAGTCGGT-GATGGTGA-3'). The average INDELs for each condition were plotted and significance (*=p≤5, student t-test) was calculated by comparing all conditions to the 1.0:1.0 PCSK megaTAL to Trex2 dose (FIG. 8, dark bar).

The PCSK9 megaTAL/Trex2 formulations at ratios of 1:1 or 0.82 to 1.174 were more effective than the PCSK9 megaTAL/Trex2 formulated at a ratio of 1.2 to 0.8 or than PCSK9 megaTAL alone.

Example 6

In Vitro and In Vivo mRNA Characteristics

PSCK9 megaTAL and Trex2 mRNAs were purified using a silica resin (TriLink), high-pressure liquid chromatography (HPLC) (TriLink) or an in-house method comprising polyA mRNA isolation and dsRNA depletion.

PCSK9 megaTAL mRNA made using the three methods were compared in three separate in vitro assays (FIG. 9A-C). mRNA length was measured by running the mRNA on an Advanced Analytical, capillary electrophoreses based Fragment Analyzer using their standard RNA analysis reagents per the manufactures recommended protocol. The area under the curve was measured using Prosize software and the average total percent area of the selected peak for three replicates was plotted (FIG. 9A). Double-stranded mRNA (dsRNA) can be toxic when delivered in vivo. To measure the amount of dsRNA in the mRNA preparations we performed dsRNA dot-blot as described in (Kariko et al., 2011). Our mRNA production process produces mRNA with undetectable levels of dsRNA, similar to the HPLC purification process when compared to silica purified mRNA (FIG. 9B). mRNA toxicity was measured in an in vitro cell growth assay using ACEA Biosciences, Inc.'s RTCA iCELLigence impedance-based assy. Human BJ fibroblasts (ATCC, CRL-2522) cells were seeded into the iCELLigence plate and allowed to adhere for 18-24 hours. mRNA was formulated into Lipofectamine MessengerMax transfection reagent per the manufacturers recommend protocol and used to transfect the cells. The amount of cell growth was measured for 48 hours as and the slope of growth is graphed as an indicator of toxicity (FIG. 9C).

Figure 9F:
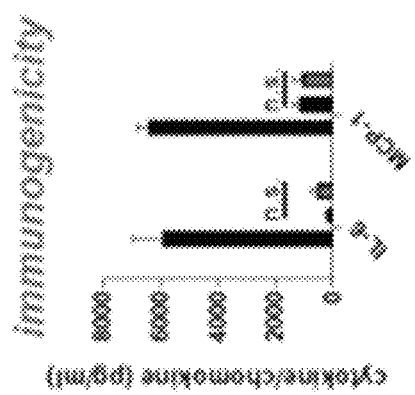
Figure 9E:
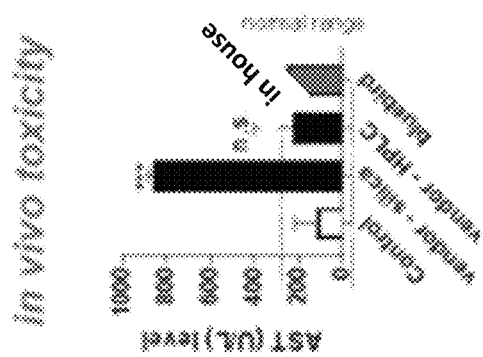
Figure 9D:
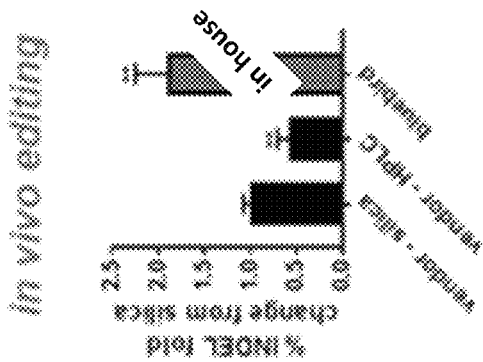

PCSK9 megaTAL and Trex2 mRNA made using the three methods were formulated at a 1.0:1.0 molar ratio as described in Example 5. Five Balb/C mice per condition were injected with LNP formulated mRNA at a dose of 1 mg/kg (FIG. 9D-F). INDEL analysis was performed as described in Example 5 and graphed as fold change compared to the silica condition (FIG. 9D). The relative toxicity of each mRNA preparation was assayed by taking mandibular bleeds from animals 24 hours after dosing and measuring Aspartate Aminotransferase enzyme levels (FIG. 9E). The in vivo immunogenicity of the purified mRNAs was measured by quantifying chemokine and cytokine levels from serum collected four hours after mRNA formulation dosing using EMD Millipore's MILLIPLEX MAP Mouse Cytokine/Chemokine Magnetic Bead based Luminex panel (cat #: MCYTOMAG-70KM).

Overall, the in-house method comprising polyA mRNA purification and dsRNA depletion produced mRNA that was the same quality or better quality than commercially sourced silica or HPLC purified mRNA, in both in vitro mRNA characteristics or in in vivo activity, toxicity/immunogenicity assays.

Example 7

Dose Titration of PCSK9 MegaTAL and Trex2 mRNAs Formulated in LNPs

Figure 10:
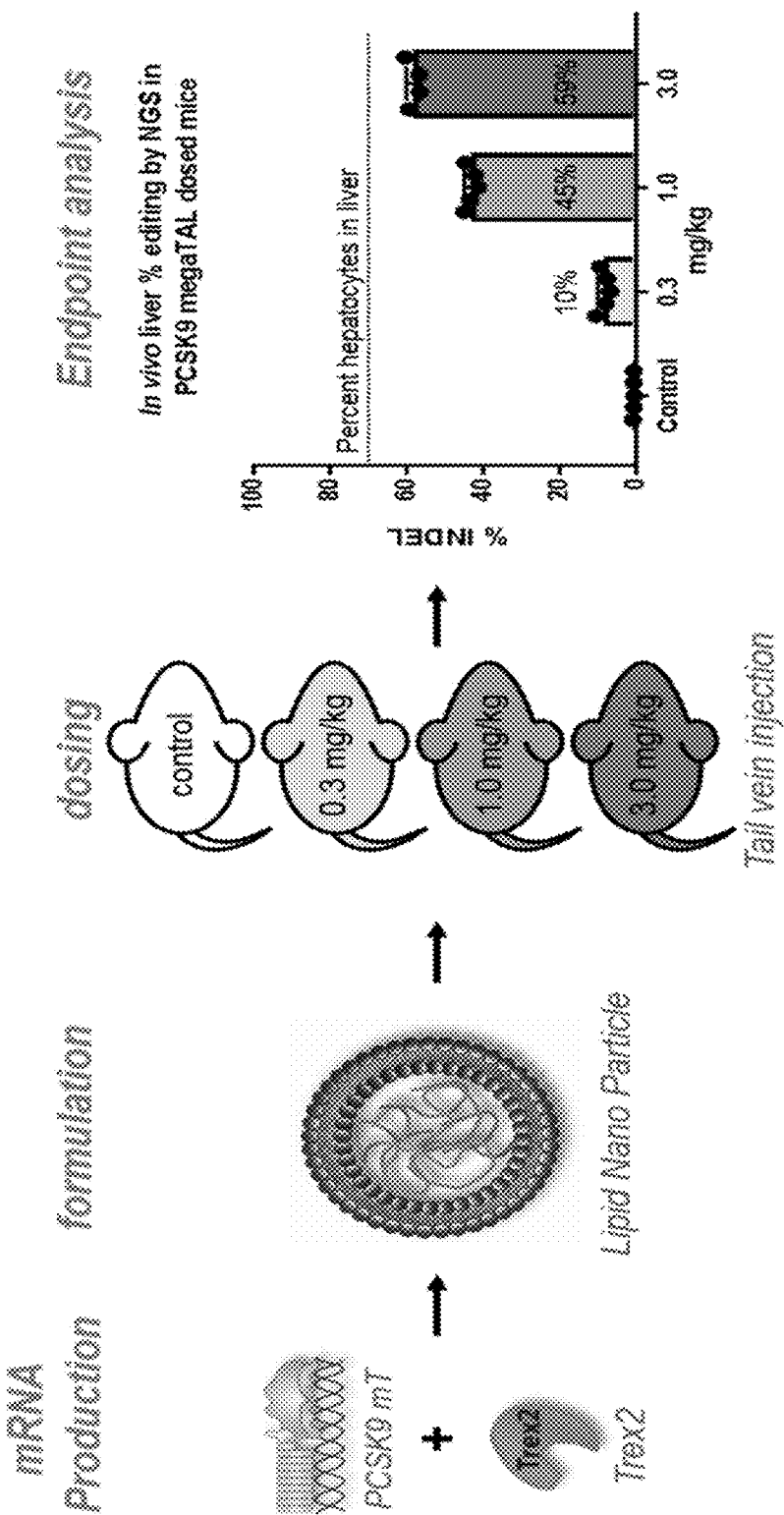
FIG. 10 shows an in vivo liver editing dose titration of PCSK9 megaTAL and Trex2 mRNA purified using polyA selection and dsRNA depletion formulated into LNPs.

A dose response of LNPs formulated with PCSK9 mega-TAL and Trex2 mRNAs purified by polyA isolation and dsRNA depletion was performed to measure the effects of dose on in vivo bulk liver editing rates. LNPs were formulated as described in Example 5 with PCSK9 megaTAL and Trex2 mRNA at a 1.0:1.0 molar ratio. Five animals were treated at each dose (0.3, 1.0 and 3.0 mg/kg mRNA) or using PBS as a negative control. The % INDEL rate was quantified from bulk liver tissue as described in Example 5. The average INDEL rate was plotted for all animals from all conditions (FIG. 10, right panel). A dose dependent increase in % INDELs at the PCSK9 was observed.

Example 8

Serum PCSK9 and Serum Cholesterol Levels in Mice Treated with LNPs Formulated with PCSK9 MegaTAL and Trex2 mRNAs Serum PCSK9 and serum cholesterol levels were measured in the mice treated with LNPs formulated with PCSK9 megaTAL mRNA and Trex2 mRNA (Example 7).

Mouse livers were isolated 96 hours post-treatment, fixed in 10% neutral buffered formalin for 24 hours, embedded in paraffin, and sectioned for in situ hybridization (ISH). Mouse PCSK9 mRNA was detected in liver sections using Advanced Cell Diagnostics RNAscope ISH method. To check for RNA integrity, a probe against the mouse PPIB or DAPB genes were used and as a negative control. A clear dose dependent reduction in PCSK9 mRNA signal was observed in mice treated with increasing amounts of PCSK9 megaTAL and Trex2 (FIG. 11A). ISH images of the liver were automatically digitally quantified using HALO software (FIG. 11B) and displayed as average number of probes per cell (FIG. 11C).

Serum cholesterol was collected from animals 96 hours after mRNA administration and circulating PCSK9 protein was quantified using R&D systems Mouse PCSK9 Quantikine ELISA kit (Cat #: MPC900) following the manufacturers recommended protocol. A clear dose dependent reduction in PCSK9 protein was observed in mice treated with 1.0 and 3.0 mg/ml of formulated PCSK9 megaTAL and Trex2 mRNA compared to control treated mice (FIG. 11D), and was highly correlated with the % average INDEL rates for each dose (FIG. 11E). Mice treated with 1.0 and 3.0 mg/ml of PCSK9 megaTAL and Trex2 mRNA showed significant reductions in serum cholesterol compared to control treated mice (FIG. 11F), which were highly correlated with the % average INDEL rate for each dose (FIG. 11G). Long term editing was determined by serially sampling serum PCSK9 and cholesterol in a separate cohort of animals (n=5) dosed with LNPs formulated with 1 mg/kg of PCSK9 megaTAL and Trex2 mRNA (FIGS. 11H and 11I).

Edited hepatocytes and decreased serum PCSK9 protein and cholesterol levels persisted throughout the 6-week duration of the study.

Example 9

Figure 12B:
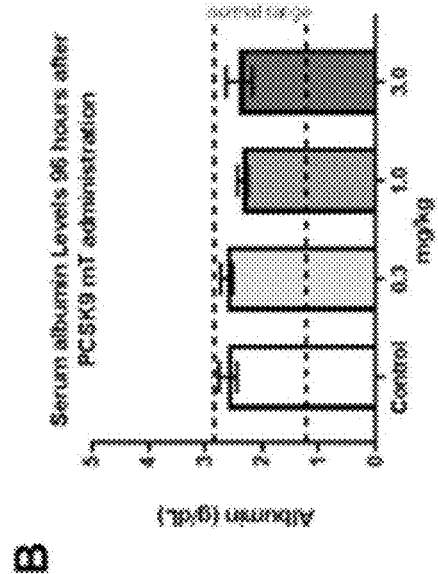
FIGS. 12A-12C show serum transaminase (aspartate aminotransferase (AST)) and albumin levels in the mice treated in Example 7.
Figure 12A:
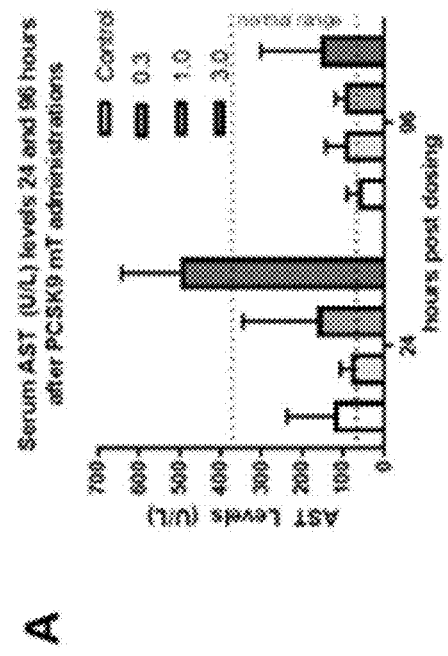

Liver Toxicity is not Associated with LNPs Formulated with PCSK9 MegaTAL and Trex2 mRNAs Mandibular bleeds were collected from mice administered PCSK9 megaTAL and Trex2 mRNA (Example 7) at 24 hours and 94 hours post-administration. Aspartate aminotransferase (AST) enzyme levels were less than two-fold different from baseline at low mRNA doses at 24 hours, and had returned to baseline levels for all doses by 96 hours post-administration (FIG. 12A). Serum albumin levels in mice treated with PCSK9 megaTAL and Trex2 mRNA were unchanged at 96 hours post-administration compared to control treated mice, indicating that liver function was normal in the treatment groups.

Figure 12C:
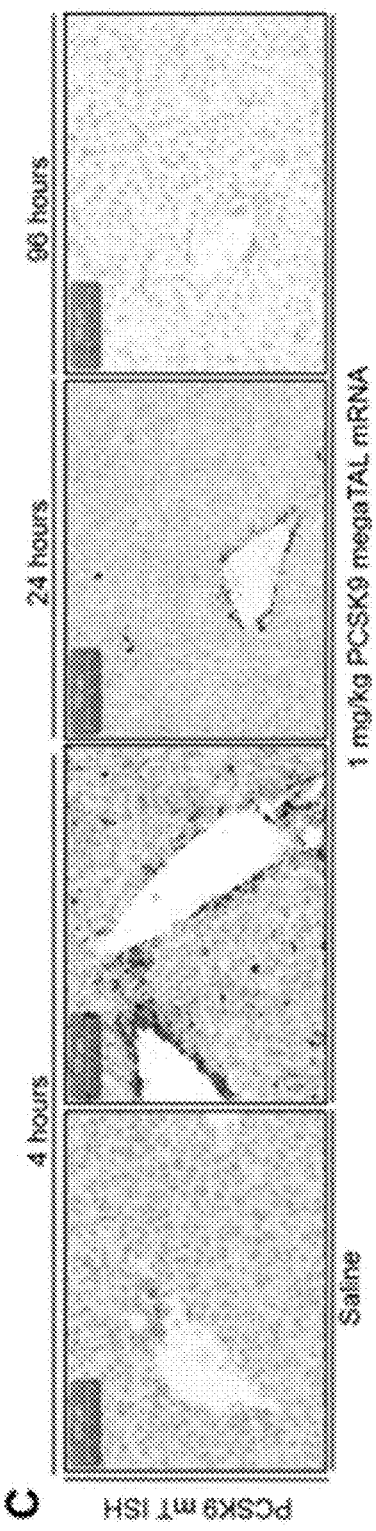

PCSK9 megaTAL mRNA persistence was measured using ISH using the Advanced Cell Diagnostics RNAscope ISH method. PCSK9 megaTAL mRNA was assayed in sections at 4, 24, and 96 hours post dosing (FIG. 12C). PCSK9 megaTAL mRNA was expressed at relatively high levels 4 post-administration; levels decreased and were undetectable by 96 hours post-administration.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A polypeptide comprising a I-Onul homing endonuclease (HE) variant that cleaves a target site in a proprotein convertase subtilisin/kexin type 9 (PCSK9) gene,
   wherein the target site is SEQ ID NO: 11, and
   wherein the I-Onul HE variant comprises an amino acid sequence that has at least 90% sequence identical identity to the amino acid sequence set forth in any one of SEQ ID NOs: 6-7.

2. The polypeptide of claim 1, wherein the I-Onul HE variant lacks:
   (a) the 1, 2, 3, 4, 5, 6, 7, or 8 N-terminal amino acids compared to a corresponding wild type I-Onul LAGLIDADG homing endonuclease (LHE) comprising the amino acid sequence of SEQ ID NO: 2;
   (b) the 4 N-terminal amino acids compared to a corresponding wild type I-Onul LHE comprising the amino acid sequence of SEQ ID NO: 2;
   (c) the 8 N-terminal amino acids compared to a corresponding wild type I-Onul LHE comprising the amino acid sequence of SEQ ID NO: 2;
   (d) the 1, 2, 3, 4, or 5 C-terminal amino acids compared to a corresponding wild type I-Onul LHE comprising the amino acid sequence of SEQ ID NO: 2;
   (e) the C-terminal amino acid compared to a corresponding wild type I-Onul LHE comprising the amino acid sequence of SEQ ID NO: 2; and/or
   (f) the 2 C-terminal amino acids compared to a corresponding wild type I-Onul LHE comprising the amino acid sequence of SEQ ID NO: 2.

3. The polypeptide of claim 1, wherein the I-Onul HE variant cleaves a PCSK9 target site and comprises the following amino acid substitutions:
   a) S24C, L26M, R28N, R30W, N32K, K34R, S35T, S36R, V37A, G38K, S40Y, E42A, G44R, Q46E, T48A, Q61R, V68K, A70R, S72I, N75R, A76V, S78K, K80V, T82G, V116L, L138M, T143N, S159P, F168L, E178D, C180Y, F182G, N184E, I186M, S188R, K189T, S190T, K191G, L192T, G193H, Q195T, Q197R, V199R, T203A, K207R, Y223R, K225S, K227R, F232Y, and D236E of any one of SEQ ID NOs: 1-5;
   b) S24C, L26M, R28N, R30W, N32K, K34R, S35T, S36R, V37A, G38K, S40Y, E42A, G44R, Q46E, T48A, Q61R, V68K, A70R, S72I, N75R, A76V, S78K, K80V, T82G, V116L, L138M, T143N, S159P, F168L, E178D, C180Y, F182G, N184E, I186M, S188R, S190T, K191G, L192T, G193H, Q195T, Q197R, V199R, T203A, K207R, Y223R, K225S, K227R, F232Y, and D236E of any one of SEQ ID NOs: 1-5; or
   c) S24C, L26M, R28N, R30W, N32K, K34R, S35T, S36R, V37A, G38K, S40Y, E42A, G44R, Q46E, T48A, Q61R, V68K, A70R, S72I, N75R, A76V, S78K, K80V, T82G, V116L, L138M, T143N, S159P, F168L, E178D, C180Y, F182G, N184E, I186M, S188R, K189T, S190T, K191G, L192T, G193H, Q195T, Q197R, V199R, K207R, Y223R, K225S, K227R, F232Y, and D236E of any one of SEQ ID NOs: 1-5.

4. The polypeptide of claim 1, wherein the I-Onul HE variant comprises an amino acid sequence that has at least 95% sequence identity to the amino acid sequence set forth in any one of SEQ ID NOS: 6-7.

5. The polypeptide of claim 1, wherein the I-Onul HE variant comprises the amino acid sequence set forth in SEQ ID NO: 6 or SEQ ID NO: 7.

6. The polypeptide of claim 1, further comprising a transcription activator-like effectors (TALE) DNA binding domain.

7. The polypeptide of claim 6, wherein the TALE DNA binding domain comprises about 9.5 TALE repeat units to about 15.5 TALE repeat units.

8. The polypeptide of claim 6, wherein the TALE DNA binding domain binds the PCSK9 polynucleotide sequence set forth in SEQ ID NO: 13.

9. The polypeptide of claim 1, further comprising a peptide linker and an end-processing enzyme.

10. The polypeptide of claim 9, wherein the end-processing enzyme comprises Trex2.

11. The polypeptide of claim 1, wherein the polypeptide comprises the amino acid sequence set forth in SEQ ID NO: 8 or SEQ ID NO: 9.

12. A polynucleotide, mRNA, cDNA, or vector encoding the polypeptide of claim 1.

13. A composition comprising a lipid nanoparticle comprising:
   (a) an mRNA encoding a polypeptide of claim 1; and
   (b) an mRNA encoding Trex2.

14. A lipid nanoparticle comprising:
   (a) an mRNA encoding a polypeptide of claim 1; and
   (b) an mRNA encoding Trex2.

15. A composition comprising a lipid nanoparticle comprising:
   (a) an mRNA encoding a polypeptide of claim 1; and
   (b) an mRNA encoding Trex2.

* * * * *

```
                         SEQUENCE LISTING

<160> NUMBER OF SEQ ID NOS: 67

<210> SEQ ID NO 1
<211> LENGTH: 303
<212> TYPE: PRT
<213> ORGANISM: Ophiostoma novo-ulmi

<400> SEQUENCE: 1

Met Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Met Leu Phe Lys Gln
            100                 105                 110

Ala Phe Cys Val Met Glu Asn Lys Glu His Leu Lys Ile Asn Gly Ile
        115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Ile Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255
```

```
Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 2
<211> LENGTH: 303
<212> TYPE: PRT
<213> ORGANISM: Ophiostoma novo-ulmi

<400> SEQUENCE: 2

Met Ala Tyr Met Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
        35                  40                  45

Leu His Asn Lys Asp Lys Ser Ile Leu Glu Asn Ile Gln Ser Thr Trp
    50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
            100                 105                 110

Ala Phe Ser Val Met Glu Asn Lys Glu His Leu Lys Glu Asn Gly Ile
        115                 120                 125

Lys Glu Leu Val Arg Ile Lys Ala Lys Leu Asn Trp Gly Leu Thr Asp
    130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
            180                 185                 190

Gly Val Gln Val Gln Leu Val Phe Ser Ile Thr Gln His Ile Lys Asp
        195                 200                 205

Lys Asn Leu Met Asn Ser Leu Ile Thr Tyr Leu Gly Cys Gly Tyr Ile
    210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
        275                 280                 285

Glu Ile Lys Lys Ile Lys Leu Asn Met Asn Lys Gly Arg Val Phe
    290                 295                 300

<210> SEQ ID NO 3
<211> LENGTH: 303
<212> TYPE: PRT
<213> ORGANISM: Ophiostoma novo-ulmi
```

```
<220> FEATURE:
<221> NAME/KEY: MOD_RES
<222> LOCATION: (1)..(3)
<223> OTHER INFORMATION: Any amino acid or absent

<400> SEQUENCE: 3
```

| | | | | | | | | | | | | | | |
|---|---|---|---|---|---|---|---|---|---|---|---|---|---|---|
| Xaa | Xaa | Xaa | Met | Ser | Arg | Arg | Glu | Ser | Ile | Asn | Pro | Trp | Ile | Leu | Thr |
| 1 | | | | 5 | | | | | 10 | | | | | 15 |
| Gly | Phe | Ala | Asp | Ala | Glu | Gly | Ser | Phe | Leu | Leu | Arg | Ile | Arg | Asn | Asn |
| | | | 20 | | | | | 25 | | | | | 30 | |
| Asn | Lys | Ser | Ser | Val | Gly | Tyr | Ser | Thr | Glu | Leu | Gly | Phe | Gln | Ile | Thr |
| | | 35 | | | | | 40 | | | | | 45 | | |
| Leu | His | Asn | Lys | Asp | Lys | Ser | Ile | Leu | Glu | Asn | Ile | Gln | Ser | Thr | Trp |
| 50 | | | | | 55 | | | | | 60 | | | | | |
| Lys | Val | Gly | Val | Ile | Ala | Asn | Ser | Gly | Asp | Asn | Ala | Val | Ser | Leu | Lys |
| 65 | | | | | 70 | | | | | 75 | | | | | 80 |
| Val | Thr | Arg | Phe | Glu | Asp | Leu | Lys | Val | Ile | Ile | Asp | His | Phe | Glu | Lys |
| | | | | 85 | | | | | 90 | | | | | 95 | |
| Tyr | Pro | Leu | Ile | Thr | Gln | Lys | Leu | Gly | Asp | Tyr | Lys | Leu | Phe | Lys | Gln |
| | | | 100 | | | | | 105 | | | | | 110 | | |
| Ala | Phe | Ser | Val | Met | Glu | Asn | Lys | Glu | His | Leu | Lys | Glu | Asn | Gly | Ile |
| | | 115 | | | | | 120 | | | | | 125 | | | |
| Lys | Glu | Leu | Val | Arg | Ile | Lys | Ala | Lys | Leu | Asn | Trp | Gly | Leu | Thr | Asp |
| 130 | | | | | 135 | | | | | 140 | | | | | |
| Glu | Leu | Lys | Lys | Ala | Phe | Pro | Glu | Asn | Ile | Ser | Lys | Glu | Arg | Ser | Leu |
| 145 | | | | | 150 | | | | | 155 | | | | | 160 |
| Ile | Asn | Lys | Asn | Ile | Pro | Asn | Phe | Lys | Trp | Leu | Ala | Gly | Phe | Thr | Ser |
| | | | | 165 | | | | | 170 | | | | | 175 | |
| Gly | Glu | Gly | Cys | Phe | Phe | Val | Asn | Leu | Ile | Lys | Ser | Lys | Ser | Lys | Leu |
| | | | 180 | | | | | 185 | | | | | 190 | | |
| Gly | Val | Gln | Val | Gln | Leu | Val | Phe | Ser | Ile | Thr | Gln | His | Ile | Lys | Asp |
| | | 195 | | | | | 200 | | | | | 205 | | | |
| Lys | Asn | Leu | Met | Asn | Ser | Leu | Ile | Thr | Tyr | Leu | Gly | Cys | Gly | Tyr | Ile |
| 210 | | | | | 215 | | | | | 220 | | | | | |
| Lys | Glu | Lys | Asn | Lys | Ser | Glu | Phe | Ser | Trp | Leu | Asp | Phe | Val | Val | Thr |
| 225 | | | | | 230 | | | | | 235 | | | | | 240 |
| Lys | Phe | Ser | Asp | Ile | Asn | Asp | Lys | Ile | Ile | Pro | Val | Phe | Gln | Glu | Asn |
| | | | | 245 | | | | | 250 | | | | | 255 | |
| Thr | Leu | Ile | Gly | Val | Lys | Leu | Glu | Asp | Phe | Glu | Asp | Trp | Cys | Lys | Val |
| | | | 260 | | | | | 265 | | | | | 270 | | |
| Ala | Lys | Leu | Ile | Glu | Glu | Lys | Lys | His | Leu | Thr | Glu | Ser | Gly | Leu | Asp |
| | | 275 | | | | | 280 | | | | | 285 | | | |
| Glu | Ile | Lys | Lys | Ile | Lys | Leu | Asn | Met | Asn | Lys | Gly | Arg | Val | Phe | |
| 290 | | | | | 295 | | | | | 300 | | | | | |

```
<210> SEQ ID NO 4
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 4
```

Xaa Xaa Xaa Xaa Ser Arg Arg Glu Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
            35                  40                  45

Leu His Asn Lys Asp Lys Ser Ile Leu Glu Asn Ile Gln Ser Thr Trp
50                  55                  60

Lys Val Gly Val Ile Ala Asn Ser Gly Asp Asn Ala Val Ser Leu Lys
65                  70                  75                  80

Val Thr Arg Phe Glu Asp Leu Lys Val Ile Ile Asp His Phe Glu Lys
                85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
                115                 120                 125

Lys Glu Leu Val Arg Ile Lys Ala Lys Leu Asn Trp Gly Leu Thr Asp
130                 135                 140

Glu Leu Lys Lys Ala Phe Pro Glu Asn Ile Ser Lys Gly Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Lys Ser Lys Leu
                180                 185                 190

Gly Val Gln Val Gln Leu Val Phe Ser Ile Thr Gln His Ile Lys Asp
                195                 200                 205

Lys Asn Leu Met Asn Ser Leu Ile Thr Tyr Leu Gly Cys Gly Tyr Ile
210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Asp Trp Cys Lys Val
                260                 265                 270

Ala Lys Leu Ile Glu Glu Lys Lys His Leu Thr Glu Ser Gly Leu Asp
                275                 280                 285

Glu Ile Lys Lys Ile Lys Leu Asn Met Asn Lys Gly Arg Xaa Xaa
                290                 295                 300

<210> SEQ ID NO 5
<211> LENGTH: 303
<212> TYPE: PRT
<213> ORGANISM: Ophiostoma novo-ulmi
<220> FEATURE:
<221> NAME/KEY: MOD_RES
<222> LOCATION: (1)..(8)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 5

Xaa Xaa Xaa Xaa Xaa Xaa Xaa Xaa Ser Ile Asn Pro Trp Ile Leu Thr
1               5                   10                  15

Gly Phe Ala Asp Ala Glu Gly Ser Phe Leu Leu Arg Ile Arg Asn Asn
            20                  25                  30

Asn Lys Ser Ser Val Gly Tyr Ser Thr Glu Leu Gly Phe Gln Ile Thr
             35                  40                  45

Leu His Asn Lys Asp Lys Ser Ile Leu Glu Asn Ile Gln Ser Thr Trp
 50                  55                  60

Lys Val Gly Val Ile Ala Asn Ser Gly Asp Asn Ala Val Ser Leu Lys
 65                  70                  75                  80

Val Thr Arg Phe Glu Asp Leu Lys Val Ile Asp His Phe Glu Lys
                 85                  90                  95

Tyr Pro Leu Ile Thr Gln Lys Leu Gly Asp Tyr Lys Leu Phe Lys Gln
                100                 105                 110

Ala Phe Ser Val Met Glu Asn Lys Glu His Leu Lys Glu Asn Gly Ile
            115                 120                 125

Lys Glu Leu Val Arg Ile Lys Ala Lys Leu Asn Trp Gly Leu Thr Asp
            130                 135                 140

Glu Leu Lys Lys Ala Phe Pro Glu Asn Ile Ser Lys Glu Arg Ser Leu
145                 150                 155                 160

Ile Asn Lys Asn Ile Pro Asn Phe Lys Trp Leu Ala Gly Phe Thr Ser
                165                 170                 175

Gly Glu Gly Cys Phe Phe Val Asn Leu Ile Lys Ser Ser Lys Leu
            180                 185                 190

Gly Val Gln Val Gln Leu Val Phe Ser Ile Thr Gln His Ile Lys Asp
            195                 200                 205

Lys Asn Leu Met Asn Ser Leu Ile Thr Tyr Leu Gly Cys Gly Tyr Ile
            210                 215                 220

Lys Glu Lys Asn Lys Ser Glu Phe Ser Trp Leu Asp Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
            260                 265                 270

Ala Lys Leu Ile Glu Glu Lys Lys His Leu Thr Glu Ser Gly Leu Asp
            275                 280                 285

Glu Ile Lys Lys Ile Lys Leu Asn Met Asn Lys Gly Arg Xaa Xaa
            290                 295                 300

<210> SEQ ID NO 6
<211> LENGTH: 303
<212> TYPE: PRT
<213> ORGANISM: Artificial Sequence
<220> FEATURE:
<223> OTHER INFORMATION: Synthesized I-OnuI variant PCSK9.H7
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 6

Xaa Xaa Xaa Xaa Ser Arg Arg Glu Ser Ile Asn Pro Trp Ile Leu Thr
 1               5                  10                  15

Gly Phe Ala Asp Ala Glu Gly Cys Phe Met Leu Asn Ile Trp Asn Lys
                 20                  25                  30

Asn Arg Thr Arg Ala Lys Tyr Tyr Thr Ala Leu Arg Phe Glu Ile Ala
             35                  40                  45

```
Leu His Asn Lys Asp Lys Ser Ile Leu Glu Asn Ile Arg Ser Thr Trp
 50                  55                  60

Lys Val Gly Lys Ile Arg Asn Ile Gly Asp Arg Val Val Lys Leu Val
 65                  70                  75                  80

Val Gly Arg Phe Glu Asp Leu Lys Val Ile Asp His Phe Glu Lys
                     85                  90                  95

Tyr Pro Leu Ile Thr Gln Lys Leu Gly Asp Tyr Lys Leu Phe Lys Gln
                 100                 105                 110

Ala Phe Ser Leu Met Glu Asn Lys Glu His Leu Lys Glu Asn Gly Ile
             115                 120                 125

Lys Glu Leu Val Arg Ile Lys Ala Lys Met Asn Trp Gly Leu Asn Asp
130                 135                 140

Glu Leu Lys Lys Ala Phe Pro Glu Asn Ile Ser Lys Glu Arg Pro Leu
145                 150                 155                 160

Ile Asn Lys Asn Ile Pro Asn Leu Lys Trp Leu Ala Gly Phe Thr Ser
                165                 170                 175

Gly Asp Gly Tyr Phe Gly Val Glu Leu Met Lys Arg Lys Thr Gly Thr
                180                 185                 190

His Val Thr Val Arg Leu Arg Phe Ser Ile Ala Gln His Ile Arg Asp
                195                 200                 205

Lys Asn Leu Met Asn Ser Leu Ile Thr Tyr Leu Gly Cys Gly Arg Ile
210                 215                 220

Ser Glu Arg Asn Lys Ser Glu Tyr Ser Trp Leu Glu Phe Val Val Thr
225                 230                 235                 240

Lys Phe Ser Asp Ile Asn Asp Lys Ile Ile Pro Val Phe Gln Glu Asn
                245                 250                 255

Thr Leu Ile Gly Val Lys Leu Glu Asp Phe Glu Asp Trp Cys Lys Val
                260                 265                 270

Ala Lys Leu Ile Glu Glu Lys Lys His Leu Thr Glu Ser Gly Leu Asp
                275                 280                 285

Glu Ile Lys Lys Ile Lys Leu Asn Met Asn Lys Gly Arg Xaa Xaa
                290                 295                 300
```

<210> SEQ ID NO 7
<211> LENGTH: 303
<212> TYPE: PRT
<213> ORGANISM: Artificial Sequence
<220> FEATURE:
<223> OTHER INFORMATION: Synthesized I-OnuI variant PCSK9.H7.C11
<220> FEATURE:
<221> NAME/KEY: MOD_RES
<222> LOCATION: (1)..(4)
<223> OTHER INFORMATION: Any amino acid or absent
<220> FEATURE:
<221> NAME/KEY: MOD_RES
<222> LOCATION: (302)..(303)
<223> OTHER INFORMATION: Any amino acid or absent

<400> SEQUENCE: 7

```
Xaa Xaa Xaa Xaa Ser Arg Arg Glu Ser Ile Asn Pro Trp Ile Leu Thr
 1               5                  10                  15

Gly Phe Ala Asp Ala Glu Gly Cys Phe Met Leu Asn Ile Trp Asn Lys
                 20                  25                  30

Asn Arg Thr Arg Ala Lys Tyr Tyr Thr Ala Leu Arg Phe Glu Ile Ala
                 35                  40                  45

Leu His Asn Lys Asp Lys Ser Ile Leu Glu Asn Ile Arg Ser Thr Trp
 50                  55                  60

Lys Val Gly Lys Ile Arg Asn Ile Gly Asp Arg Val Val Lys Leu Val
```

```
                65                  70                  75                  80
        Val Gly Arg Phe Glu Asp Leu Lys Val Ile Ile Asp His Phe Glu Lys
                            85                  90                  95

Tyr Pro Leu Ile Thr Gln Lys Leu Gly Asp Tyr Lys Leu Phe Lys Gln
                           100                 105                 110

Ala Phe Ser Leu Met Glu Asn Lys Glu His Leu Lys Glu Asn Gly Ile
                           115                 120                 125

Lys Glu Leu Val Arg Ile Lys Ala Lys Met Asn Trp Gly Leu Asn Asp
                130                 135                 140

Glu Leu Lys Lys Ala Phe Pro Glu Asn Ile Ser Lys Glu Arg Pro Leu
        145                 150                 155                 160

Ile Asn Lys Asn Ile Pro Asn Leu Lys Trp Leu Ala Gly Phe Thr Ser
                           165                 170                 175

Gly Asp Gly Tyr Phe Gly Val Glu Leu Met Lys Arg Thr Thr Gly Thr
                           180                 185                 190

His Val Thr Val Arg Leu Arg Phe Ser Ile Thr Gln His Ile Arg Asp
                           195                 200                 205

Lys Asn Leu Met Asn Ser Leu Ile Thr Tyr Leu Gly Cys Gly Arg Ile
                210                 215                 220

Ser Glu Arg Asn Lys Ser Glu Tyr Ser Trp Leu Glu Phe Val Val Thr
        225                 230                 235                 240

Lys Phe Ser Asp Ile Asn Asp Lys Ile Ile Pro Val Phe Gln Glu Asn
                           245                 250                 255

Thr Leu Ile Gly Val Lys Leu Glu Asp Phe Glu Asp Trp Cys Lys Val
                           260                 265                 270

Ala Lys Leu Ile Glu Glu Lys Lys His Leu Thr Glu Ser Gly Leu Asp
                           275                 280                 285

Glu Ile Lys Lys Ile Lys Leu Asn Met Asn Lys Gly Arg Xaa Xaa
                290                 295                 300

<210> SEQ ID NO 8
<211> LENGTH: 978
<212> TYPE: PRT
<213> ORGANISM: Artificial Sequence
<220> FEATURE:
<223> OTHER INFORMATION: Made in Lab - synthesized megaTAL PCSK9.H7
      construct

<400> SEQUENCE: 8

Met Gly Ser Cys Arg Pro Pro Lys Lys Arg Lys Val Val Asp Leu
        1               5                   10                  15

Arg Thr Leu Gly Tyr Ser Gln Gln Gln Gln Glu Lys Ile Lys Pro Lys
                            20                  25                  30

Val Arg Ser Thr Val Ala Gln His His Glu Ala Leu Val Gly His Gly
                            35                  40                  45

Phe Thr His Ala His Ile Val Ala Leu Ser Gln His Pro Ala Ala Leu
                50                  55                  60

Gly Thr Val Ala Val Thr Tyr Gln His Ile Ile Thr Ala Leu Pro Glu
        65                  70                  75                  80

Ala Thr His Glu Asp Ile Val Gly Val Gly Lys Gln Trp Ser Gly Ala
                            85                  90                  95

Arg Ala Leu Glu Ala Leu Leu Thr Asp Ala Gly Glu Leu Arg Gly Pro
                           100                 105                 110

Pro Leu Gln Leu Asp Thr Gly Gln Leu Val Lys Ile Ala Lys Arg Gly
                           115                 120                 125
```

-continued

```
Gly Val Thr Ala Met Glu Ala Val His Ala Ser Arg Asn Ala Leu Thr
130                 135                 140

Gly Ala Pro Leu Asn Leu Thr Pro Asp Gln Val Val Ala Ile Ala Ser
145                 150                 155                 160

Asn Asn Gly Gly Lys Gln Ala Leu Glu Thr Val Gln Arg Leu Leu Pro
                165                 170                 175

Val Leu Cys Gln Asp His Gly Leu Thr Pro Asp Gln Val Val Ala Ile
            180                 185                 190

Ala Ser Asn Asn Gly Gly Lys Gln Ala Leu Glu Thr Val Gln Arg Leu
        195                 200                 205

Leu Pro Val Leu Cys Gln Asp His Gly Leu Thr Pro Asp Gln Val Val
210                 215                 220

Ala Ile Ala Ser Asn Asn Gly Gly Lys Gln Ala Leu Glu Thr Val Gln
225                 230                 235                 240

Arg Leu Leu Pro Val Leu Cys Gln Asp His Gly Leu Thr Pro Asp Gln
                245                 250                 255

Val Val Ala Ile Ala Ser His Asp Gly Gly Lys Gln Ala Leu Glu Thr
            260                 265                 270

Val Gln Arg Leu Leu Pro Val Leu Cys Gln Asp His Gly Leu Thr Pro
        275                 280                 285

Asp Gln Val Val Ala Ile Ala Ser Asn Ile Gly Gly Lys Gln Ala Leu
290                 295                 300

Glu Thr Val Gln Arg Leu Leu Pro Val Leu Cys Gln Asp His Gly Leu
305                 310                 315                 320

Thr Pro Asp Gln Val Val Ala Ile Ala Ser His Asp Gly Gly Lys Gln
                325                 330                 335

Ala Leu Glu Thr Val Gln Arg Leu Leu Pro Val Leu Cys Gln Asp His
            340                 345                 350

Gly Leu Thr Pro Asp Gln Val Val Ala Ile Ala Ser His Asp Gly Gly
        355                 360                 365

Lys Gln Ala Leu Glu Thr Val Gln Arg Leu Leu Pro Val Leu Cys Gln
370                 375                 380

Asp His Gly Leu Thr Pro Asp Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Asp His Gly Leu Thr Pro Asp Gln Val Val Ala Ile Ala Ser
            420                 425                 430

Asn Gly Gly Gly Lys Gln Ala Leu Glu Thr Val Gln Arg Leu Leu Pro
        435                 440                 445

Val Leu Cys Gln Asp His Gly Leu Thr Pro Asp Gln Val Val Ala Ile
450                 455                 460

Ala Ser Asn Asn Gly Gly Lys Gln Ala Leu Glu Thr Val Gln Arg Leu
465                 470                 475                 480

Leu Pro Val Leu Cys Gln Asp His Gly Leu Thr Pro Asp Gln Val Val
                485                 490                 495

Ala Ile Ala Ser Asn Asn Gly Gly Lys Gln Ala Leu Glu Thr Val Gln
            500                 505                 510

Arg Leu Leu Pro Val Leu Cys Gln Asp His Gly Leu Thr Pro Asp Gln
        515                 520                 525

Val Val Ala Ile Ala Ser Asn Ile Gly Gly Lys Gln Ala Leu Glu Thr
530                 535                 540

Val Gln Arg Leu Leu Pro Val Leu Cys Gln Asp His Gly Leu Thr Pro
```

```
            545                 550                 555                 560
Asp Gln Val Val Ala Ile Ala Ser Asn Gly Gly Lys Gln Ala Leu
                565                 570                 575
Glu Thr Val Gln Arg Leu Leu Pro Val Leu Cys Gln Asp His Gly Leu
                580                 585                 590
Thr Pro Asp Gln Val Val Ala Ile Ala Ser Asn Asn Gly Gly Lys Gln
                595                 600                 605
Ala Leu Glu Ser Ile Val Ala Gln Leu Ser Arg Pro Asp Pro Ala Leu
            610                 615                 620
Ala Ala Leu Thr Asn Asp His Leu Val Ala Leu Ala Cys Leu Gly Gly
625                 630                 635                 640
Arg Pro Ala Met Asp Ala Val Lys Lys Gly Leu Pro His Ala Pro Glu
                645                 650                 655
Leu Ile Arg Arg Val Asn Arg Arg Ile Gly Glu Arg Thr Ser His Arg
                660                 665                 670
Val Ala Ile Ser Arg Val Gly Gly Ser Ser Arg Arg Glu Ser Ile Asn
            675                 680                 685
Pro Trp Ile Leu Thr Gly Phe Ala Asp Ala Glu Gly Cys Phe Met Leu
690                 695                 700
Asn Ile Trp Asn Lys Asn Arg Thr Arg Ala Lys Tyr Tyr Thr Ala Leu
705                 710                 715                 720
Arg Phe Glu Ile Ala Leu His Asn Lys Asp Lys Ser Ile Leu Glu Asn
                725                 730                 735
Ile Arg Ser Thr Trp Lys Val Gly Lys Ile Arg Asn Ile Gly Asp Arg
                740                 745                 750
Val Val Lys Leu Val Val Gly Arg Phe Glu Asp Leu Lys Val Ile Ile
            755                 760                 765
Asp His Phe Glu Lys Tyr Pro Leu Ile Thr Gln Lys Leu Gly Asp Tyr
            770                 775                 780
Lys Leu Phe Lys Gln Ala Phe Ser Leu Met Glu Asn Lys Glu His Leu
785                 790                 795                 800
Lys Glu Asn Gly Ile Lys Glu Leu Val Arg Ile Lys Ala Lys Met Asn
                805                 810                 815
Trp Gly Leu Asn Asp Glu Leu Lys Lys Ala Phe Pro Glu Asn Ile Ser
                820                 825                 830
Lys Glu Arg Pro Leu Ile Asn Lys Asn Ile Pro Asn Leu Lys Trp Leu
                835                 840                 845
Ala Gly Phe Thr Ser Gly Asp Gly Tyr Phe Gly Val Glu Leu Met Lys
            850                 855                 860
Arg Lys Thr Gly Thr His Val Thr Val Arg Leu Arg Phe Ser Ile Ala
865                 870                 875                 880
Gln His Ile Arg Asp Lys Asn Leu Met Asn Ser Leu Ile Thr Tyr Leu
                885                 890                 895
Gly Cys Gly Arg Ile Ser Glu Arg Asn Lys Ser Glu Tyr Ser Trp Leu
                900                 905                 910
Glu Phe Val Val Thr Lys Phe Ser Asp Ile Asn Asp Lys Ile Ile Pro
            915                 920                 925
Val Phe Gln Glu Asn Thr Leu Ile Gly Val Lys Leu Glu Asp Phe Glu
            930                 935                 940
Asp Trp Cys Lys Val Ala Lys Leu Ile Glu Glu Lys Lys His Leu Thr
945                 950                 955                 960
Glu Ser Gly Leu Asp Glu Ile Lys Lys Ile Lys Leu Asn Met Asn Lys
                965                 970                 975
```

Gly Arg

<210> SEQ ID NO 9
<211> LENGTH: 978
<212> TYPE: PRT
<213> ORGANISM: Artificial Sequence
<220> FEATURE:
<223> OTHER INFORMATION: Made in Lab - synthesized megaTAL PCSK9.H7.C11
      construct

<400> SEQUENCE: 9

```
Met Gly Ser Cys Arg Pro Pro Lys Lys Arg Lys Val Val Asp Leu
1               5                  10                  15

Arg Thr Leu Gly Tyr Ser Gln Gln Gln Glu Lys Ile Lys Pro Lys
            20                  25                  30

Val Arg Ser Thr Val Ala Gln His His Glu Ala Leu Val Gly His Gly
        35                  40                  45

Phe Thr His Ala His Ile Val Ala Leu Ser Gln His Pro Ala Ala Leu
    50                  55                  60

Gly Thr Val Ala Val Thr Tyr Gln His Ile Ile Thr Ala Leu Pro Glu
65                  70                  75                  80

Ala Thr His Glu Asp Ile Val Gly Val Gly Lys Gln Trp Ser Gly Ala
                85                  90                  95

Arg Ala Leu Glu Ala Leu Leu Thr Asp Ala Gly Glu Leu Arg Gly Pro
            100                 105                 110

Pro Leu Gln Leu Asp Thr Gly Gln Leu Val Lys Ile Ala Lys Arg Gly
        115                 120                 125

Gly Val Thr Ala Met Glu Ala Val His Ala Ser Arg Asn Ala Leu Thr
130                 135                 140

Gly Ala Pro Leu Asn Leu Thr Pro Asp Gln Val Val Ala Ile Ala Ser
145                 150                 155                 160

Asn Asn Gly Gly Lys Gln Ala Leu Glu Thr Val Gln Arg Leu Leu Pro
                165                 170                 175

Val Leu Cys Gln Asp His Gly Leu Thr Pro Asp Gln Val Val Ala Ile
            180                 185                 190

Ala Ser Asn Asn Gly Gly Lys Gln Ala Leu Glu Thr Val Gln Arg Leu
        195                 200                 205

Leu Pro Val Leu Cys Gln Asp His Gly Leu Thr Pro Asp Gln Val Val
    210                 215                 220

Ala Ile Ala Ser Asn Asn Gly Gly Lys Gln Ala Leu Glu Thr Val Gln
225                 230                 235                 240

Arg Leu Leu Pro Val Leu Cys Gln Asp His Gly Leu Thr Pro Asp Gln
                245                 250                 255

Val Val Ala Ile Ala Ser His Asp Gly Gly Lys Gln Ala Leu Glu Thr
            260                 265                 270

Val Gln Arg Leu Leu Pro Val Leu Cys Gln Asp His Gly Leu Thr Pro
        275                 280                 285

Asp Gln Val Val Ala Ile Ala Ser Asn Ile Gly Gly Lys Gln Ala Leu
    290                 295                 300

Glu Thr Val Gln Arg Leu Leu Pro Val Leu Cys Gln Asp His Gly Leu
305                 310                 315                 320

Thr Pro Asp Gln Val Val Ala Ile Ala Ser His Asp Gly Gly Lys Gln
                325                 330                 335

Ala Leu Glu Thr Val Gln Arg Leu Leu Pro Val Leu Cys Gln Asp His
            340                 345                 350
```

```
Gly Leu Thr Pro Asp Gln Val Ala Ile Ala Ser His Asp Gly Gly
        355                 360                 365

Lys Gln Ala Leu Glu Thr Val Gln Arg Leu Leu Pro Val Leu Cys Gln
    370                 375                 380

Asp His Gly Leu Thr Pro Asp Gln Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Asp His Gly Leu Thr Pro Asp Gln Val Val Ala Ile Ala Ser
                420                 425                 430

Asn Gly Gly Gly Lys Gln Ala Leu Glu Thr Val Gln Arg Leu Leu Pro
            435                 440                 445

Val Leu Cys Gln Asp His Gly Leu Thr Pro Asp Gln Val Val Ala Ile
        450                 455                 460

Ala Ser Asn Asn Gly Gly Lys Gln Ala Leu Glu Thr Val Gln Arg Leu
465                 470                 475                 480

Leu Pro Val Leu Cys Gln Asp His Gly Leu Thr Pro Asp Gln Val Val
                485                 490                 495

Ala Ile Ala Ser Asn Asn Gly Gly Lys Gln Ala Leu Glu Thr Val Gln
            500                 505                 510

Arg Leu Leu Pro Val Leu Cys Gln Asp His Gly Leu Thr Pro Asp Gln
        515                 520                 525

Val Val Ala Ile Ala Ser Asn Ile Gly Gly Lys Gln Ala Leu Glu Thr
    530                 535                 540

Val Gln Arg Leu Leu Pro Val Leu Cys Gln Asp His Gly Leu Thr Pro
545                 550                 555                 560

Asp Gln Val Val Ala Ile Ala Ser Asn Gly Gly Gly Lys Gln Ala Leu
                565                 570                 575

Glu Thr Val Gln Arg Leu Leu Pro Val Leu Cys Gln Asp His Gly Leu
            580                 585                 590

Thr Pro Asp Gln Val Val Ala Ile Ala Ser Asn Asn Gly Gly Lys Gln
        595                 600                 605

Ala Leu Glu Ser Ile Val Ala Gln Leu Ser Arg Pro Asp Pro Ala Leu
    610                 615                 620

Ala Ala Leu Thr Asn Asp His Leu Val Ala Leu Ala Cys Leu Gly Gly
625                 630                 635                 640

Arg Pro Ala Met Asp Ala Val Lys Lys Gly Leu Pro His Ala Pro Glu
                645                 650                 655

Leu Ile Arg Arg Val Asn Arg Arg Ile Gly Glu Arg Thr Ser His Arg
            660                 665                 670

Val Ala Ile Ser Arg Val Gly Gly Ser Ser Arg Arg Glu Ser Ile Asn
        675                 680                 685

Pro Trp Ile Leu Thr Gly Phe Ala Asp Ala Glu Gly Cys Phe Met Leu
    690                 695                 700

Asn Ile Trp Asn Lys Asn Arg Thr Arg Ala Lys Tyr Tyr Thr Ala Leu
705                 710                 715                 720

Arg Phe Glu Ile Ala Leu His Asn Lys Asp Lys Ser Ile Leu Glu Asn
                725                 730                 735

Ile Arg Ser Thr Trp Lys Val Gly Lys Ile Arg Asn Ile Gly Asp Arg
            740                 745                 750

Val Val Lys Leu Val Val Gly Arg Phe Glu Asp Leu Lys Val Ile Ile
        755                 760                 765
```

```
Asp His Phe Glu Lys Tyr Pro Leu Ile Thr Gln Lys Leu Gly Asp Tyr
770                 775                 780

Lys Leu Phe Lys Gln Ala Phe Ser Leu Met Glu Asn Lys Glu His Leu
785                 790                 795                 800

Lys Glu Asn Gly Ile Lys Glu Leu Val Arg Ile Lys Ala Lys Met Asn
                805                 810                 815

Trp Gly Leu Asn Asp Glu Leu Lys Lys Ala Phe Pro Glu Asn Ile Ser
                820                 825                 830

Lys Glu Arg Pro Leu Ile Asn Lys Asn Ile Pro Asn Leu Lys Trp Leu
                835                 840                 845

Ala Gly Phe Thr Ser Gly Asp Gly Tyr Phe Gly Val Glu Leu Met Lys
850                 855                 860

Arg Thr Thr Gly Thr His Val Thr Val Arg Leu Arg Phe Ser Ile Thr
865                 870                 875                 880

Gln His Ile Arg Asp Lys Asn Leu Met Asn Ser Leu Ile Thr Tyr Leu
                885                 890                 895

Gly Cys Gly Arg Ile Ser Glu Arg Asn Lys Ser Glu Tyr Ser Trp Leu
                900                 905                 910

Glu Phe Val Val Thr Lys Phe Ser Asp Ile Asn Asp Lys Ile Ile Pro
                915                 920                 925

Val Phe Gln Glu Asn Thr Leu Ile Gly Val Lys Leu Glu Asp Phe Glu
930                 935                 940

Asp Trp Cys Lys Val Ala Lys Leu Ile Glu Glu Lys Lys His Leu Thr
945                 950                 955                 960

Glu Ser Gly Leu Asp Glu Ile Lys Lys Ile Lys Leu Asn Met Asn Lys
                965                 970                 975

Gly Arg

<210> SEQ ID NO 10
<211> LENGTH: 1219
<212> TYPE: PRT
<213> ORGANISM: Artificial Sequence
<220> FEATURE:
<223> OTHER INFORMATION: Made in Lab - synthesized megaTAL PCSK9.H7.C11/
      Trex2 fusion construct

<400> SEQUENCE: 10

Met Gly Ser Cys Arg Pro Pro Lys Lys Lys Arg Lys Val Val Asp Leu
1               5                   10                  15

Arg Thr Leu Gly Tyr Ser Gln Gln Gln Glu Lys Ile Lys Pro Lys
                20                  25                  30

Val Arg Ser Thr Val Ala Gln His His Glu Ala Leu Val Gly His Gly
                35                  40                  45

Phe Thr His Ala His Ile Val Ala Leu Ser Gln His Pro Ala Ala Leu
                50                  55                  60

Gly Thr Val Ala Val Thr Tyr Gln His Ile Ile Thr Ala Leu Pro Glu
65                  70                  75                  80

Ala Thr His Glu Asp Ile Val Gly Val Gly Lys Gln Trp Ser Gly Ala
                85                  90                  95

Arg Ala Leu Glu Ala Leu Leu Thr Asp Ala Gly Glu Leu Arg Gly Pro
                100                 105                 110

Pro Leu Gln Leu Asp Thr Gly Gln Leu Val Lys Ile Ala Lys Arg Gly
                115                 120                 125

Gly Val Thr Ala Met Glu Ala Val His Ala Ser Arg Asn Ala Leu Thr
130                 135                 140
```

```
Gly Ala Pro Leu Asn Leu Thr Pro Asp Gln Val Ala Ile Ala Ser
145                 150                 155                 160

Asn Asn Gly Gly Lys Gln Ala Leu Glu Thr Val Gln Arg Leu Leu Pro
                165                 170                 175

Val Leu Cys Gln Asp His Gly Leu Thr Pro Asp Gln Val Val Ala Ile
            180                 185                 190

Ala Ser Asn Asn Gly Gly Lys Gln Ala Leu Glu Thr Val Gln Arg Leu
        195                 200                 205

Leu Pro Val Leu Cys Gln Asp His Gly Leu Thr Pro Asp Gln Val Val
    210                 215                 220

Ala Ile Ala Ser Asn Asn Gly Gly Lys Gln Ala Leu Glu Thr Val Gln
225                 230                 235                 240

Arg Leu Leu Pro Val Leu Cys Gln Asp His Gly Leu Thr Pro Asp Gln
                245                 250                 255

Val Val Ala Ile Ala Ser His Asp Gly Gly Lys Gln Ala Leu Glu Thr
            260                 265                 270

Val Gln Arg Leu Leu Pro Val Leu Cys Gln Asp His Gly Leu Thr Pro
        275                 280                 285

Asp Gln Val Val Ala Ile Ala Ser Asn Ile Gly Gly Lys Gln Ala Leu
    290                 295                 300

Glu Thr Val Gln Arg Leu Leu Pro Val Leu Cys Gln Asp His Gly Leu
305                 310                 315                 320

Thr Pro Asp Gln Val Val Ala Ile Ala Ser His Asp Gly Gly Lys Gln
                325                 330                 335

Ala Leu Glu Thr Val Gln Arg Leu Leu Pro Val Leu Cys Gln Asp His
            340                 345                 350

Gly Leu Thr Pro Asp Gln Val Val Ala Ile Ala Ser His Asp Gly Gly
        355                 360                 365

Lys Gln Ala Leu Glu Thr Val Gln Arg Leu Leu Pro Val Leu Cys Gln
    370                 375                 380

Asp His Gly Leu Thr Pro Asp Gln Val Val Ala Ile Ala Ser His Asp
385                 390                 395                 400

Gly Gly Lys Gln Ala Leu Glu Thr Val Gln Arg Leu Leu Pro Val Leu
                405                 410                 415

Cys Gln Asp His Gly Leu Thr Pro Asp Gln Val Val Ala Ile Ala Ser
            420                 425                 430

Asn Gly Gly Lys Gln Ala Leu Glu Thr Val Gln Arg Leu Leu Pro
        435                 440                 445

Val Leu Cys Gln Asp His Gly Leu Thr Pro Asp Gln Val Val Ala Ile
    450                 455                 460

Ala Ser Asn Asn Gly Gly Lys Gln Ala Leu Glu Thr Val Gln Arg Leu
465                 470                 475                 480

Leu Pro Val Leu Cys Gln Asp His Gly Leu Thr Pro Asp Gln Val Val
                485                 490                 495

Ala Ile Ala Ser Asn Asn Gly Gly Lys Gln Ala Leu Glu Thr Val Gln
            500                 505                 510

Arg Leu Leu Pro Val Leu Cys Gln Asp His Gly Leu Thr Pro Asp Gln
        515                 520                 525

Val Val Ala Ile Ala Ser Asn Ile Gly Gly Lys Gln Ala Leu Glu Thr
    530                 535                 540

Val Gln Arg Leu Leu Pro Val Leu Cys Gln Asp His Gly Leu Thr Pro
545                 550                 555                 560

Asp Gln Val Val Ala Ile Ala Ser Asn Gly Gly Gly Lys Gln Ala Leu
```

```
            565                 570                 575
Glu Thr Val Gln Arg Leu Leu Pro Val Leu Cys Gln Asp His Gly Leu
            580                 585                 590

Thr Pro Asp Gln Val Val Ala Ile Ala Ser Asn Asn Gly Gly Lys Gln
            595                 600                 605

Ala Leu Glu Ser Ile Val Ala Gln Leu Ser Arg Pro Asp Pro Ala Leu
610                 615                 620

Ala Ala Leu Thr Asn Asp His Leu Val Ala Leu Ala Cys Leu Gly Gly
625                 630                 635                 640

Arg Pro Ala Met Asp Ala Val Lys Lys Gly Leu Pro His Ala Pro Glu
            645                 650                 655

Leu Ile Arg Arg Val Asn Arg Arg Ile Gly Glu Arg Thr Ser His Arg
            660                 665                 670

Val Ala Ile Ser Arg Val Gly Gly Ser Arg Arg Glu Ser Ile Asn
            675                 680                 685

Pro Trp Ile Leu Thr Gly Phe Ala Asp Ala Glu Gly Cys Phe Met Leu
            690                 695                 700

Asn Ile Trp Asn Lys Asn Arg Thr Arg Ala Lys Tyr Tyr Thr Ala Leu
705                 710                 715                 720

Arg Phe Glu Ile Ala Leu His Asn Lys Asp Lys Ser Ile Leu Glu Asn
                    725                 730                 735

Ile Arg Ser Thr Trp Lys Val Gly Lys Ile Arg Asn Ile Gly Asp Arg
                    740                 745                 750

Val Val Lys Leu Val Val Gly Arg Phe Glu Asp Leu Lys Val Ile Ile
                    755                 760                 765

Asp His Phe Glu Lys Tyr Pro Leu Ile Thr Gln Lys Leu Gly Asp Tyr
    770                 775                 780

Lys Leu Phe Lys Gln Ala Phe Ser Leu Met Glu Asn Lys Glu His Leu
785                 790                 795                 800

Lys Glu Asn Gly Ile Lys Glu Leu Val Arg Ile Lys Ala Lys Met Asn
                    805                 810                 815

Trp Gly Leu Asn Asp Glu Leu Lys Lys Ala Phe Pro Glu Asn Ile Ser
                    820                 825                 830

Lys Glu Arg Pro Leu Ile Asn Lys Asn Ile Pro Asn Leu Lys Trp Leu
            835                 840                 845

Ala Gly Phe Thr Ser Gly Asp Gly Tyr Phe Gly Val Glu Leu Met Lys
            850                 855                 860

Arg Thr Thr Gly Thr His Val Thr Val Arg Leu Arg Phe Ser Ile Thr
865                 870                 875                 880

Gln His Ile Arg Asp Lys Asn Leu Met Asn Ser Leu Ile Thr Tyr Leu
                    885                 890                 895

Gly Cys Gly Arg Ile Ser Glu Arg Asn Lys Ser Glu Tyr Ser Trp Leu
                    900                 905                 910

Glu Phe Val Val Thr Lys Phe Ser Asp Ile Asn Asp Lys Ile Ile Pro
                    915                 920                 925

Val Phe Gln Glu Asn Thr Leu Ile Gly Val Lys Leu Glu Asp Phe Glu
            930                 935                 940

Asp Trp Cys Lys Val Ala Lys Leu Ile Glu Lys Lys His Leu Thr
945                 950                 955                 960

Glu Ser Gly Leu Asp Glu Ile Lys Lys Ile Lys Leu Asn Met Asn Lys
                    965                 970                 975

Gly Arg Val Phe Ala Ser Thr Gly Ser Glu Pro Pro Arg Ala Glu Thr
                    980                 985                 990
```

Phe Val Phe Leu Asp Leu Glu Ala Thr Gly Leu Pro Asn Met Asp Pro
    995                 1000                1005

Glu Ile Ala Glu Ile Ser Leu Phe Ala Val His Arg Ser Ser Leu
    1010                1015                1020

Glu Asn Pro Glu Arg Asp Asp Ser Gly Ser Leu Val Leu Pro Arg
    1025                1030                1035

Val Leu Asp Lys Leu Thr Leu Cys Met Cys Pro Glu Arg Pro Phe
    1040                1045                1050

Thr Ala Lys Ala Ser Glu Ile Thr Gly Leu Ser Ser Glu Ser Leu
    1055                1060                1065

Met His Cys Gly Lys Ala Gly Phe Asn Gly Ala Val Val Arg Thr
    1070                1075                1080

Leu Gln Gly Phe Leu Ser Arg Gln Glu Gly Pro Ile Cys Leu Val
    1085                1090                1095

Ala His Asn Gly Phe Asp Tyr Asp Phe Pro Leu Leu Cys Thr Gly
    1100                1105                1110

Leu Gln Arg Leu Gly Ala His Leu Pro Gln Asp Thr Val Cys Leu
    1115                1120                1125

Asp Thr Leu Pro Ala Leu Arg Gly Leu Asp Arg Ala His Ser His
    1130                1135                1140

Gly Thr Arg Ala Gln Gly Arg Lys Ser Tyr Ser Leu Ala Ser Leu
    1145                1150                1155

Phe His Arg Tyr Phe Gln Ala Glu Pro Ser Ala Ala His Ser Ala
    1160                1165                1170

Glu Gly Asp Val His Thr Leu Leu Leu Ile Phe Leu His Arg Ala
    1175                1180                1185

Pro Glu Leu Leu Ala Trp Ala Asp Glu Gln Ala Arg Ser Trp Ala
    1190                1195                1200

His Ile Glu Pro Met Tyr Val Pro Pro Asp Gly Pro Ser Leu Glu
    1205                1210                1215

Ala

<210> SEQ ID NO 11
<211> LENGTH: 22
<212> TYPE: DNA
<213> ORGANISM: Homo sapiens

<400> SEQUENCE: 11
atctaagaga tacacctcca cc                                             22

<210> SEQ ID NO 12
<211> LENGTH: 14
<212> TYPE: DNA
<213> ORGANISM: Homo sapiens

<400> SEQUENCE: 12
gggcaccctg gatg                                                      14

<210> SEQ ID NO 13
<211> LENGTH: 41
<212> TYPE: DNA
<213> ORGANISM: Homo sapiens

<400> SEQUENCE: 13
gggcaccctg gatgctggta tctaagagat acacctccac c                        41

```
<210> SEQ ID NO 14
<211> LENGTH: 22
<212> TYPE: DNA
<213> ORGANISM: Homo sapiens

<400> SEQUENCE: 14
atctaagaga taccacaggc tc                                              22

<210> SEQ ID NO 15
<211> LENGTH: 22
<212> TYPE: DNA
<213> ORGANISM: Homo sapiens

<400> SEQUENCE: 15
atctaagaga tactacgtct gc                                              22

<210> SEQ ID NO 16
<211> LENGTH: 22
<212> TYPE: DNA
<213> ORGANISM: Homo sapiens

<400> SEQUENCE: 16
cttccaggaa tacacctcca cc                                              22

<210> SEQ ID NO 17
<211> LENGTH: 22
<212> TYPE: DNA
<213> ORGANISM: Homo sapiens

<400> SEQUENCE: 17
tgtctgcgta tacacctcca cc                                              22

<210> SEQ ID NO 18
<211> LENGTH: 22
<212> TYPE: DNA
<213> ORGANISM: Homo sapiens

<400> SEQUENCE: 18
tttccactta tacacctcca cc                                              22

<210> SEQ ID NO 19
<211> LENGTH: 22
<212> TYPE: DNA
<213> ORGANISM: Homo sapiens

<400> SEQUENCE: 19
gccggaaaaa tacacctcca cc                                              22

<210> SEQ ID NO 20
<211> LENGTH: 7244
<212> TYPE: DNA
<213> ORGANISM: Artificial Sequence
<220> FEATURE:
<223> OTHER INFORMATION: Made in Lab - synthesized I-OnuI variant PCSK9.
      H7.C11 surface display plasmid

<400> SEQUENCE: 20
gacgaaaggg cctcgtgata cgcctatttt tataggttaa tgtcatgata ataatggttt      60
cttaggacgg atcgcttgcc tgtaacttac acgcgcctcg tatcttttaa tgatggaata    120
atttgggaat ttactctgtg tttatttatt ttatgttttt gtatttggat tttagaaagt    180
aaataaagaa ggtagaagag ttcggaatg aagaaaaaaa aataaacaaa ggtttaaaaa    240
atttcaacaa aaagcgtact ttacatatat atttattaga caagaaaagc agattaaata    300
```

```
gatatacatt cgattaacga taagtaaaat gtaaaatcac aggattttcg tgtgtggtct      360
tctacacaga caagatgaaa caattcggca ttaatacctg agagcaggaa gagcaagata      420
aaaggtagta tttgttggcg atcccctag agtcttttac atcttcggaa aacaaaaact       480
attttttctt taatttcttt ttttacttc tatttttaat ttatatattt atattaaaaa       540
atttaaatta taattatttt tatagcacgt gatgaaaagg acccaggtgg cacttttcgg      600
ggaaatgtgc gcggaacccc tatttgttta tttttctaaa tacattcaaa tatgtatccg      660
ctcatgagac aataaccctg ataaatgctt caataatatt gaaaaggaa gagtatgagt       720 attcaacatt tccgtgtcgc ccttattccc ttttttgcgg cattttgcct tcctgttttt      780
gctcacccag aaacgctggt gaaagtaaaa gatgctgaag atcagttggg tgcacgagtg      840
ggttacatcg aactggatct caacagcggt aagatcctg agagttttcg ccccgaagaa       900
cgttttccaa tgatgagcac ttttaaagtt ctgctatgtg gcgcggtatt atcccgtatt      960
gacgccgggc aagagcaact cggtcgccgc atacactatt ctcagaatga cttggttgag     1020
tactcaccag tcacagaaaa gcatcttacg gatggcatga cagtaagaga attatgcagt     1080
gctgccataa ccatgagtga taacactgcg gccaacttac ttctgacaac gatcggagga     1140
ccgaaggagc taaccgcttt ttttcacaac atggggatc atgtaactcg ccttgatcgt      1200
tgggaaccgg agctgaatga agccatacca aacgacgagc gtgacaccac gatgcctgta     1260
gcaatggcaa caacgttgcg caaactatta actggcgaac tacttactct agcttcccgg     1320
caacaattaa tagactggat ggaggcggat aaagttgcag gaccacttct gcgctcggcc     1380
cttccggctg gctggtttat tgctgataaa tctggagccg gtgagcgtgg gtctcgcggt     1440
atcattgcag cactggggcc agatggtaag ccctcccgta tcgtagttat ctacacgacg     1500
ggcagtcagg caactatgga tgaacgaaat agacagatcg ctgagatagg tgcctcactg     1560
attaagcatt ggtaactgtc agaccaagtt tactcatata tactttagat tgatttaaaa     1620
cttcattttt aatttaaaag gatctaggtg aagatccttt ttgataatct catgaccaaa     1680
atcccttaac gtgagttttc gttccactga gcgtcagacc ccgtagaaaa gatcaaagga     1740
tcttcttgag atcctttttt tctgcgcgta atctgctgct tgcaaacaaa aaaaccaccg     1800
ctaccagcgg tggtttgttt gccggatcaa gagctaccaa ctcttttcc gaaggtaact      1860 ggcttcagca gagcgcagat accaaatact gtccttctag tgtagccgta gttaggccac     1920
cacttcaaga actctgtagc accgcctaca tacctcgctc tgctaatcct gttaccagtg     1980
gctgctgcca gtggcgataa gtcgtgtctt accgggttgg actcaagacg atagttaccg     2040
gataaggcgc agcggtcggg ctgaacgggg ggttcgtgca cacagcccag cttggagcga     2100
acgacctaca ccgaactgag atacctacag cgtgagcatt gagaaagcgc cacgcttccc     2160
gaagggagaa aggcggacag gtatccggta agcggcaggg tcggaacagg agagcgcacg     2220
agggagcttc caggggggaa cgcctggtat ctttatagtc ctgtcgggtt tcgccacctc     2280
tgacttgagc gtcgattttt gtgatgctcg tcagggggc cgagcctatg gaaaaacgcc      2340
agcaacgcgg cctttttacg gttcctggcc ttttgctggc cttttgctca catgttcttt     2400
cctgcgttat cccctgattc tgtggataac cgtattaccg cctttgagtg agctgatacc     2460
gctcgccgca gccgaacgac cgagcgcagc gagtcagtga gcgaggaagc ggaagagcgc     2520
ccaatacgca aaccgcctct ccccgcgcgt tggccgattc attaatgcag ctggcacgac     2580
aggtttcccg actggaaagc gggcagtgag cgcaacgcaa ttaatgtgag ttacctcact     2640
```

```
cattaggcac cccaggcttt acactttatg cttccggctc ctatgttgtg tggaattgtg    2700
agcggataac aatttcacac aggaaacagc tatgaccatg attacgccaa gctcggaatt    2760
aaccctcact aaagggaaca aaagctgggt acccgacagg ttatcagcaa caacacagtc    2820
atatccattc tcaattagct ctaccacagt gtgtgaacca atgtatccag caccacctgt    2880
aaccaaaaca attttagaag tactttcact ttgtaactga gctgtcattt atattgaatt    2940
ttcaaaaatt cttacttttt ttttggatgg acgcaaagaa gtttaataat catattacat    3000
ggcattacca ccatatacat atccatatac atatccatat ctaatcttac ttatatgttg    3060
tggaaatgta aagagcccca ttatcttagc ctaaaaaaac cttctctttg aactttcag     3120 taatacgctt aactgctcat tgctatattg aagtacggat tagaagccgc cgagcgggtg    3180
acagccctcc gaaggaagac tctcctccgt gcgtcctcgt cttcaccggt cgcgttcctg    3240
aaacgcagat gtgcctcgcg ccgcactgct ccgaacaata aagattctac aatactagct    3300
tttatggtta tgaagaggaa aaattggcag taacctggcc ccacaaacct tcaaatgaac    3360
gaatcaaatt aacaaccata ggatgataat gcgattagtt ttttagcctt atttctgggg    3420
taattaatca gcgaagcgat gattttttgat ctattaacag atatataaat gcaaaaactg    3480
cataaccact ttaactaata cttttcaacat tttcggtttg tattacttct tattcaaatg    3540
taataaaaga tcgaatccta cttcatacat tttcaattaa gatgcagtta cttcgctgtt    3600
tttcaatatt ttctgttatt gcttcagttt tagcacagga actgacaact atatgcgagc    3660
aaatcccctc accaacttta gaatcgacgc cgtactcttt gtcaacgact actattttgg    3720
ccaacgggaa ggcaatgcaa ggagtttttg aatattacaa atcagtaacg tttgtcagta    3780
attgcggttc tcacccctca acaactagca aaggcagccc cataaacaca cagtatgttt    3840
ttaaggacaa tagctcgacg attgaaggta gatacccata cgacgttcca gactacgctc    3900
tgcaggctag tggtggagga ggctctggtg gaggcggtag cggaggcgga gggtcggcta    3960
gctccatcaa cccatggatt ctgactggtt tcgctgatgc cgaaggatgc ttcatgctaa    4020
acatctggaa caaaaacaga acacgtgcca aatactacac tgcactgcgc ttcgaaatcg    4080
cactgcacaa caaggacaaa tcgattctgg agaatatccg gtcgacttgg aaggtcggca    4140
aaatcagaaa cataggcgac cgagtagtca aactggtagt cggacgtttc gaagatttga    4200
aagtgattat cgaccacttc gagaaatatc cgctgattac ccagaaattg ggcgattaca    4260
agctgtttaa acaggcattc agcctcatgg agaacaaaga acatcttaag gagaatggga    4320
ttaaggagct cgtacgaatc aaagctaaga tgaattgggg tctcaatgac gaattgaaaa    4380
aagcatttcc agagaacatt agcaaagagc gcccccttat caataagaac atcccaaatc    4440
tcaaatggct ggctggattc acatctggtg acggctactt cggggtggaa ctaatgaaga    4500
ggacaaccgg aacacacgta acagtgcgac tgcgattcag catcacacag cacatcagag    4560
acaagaacct gatgaattca ttgataacat acctaggctg tggtcgcatc tcggagagaa    4620
acaaatctga gtatagttgg ctcgaattcg tagtaactaa attcagcgat atcaacgaca    4680
agatcattcc ggtattccag gaaaatactc tgattggcgt caaactcgag gactttgaag    4740
attggtgcaa ggttgccaaa ttgatcgaag agaagaaaca cctgaccgaa tccggttgg     4800 atgagattaa gaaaatcaag ctgaacatga acaaaggtcg tgtcttctct agaggcggtt    4860
ccagaagcgg atctggtact ggcgaacaga aactcataag cgaagaagac cttagcggga    4920
ctggagagca aaagttgatt tctgaggagg atttgtcggg aaccggggag cagaagttaa    4980
tcagtgaaga ggatctcagt ggaacgggcg aacaaaagtt gatctcggag gaagacttat    5040
```

```
aatgaagatc tgataacaac agtgtagatg taacaaaatc gactttgttc ccactgtact   5100
tttagctcgt acaaaataca atatactttt catttctccg taaacaacat gttttcccat   5160
gtaatatcct tttctatttt tcgttccgtt accaacttta cacatacttt atatagctat   5220
tcacttctat acactaaaaa actaagacaa ttttaatttt gctgcctgcc atatttcaat   5280
ttgttataaa ttcctataat ttatcctatt agtagctaaa aaaagatgaa tgtgaatcga   5340
atcctaagag aattgagctc caattcgccc tatagtgagt cgtattacaa ttcactggcc   5400
gtcgttttac aacgtcgtga ctgggaaaac cctggcgtta cccaacttaa tcgccttgca   5460
gcacatcccc ctttcgccag ctggcgtaat agcgaagagg cccgcaccga tcgccttttcc  5520 caacagttgc gcagcctgaa tggcgaatgg acgcgccctg tagcggcgca ttaagcgcgg   5580
cgggtgtggt ggttacgcgc agcgtgaccg ctacacttgc cagcgcccta gcgcccgctc   5640
ctttcgcttt cttcccttcc tttctcgcca cgttcgccgg ctttccccgt caagctctaa   5700
atcgggggct ccctttaggg ttccgattta gtgctttacg gcacctcgac cccaaaaaac   5760
ttgattaggg tgatggttca cgtagtgggc catcgccctg atagacggtt tttcgccctt   5820
tgacgttgga gtccacgttc tttaatagtg gactcttgtt ccaaactgga acaacactca   5880
accctatctc ggtctattct tttgatttat aagggatttt gccgatttcg gcctattggt   5940
taaaaaatga gctgatttaa caaaaattta acgcgaattt taacaaaata ttaacgttta   6000
caatttcctg atgcggtatt ttctccttac gcatctgtgc ggtatttcac accgcaggca   6060
agtgcacaaa caatacttaa ataaatacta ctcagtaata acctatttct tagcatttttt  6120 gacgaaattt gctattttgt tagagtcttt tacaccattt gtctccacac ctccgcttac   6180
atcaacacca ataacgccat ttaatctaag cgcatcacca acattttctg gcgtcagtcc   6240
accagctaac ataaaatgta agctttcggg gctctcttgc cttccaaccc agtcagaaat   6300
cgagttccaa tccaaaagtt cacctgtccc acctgcttct gaatcaaaca agggaataaa   6360
cgaatgaggt ttctgtgaag ctgcactgag tagtatgttg cagtcttttg gaaatacgag   6420
tcttttaata actggcaaac cgaggaactc ttggtattct tgccacgact catctccatg   6480
cagttggacg acatcaatgc cgtaatcatt gaccagagcc aaaacatcct ccttaggttg   6540
attacgaaac acgccaacca agtatttcgg agtgcctgaa ctattttat atgcttttac    6600 aagacttgaa attttccttg caataaccgg gtcaattgtt ctctttctat tgggcacaca   6660 tataatacc  agcaagtcag catcggaatc aagagcacat tctgcggcct ctgtgctctg   6720
caagccgcaa acttttcacca atggaccaga actacctgtg aaattaataa cagacatact  6780
ccaagctgcc tttgtgtgct taatcacgta tactcacgtg ctcaatagtc accaatgccc   6840
tccctcttgg ccctctcctt ttcttttttc gaccgaatta attcttaatc ggcaaaaaaa   6900
gaaaagctcc ggatcaagat tgtacgtaag gtgacaagct atttttcaat aaagaatatc   6960
ttccactact gccatctggc gtcataactg caaagtacac atatattacg atgctgtcta   7020
ttaaatgctt cctatattat atatatagta atgtcgttta tggtgcactc tcagtacaat   7080
ctgctctgat gccgcatagt taagccagcc ccgacacccg ccaacacccg ctgacgcgcc   7140
ctgacgggct tgtctgctcc cggcatccgc ttacagacaa gctgtgaccg tctccgggag   7200
ctgcatgtgt cagaggtttt caccgtcatc accgaaacgc gcga                    7244
```

<210> SEQ ID NO 21
<211> LENGTH: 2952
<212> TYPE: RNA

<213> ORGANISM: Artificial Sequence
<220> FEATURE:
<223> OTHER INFORMATION: Made in Lab - synthesized megaTAL PCSK9.H7.C11
      mRNA

<400> SEQUENCE: 21

```
augggauccu gcaggccacc uaagaagaaa cgcaaagucg uggaucuacg cacgcucggc    60
uacagucagc agcagcaaga gaagaucaaa ccgaaggugc guucgacagu ggcgcagcac   120
cacgaggcac ugguggggcca uggguuuaca cacgcgcaca ucguugcgcu cagccaacac   180
ccggcagcgu uagggaccgu cgcugucacg uaucagcaca uaaucacggc guugccagag   240
gcgacacacg aagacaucgu uggcgucggc aaacaguggu ccggcgcacg cgcccuggag   300
gccuugcuca cggaugcggg ggaguugaga ggucggccgu acaguugga cacaggccaa    360
cuugugaaga uugcaaaacg uggcggcgug accgcaaugg aggcagugca ugcaucgcgc   420
aaugcacuga cgggugcccc ccugaacuua cacccgauc aagugguagc gauagcguca    480
aacaacgggg uaaacaggc uuuggagacg uacagcggu uauugccggu acucugccag     540
gaccacggau ugacaccgga ccaaguggug gcgauugcgu ccaauaacgg aggcaagcag    600
gcacuagaga ccguccaacg gcuucuuccc guucuuuguc aggaucaugg cuaaccccu    660
gaucagguag ucgcuauagc uucaaauaac gggggcaagc aagcacugga gaccguucaa    720
cgacuccugc cagugcucug ccaagaccac ggacuuacgc cagaucaggu gguugcuauu    780
gccucccaug auggcgggaa acaagcguug gaaacugugc agagacuguu accgucuug     840
ugucaagacc acggccucac gccagaucag guggucuagcca uagcgucgaa cauuggugg    900
aagcaagccc uugaaacggu ccagcgucuu cugccggugu ugugccagga ccacggacua    960
acgccggauc aggucguagc cauugcuuca cacgacggcg gcaaacaggc gcuagagaca   1020
guccagcgcc ucuugccugu guuaaugccag gaucacggcu uaaccccaga ccaaguugug   1080
gcuauugcau cucaugacgg uggcaaaacaa gccuuggaga cagugcaacg auuacugccu   1140
gucuuauguc aggaucaugg ccugacgccc gaucagguag uggcaaucgc aucucacgau   1200
ggagguaagc aagcacugga gacuguccag agauuguuac ccguacuaug ucaagaucau   1260
gguuugacgc cugaucaggu guugcgauua ccagcaaug gcggagggaa acaggcucuu   1320
gaaaccguac agcgacuucu cccagucuug ugccaagauc acgggcuuac uccugaucaa   1380
gucuagcua ucgccagcaa uaaugggugg aagcaggccc uggaaacugu acaacgucug   1440
cucccaguac uuugucaaga ccacgggcuc accccggacc aggucguugc caucgcccua   1500
aacaacggcg aaagcaagc ucucgaaaca guacaacggc uauugccagu ccauugucaa    1560
gaccacggac ucaccccga ucagguuguc gcaaucgcaa guauaucgg cgguaagcaa     1620
gcccuagaga cugugcaacg ccuacucccc gugcuguguc aggaucacgg cuugacuccg    1680
gaucaagugg ucgcgaucgc gucuaacggc gggggaagc aggcgcugga gacuguucag     1740
agacugcugc cugugcuuug ccaggaccau ggucugacac cgaccaagu guggcgauua   1800
gccaguaaua acgggggaaa acaggcacua gagagcauug uggcccagcu gagccggccu   1860
gauccggcgu uggccgcguu gaccaacgac caccucgucg ccuuggccug ccucggcgga   1920
cguccugcca uggaucagu gaaaaaggga uugccgcacg cgccggaauu gaucagaaga    1980
gucaaucgcc guauuggcga acgcacguc caucgcguug cgauaucuag aguggggagga    2040
agcucgcgca gagaguccau caacccuauug auucugacug guucgcguga ugccgaagga    2100
ugcuucaugc uaaaacaucug gaacaaaaac agaacacgug ccaaauacua cacugcacug    2160
```

-continued

| | |
|---|---|
| cgcuucgaaa ucgcacugca caacaaggac aaaucgauuc uggagaauau ccggucgacu | 2220 |
| uggaaggucg gcaaaaucag aaacauaggc gaccgaguag ucaaacuggu agucggacgu | 2280 |
| uucgaagauu ugaaagugau uaucgaccac uucgagaaau auccgcugau ucccagaaa | 2340 |
| uugggcgauu acaagcuguu uaaacaggca uucagccuca uggagaacaa agaacaucuu | 2400 |
| aaggagaaug ggauuaagga gcucguacga aucaaagcua agaugaauug gggucucaau | 2460 |
| gacgaauuga aaaagcauuc cagagaaac auuagcaaag agcgccccu uaucaauaag | 2520 |
| aacaucccaa aucucaaaug gcuggcugga uucacaucug gugacggcua cuucggggug | 2580 |
| gaacuaauga gaggacaac cggaacacac guaacagugc gacugcgauu cagcaucaca | 2640 |
| cagcacauca gagacaagaa ccugaugaau ucauugauaa cauaccuagg cuguggucgc | 2700 |
| aucucggaga gaaacaaauc ugaguauagu uggcucgaau ucuaguaac uaaauucagc | 2760 |
| gauaucaacg acaagaucau uccgguauuc caggaaaaua cucugauugg cgucaaacuc | 2820 |
| gaggacuuug aagauggug caagguugcc aaauugaucg aagagaagaa acaccugacc | 2880 |
| gaauccgguu uggaugagau uaagaaaauc aagcugaaca ugaacaaagg ucgugucuuc | 2940 |
| agcggccgcu ga | 2952 |

<210> SEQ ID NO 22
<211> LENGTH: 711
<212> TYPE: RNA
<213> ORGANISM: Mus musculus

<400> SEQUENCE: 22

| | |
|---|---|
| augucugagc caccucgggc ugagaccuuu guauuccugg accuagaagc cacugggcuc | 60 |
| ccaaacaugg acccugagau ugcagagaua ucccuuuuug cuguucaccg cucuucccug | 120 |
| gagaacccag aacggauga uucugguucc uggugcugc cccguguucu ggacaagcuc | 180 |
| acacugugca ugugcccgga gcgccccuuu acugccaagg ccagugagau uacugguuug | 240 |
| agcagcgaaa gccugaugca cugcgggaag gcugguuuca auggcgcugu gguaaggaca | 300 |
| cugcagggcu uccuaagccg ccaggagggc cccaucugcc uuguggccca caauggcuuc | 360 |
| gauuaugacu ucccacugcu gugcacggag cuacaacguc uggugcccca ucugccccaa | 420 |
| gacacugucu gccuggacac acugccugca uugcggggcc uggaccgugc ucacagccac | 480 |
| ggcaccaggg cucaaggccg caaaagcuac agccuggcca gucucuucca ccgcuacuuc | 540 |
| caggcugaac ccagugcugc ccauucagca gaaggugaug ugcacacccu gcuucugauc | 600 |
| uuccugcauc gugcuccuga gcugcucgcc ugggcagaug agcaggcccg cagcugggcu | 660 |
| cauauugagc ccauguacgu gccaccugau ggccaagcc ucgaagccug a | 711 |

<210> SEQ ID NO 23
<211> LENGTH: 236
<212> TYPE: PRT
<213> ORGANISM: Mus musculus

<400> SEQUENCE: 23

Met Ser Glu Pro Pro Arg Ala Glu Thr Phe Val Phe Leu Asp Leu Glu
1               5                   10                  15

Ala Thr Gly Leu Pro Asn Met Asp Pro Glu Ile Ala Glu Ile Ser Leu
            20                  25                  30

Phe Ala Val His Arg Ser Ser Leu Glu Asn Pro Glu Arg Asp Asp Ser
        35                  40                  45

Gly Ser Leu Val Leu Pro Arg Val Leu Asp Lys Leu Thr Leu Cys Met
    50                  55                  60

```
Cys Pro Glu Arg Pro Phe Thr Ala Lys Ala Ser Glu Ile Thr Gly Leu
 65                  70                  75                  80

Ser Ser Glu Ser Leu Met His Cys Gly Lys Ala Gly Phe Asn Gly Ala
                 85                  90                  95

Val Val Arg Thr Leu Gln Gly Phe Leu Ser Arg Gln Glu Gly Pro Ile
            100                 105                 110

Cys Leu Val Ala His Asn Gly Phe Asp Tyr Asp Phe Pro Leu Leu Cys
            115                 120                 125

Thr Glu Leu Gln Arg Leu Gly Ala His Leu Pro Gln Asp Thr Val Cys
130                 135                 140

Leu Asp Thr Leu Pro Ala Leu Arg Gly Leu Asp Arg Ala His Ser His
145                 150                 155                 160

Gly Thr Arg Ala Gln Gly Arg Lys Ser Tyr Ser Leu Ala Ser Leu Phe
                165                 170                 175

His Arg Tyr Phe Gln Ala Glu Pro Ser Ala Ala His Ser Ala Glu Gly
            180                 185                 190

Asp Val His Thr Leu Leu Leu Ile Phe Leu His Arg Ala Pro Glu Leu
            195                 200                 205

Leu Ala Trp Ala Asp Glu Gln Ala Arg Ser Trp Ala His Ile Glu Pro
210                 215                 220

Met Tyr Val Pro Pro Asp Gly Pro Ser Leu Glu Ala
225                 230                 235

<210> SEQ ID NO 24
<211> LENGTH: 3
<212> TYPE: PRT
<213> ORGANISM: Artificial Sequence
<220> FEATURE:
<223> OTHER INFORMATION: Exemplary linker sequence

<400> SEQUENCE: 24

Gly Gly Gly
1

<210> SEQ ID NO 25
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 25

Asp Gly Gly Gly Ser
1               5

<210> SEQ ID NO 26
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 26

Thr Gly Glu Lys Pro
1               5

<210> SEQ ID NO 27
<211> LENGTH: 4
<212> TYPE: PRT
<213> ORGANISM: Artificial Sequence
<220> FEATURE:
```

<223> OTHER INFORMATION: Exemplary linker sequence

<400> SEQUENCE: 27

Gly Gly Arg Arg
1

<210> SEQ ID NO 28
<211> LENGTH: 5
<212> TYPE: PRT
<213> ORGANISM: Artificial Sequence
<220> FEATURE:
<223> OTHER INFORMATION: Exemplary linker sequence

<400> SEQUENCE: 28

Gly Gly Gly Gly Ser
1               5

<210> SEQ ID NO 29
<211> LENGTH: 14
<212> TYPE: PRT
<213> ORGANISM: Artificial Sequence
<220> FEATURE:
<223> OTHER INFORMATION: Exemplary linker sequence

<400> SEQUENCE: 29

Glu Gly Lys Ser Ser Gly Ser Gly Ser Glu Ser Lys Val Asp
1               5                   10

<210> SEQ ID NO 30
<211> LENGTH: 18
<212> TYPE: PRT
<213> ORGANISM: Artificial Sequence
<220> FEATURE:
<223> OTHER INFORMATION: Exemplary linker sequence

<400> SEQUENCE: 30

Lys Glu Ser Gly Ser Val Ser Ser Glu Gln Leu Ala Gln Phe Arg Ser
1               5                   10                  15

Leu Asp

<210> SEQ ID NO 31
<211> LENGTH: 8
<212> TYPE: PRT
<213> ORGANISM: Artificial Sequence
<220> FEATURE:
<223> OTHER INFORMATION: Exemplary linker sequence

<400> SEQUENCE: 31

Gly Gly Arg Arg Gly Gly Gly Ser
1               5

<210> SEQ ID NO 32
<211> LENGTH: 9
<212> TYPE: PRT
<213> ORGANISM: Artificial Sequence
<220> FEATURE:
<223> OTHER INFORMATION: Exemplary linker sequence

<400> SEQUENCE: 32

Leu Arg Gln Arg Asp Gly Glu Arg Pro
1               5

<210> SEQ ID NO 33
<211> LENGTH: 12
<212> TYPE: PRT
<213> ORGANISM: Artificial Sequence

```
<220> FEATURE:
<223> OTHER INFORMATION: Exemplary linker sequence

<400> SEQUENCE: 33

Leu Arg Gln Lys Asp Gly Gly Gly Ser Glu Arg Pro
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Exemplary linker sequence

<400> SEQUENCE: 34

Leu Arg Gln Lys Asp Gly Gly Gly Ser Gly Gly Gly Ser Glu Arg Pro
1               5                   10                  15

<210> SEQ ID NO 35
<211> LENGTH: 7
<212> TYPE: PRT
<213> ORGANISM: Artificial Sequence
<220> FEATURE:
<223> OTHER INFORMATION: Cleavage sequence by TEV protease
<220> FEATURE:
<221> NAME/KEY: misc_feature
<222> LOCATION: (2)..(3)
<223> OTHER INFORMATION: Xaa is any amino acid
<220> FEATURE:
<221> NAME/KEY: misc_feature
<222> LOCATION: (5)..(5)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa = Gly or Ser

<400> SEQUENCE: 35

Glu Xaa Xaa Tyr Xaa Gln Xaa
1               5

<210> SEQ ID NO 36
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 36

Glu Asn Leu Tyr Phe Gln Gly
1               5

<210> SEQ ID NO 37
<211> LENGTH: 7
<212> TYPE: PRT
<213> ORGANISM: Artificial Sequence
<220> FEATURE:
<223> OTHER INFORMATION: Cleavage sequence by TEV protease

<400> SEQUENCE: 37

Glu Asn Leu Tyr Phe Gln Ser
1               5

<210> SEQ ID NO 38
<211> LENGTH: 22
<212> TYPE: PRT
<213> ORGANISM: Artificial Sequence
<220> FEATURE:
<223> OTHER INFORMATION: Self-cleaving polypeptide comprising 2A site
```

```
<400> SEQUENCE: 38

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 39
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 39

Ala Thr Asn Phe Ser Leu Leu Lys Gln Ala Gly Asp Val Glu Glu Asn
1               5                   10                  15

Pro Gly Pro

<210> SEQ ID NO 40
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 40

Leu Leu Lys Gln Ala Gly Asp Val Glu Glu Asn Pro Gly Pro
1               5                   10

<210> SEQ ID NO 41
<211> LENGTH: 21
<212> TYPE: PRT
<213> ORGANISM: Artificial Sequence
<220> FEATURE:
<223> OTHER INFORMATION: Self-cleaving polypeptide comprising 2A site

<400> SEQUENCE: 41

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 42
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 42

Glu Gly Arg Gly Ser Leu Leu Thr Cys Gly Asp Val Glu Glu Asn Pro
1               5                   10                  15

Gly Pro

<210> SEQ ID NO 43
<211> LENGTH: 13
<212> TYPE: PRT
<213> ORGANISM: Artificial Sequence
<220> FEATURE:
<223> OTHER INFORMATION: Self-cleaving polypeptide comprising 2A site

<400> SEQUENCE: 43

Leu Leu Thr Cys Gly Asp Val Glu Glu Asn Pro Gly Pro
```

```
1               5                   10
```

<210> SEQ ID NO 44
<211> LENGTH: 23
<212> TYPE: PRT
<213> ORGANISM: Artificial Sequence
<220> FEATURE:
<223> OTHER INFORMATION: Self-cleaving polypeptide comprising 2A site

<400> SEQUENCE: 44

```
Gly Ser Gly Gln Cys Thr Asn Tyr Ala Leu Leu Lys Leu Ala Gly Asp
1               5                   10                  15

Val Glu Ser Asn Pro Gly Pro
            20
```

<210> SEQ ID NO 45
<211> LENGTH: 20
<212> TYPE: PRT
<213> ORGANISM: Artificial Sequence
<220> FEATURE:
<223> OTHER INFORMATION: Self-cleaving polypeptide comprising 2A site

<400> SEQUENCE: 45

```
Gln Cys Thr Asn Tyr Ala Leu Leu Lys Leu Ala Gly Asp Val Glu Ser
1               5                   10                  15

Asn Pro Gly Pro
            20
```

<210> SEQ ID NO 46
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 46

```
Leu Leu Lys Leu Ala Gly Asp Val Glu Ser Asn Pro Gly Pro
1               5                   10
```

<210> SEQ ID NO 47
<211> LENGTH: 25
<212> TYPE: PRT
<213> ORGANISM: Artificial Sequence
<220> FEATURE:
<223> OTHER INFORMATION: Self-cleaving polypeptide comprising 2A site

<400> SEQUENCE: 47

```
Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25
```

<210> SEQ ID NO 48
<211> LENGTH: 22
<212> TYPE: PRT
<213> ORGANISM: Artificial Sequence
<220> FEATURE:
<223> OTHER INFORMATION: Self-cleaving polypeptide comprising 2A site

<400> SEQUENCE: 48

```
Val Lys Gln Thr Leu Asn Phe Asp Leu Leu Lys Leu Ala Gly Asp Val
1               5                   10                  15

Glu Ser Asn Pro Gly Pro
            20
```

<210> SEQ ID NO 49
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 49

Leu Leu Lys Leu Ala Gly Asp Val Glu Ser Asn Pro Gly Pro
1               5                   10

<210> SEQ ID NO 50
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 50

Leu Leu Asn Phe Asp Leu Leu Lys Leu Ala Gly Asp Val Glu Ser Asn
1               5                   10                  15

Pro Gly Pro

<210> SEQ ID NO 51
<211> LENGTH: 19
<212> TYPE: PRT
<213> ORGANISM: Artificial Sequence
<220> FEATURE:
<223> OTHER INFORMATION: Self-cleaving polypeptide comprising 2A site

<400> SEQUENCE: 51

Thr Leu Asn Phe Asp Leu Leu Lys Leu Ala Gly Asp Val Glu Ser Asn
1               5                   10                  15

Pro Gly Pro

<210> SEQ ID NO 52
<211> LENGTH: 14
<212> TYPE: PRT
<213> ORGANISM: Artificial Sequence
<220> FEATURE:
<223> OTHER INFORMATION: Self-cleaving polypeptide comprising 2A site

<400> SEQUENCE: 52

Leu Leu Lys Leu Ala Gly Asp Val Glu Ser Asn Pro Gly Pro
1               5                   10

<210> SEQ ID NO 53
<211> LENGTH: 17
<212> TYPE: PRT
<213> ORGANISM: Artificial Sequence
<220> FEATURE:
<223> OTHER INFORMATION: Self-cleaving polypeptide comprising 2A site

<400> SEQUENCE: 53

Asn Phe Asp Leu Leu Lys Leu Ala Gly Asp Val Glu Ser Asn Pro Gly
1               5                   10                  15

Pro

<210> SEQ ID NO 54
<211> LENGTH: 20
<212> TYPE: PRT
<213> ORGANISM: Artificial Sequence
<220> FEATURE:
<223> OTHER INFORMATION: Self-cleaving polypeptide comprising 2A site -continued

<400> SEQUENCE: 54

Gln Leu Leu Asn Phe Asp Leu Leu Lys Leu Ala Gly Asp Val Glu Ser
1               5                   10                  15

Asn Pro Gly Pro
            20

<210> SEQ ID NO 55
<211> LENGTH: 24
<212> TYPE: PRT
<213> ORGANISM: Artificial Sequence
<220> FEATURE:
<223> OTHER INFORMATION: Self-cleaving polypeptide comprising 2A site

<400> SEQUENCE: 55

Ala Pro Val Lys Gln Thr Leu Asn Phe Asp Leu Leu Lys Leu Ala Gly
1               5                   10                  15

Asp Val Glu Ser Asn Pro Gly Pro
            20

<210> SEQ ID NO 56
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 56

Val Thr Glu Leu Leu Tyr Arg Met Lys Arg Ala Glu Thr Tyr Cys Pro
1               5                   10                  15

Arg Pro Leu Leu Ala Ile His Pro Thr Glu Ala Arg His Lys Gln Lys
            20                  25                  30

Ile Val Ala Pro Val Lys Gln Thr
        35                  40

<210> SEQ ID NO 57
<211> LENGTH: 18
<212> TYPE: PRT
<213> ORGANISM: Artificial Sequence
<220> FEATURE:
<223> OTHER INFORMATION: Self-cleaving polypeptide comprising 2A site

<400> SEQUENCE: 57

Leu Asn Phe Asp Leu Leu Lys Leu Ala Gly Asp Val Glu Ser Asn Pro
1               5                   10                  15

Gly Pro

<210> SEQ ID NO 58
<211> LENGTH: 40
<212> TYPE: PRT
<213> ORGANISM: Artificial Sequence
<220> FEATURE:
<223> OTHER INFORMATION: Self-cleaving polypeptide comprising 2A site

<400> SEQUENCE: 58

Leu Leu Ala Ile His Pro Thr Glu Ala Arg His Lys Gln Lys Ile Val
1               5                   10                  15

Ala Pro Val Lys Gln Thr Leu Asn Phe Asp Leu Leu Lys Leu Ala Gly
            20                  25                  30

Asp Val Glu Ser Asn Pro Gly Pro
        35                  40

<210> SEQ ID NO 59

-continued

```
<211> LENGTH: 33
<212> TYPE: PRT
<213> ORGANISM: Artificial Sequence
<220> FEATURE:
<223> OTHER INFORMATION: Self-cleaving polypeptide comprising 2A site

<400> SEQUENCE: 59

Glu Ala Arg His Lys Gln Lys Ile Val Ala Pro Val Lys Gln Thr Leu
1               5                   10                  15

Asn Phe Asp Leu Leu Lys Leu Ala Gly Asp Val Glu Ser Asn Pro Gly
            20                  25                  30

Pro

<210> SEQ ID NO 60
<211> LENGTH: 10
<212> TYPE: DNA
<213> ORGANISM: Artificial Sequence
<220> FEATURE:
<223> OTHER INFORMATION: Consensus Kozak sequence

<400> SEQUENCE: 60 gccrccatgg                                                          10

<210> SEQ ID NO 61
<211> LENGTH: 30
<212> TYPE: DNA
<213> ORGANISM: Homo sapiens

<400> SEQUENCE: 61
gccaggtgga ggtgtatctc ttagatacca                                    30

<210> SEQ ID NO 62
<211> LENGTH: 30
<212> TYPE: DNA
<213> ORGANISM: Homo sapiens

<400> SEQUENCE: 62
tggtatctaa gagatacacc tccacctggc                                    30

<210> SEQ ID NO 63
<211> LENGTH: 297
<212> TYPE: PRT
<213> ORGANISM: Ophiostoma novo-ulmi

<400> SEQUENCE: 63

Ser Arg Arg Glu Ser Ile Asn Pro Trp Ile Leu Thr Gly Phe Ala Asp
1               5                   10                  15

Ala Glu Gly Ser Phe Leu Leu Arg Ile Arg Asn Asn Asn Lys Ser Ser
            20                  25                  30

Val Gly Tyr Ser Thr Glu Leu Gly Phe Gln Ile Thr His Asn Lys
        35                  40                  45

Asp Lys Ser Ile Leu Glu Asn Ile Gln Ser Thr Trp Lys Val Gly Val
    50                  55                  60

Ile Ala Asn Ser Gly Asp Asn Ala Val Ser Leu Lys Val Thr Arg Phe
65                  70                  75                  80

Glu Asp Leu Lys Val Ile Ile Asp His Phe Gly Lys Tyr Pro Leu Ile
                85                  90                  95

Thr Gln Lys Leu Gly Asp Tyr Met Leu Phe Lys Gln Ala Phe Cys Val
            100                 105                 110

Met Glu Asn Lys Glu His Leu Lys Ile Asn Gly Ile Lys Glu Leu Val
        115                 120                 125
```

```
Arg Ile Lys Ala Lys Leu Asn Trp Gly Leu Thr Asp Glu Leu Lys Lys
        130                 135                 140

Ala Phe Pro Glu Ile Ile Ser Lys Glu Arg Ser Leu Ile Asn Lys Asn
145                 150                 155                 160

Ile Pro Asn Phe Lys Trp Leu Ala Gly Phe Thr Ser Gly Glu Gly Cys
                165                 170                 175

Phe Phe Val Asn Leu Ile Lys Ser Lys Ser Lys Leu Gly Val Gln Val
                180                 185                 190

Gln Leu Val Phe Ser Ile Thr Gln His Ile Lys Asp Lys Asn Leu Met
        195                 200                 205

Asn Ser Leu Ile Thr Tyr Leu Gly Cys Gly Tyr Ile Lys Glu Lys Asn
        210                 215                 220

Lys Ser Glu Phe Ser Trp Leu Asp Phe Val Thr Lys Phe Ser Asp
225                 230                 235                 240

Ile Asn Asp Lys Ile Ile Pro Val Phe Gln Glu Asn Thr Leu Ile Gly
                245                 250                 255

Val Lys Leu Glu Asp Phe Glu Asp Trp Cys Lys Val Ala Lys Leu Ile
                260                 265                 270

Glu Glu Lys Lys His Leu Thr Glu Ser Gly Leu Asp Glu Ile Lys Lys
        275                 280                 285

Ile Lys Leu Asn Met Asn Lys Gly Arg
        290                 295

<210> SEQ ID NO 64
<211> LENGTH: 297
<212> TYPE: PRT
<213> ORGANISM: Artificial Sequence
<220> FEATURE:
<223> OTHER INFORMATION: Synthesized I-OnuI variant PCSK9.H7

<400> SEQUENCE: 64

Ser Arg Arg Glu Ser Ile Asn Pro Trp Ile Leu Thr Gly Phe Ala Asp
1               5                   10                  15

Ala Glu Gly Cys Phe Met Leu Asn Ile Trp Asn Lys Asn Arg Thr Arg
                20                  25                  30

Ala Lys Tyr Tyr Thr Ala Leu Arg Phe Glu Ile Ala Leu His Asn Lys
            35                  40                  45

Asp Lys Ser Ile Leu Glu Asn Ile Arg Ser Thr Trp Lys Val Gly Lys
50                  55                  60

Ile Arg Asn Ile Gly Asp Arg Val Val Lys Leu Val Val Gly Arg Phe
65                  70                  75                  80

Glu Asp Leu Lys Val Ile Ile Asp His Phe Glu Lys Tyr Pro Leu Ile
                85                  90                  95

Thr Gln Lys Leu Gly Asp Tyr Lys Leu Phe Lys Gln Ala Phe Ser Leu
            100                 105                 110

Met Glu Asn Lys Glu His Leu Lys Glu Asn Gly Ile Lys Glu Leu Val
        115                 120                 125

Arg Ile Lys Ala Lys Met Asn Trp Gly Leu Asn Asp Glu Leu Lys Lys
        130                 135                 140

Ala Phe Pro Glu Asn Ile Ser Lys Glu Arg Pro Leu Ile Asn Lys Asn
145                 150                 155                 160

Ile Pro Asn Leu Lys Trp Leu Ala Gly Phe Thr Ser Gly Asp Gly Tyr
                165                 170                 175

Phe Gly Val Glu Leu Met Lys Arg Lys Thr Gly Thr His Val Thr Val
                180                 185                 190
```

```
Arg Leu Arg Phe Ser Ile Ala Gln His Ile Arg Asp Lys Asn Leu Met
        195                 200                 205

Asn Ser Leu Ile Thr Tyr Leu Gly Cys Gly Arg Ile Ser Glu Arg Asn
        210                 215                 220

Lys Ser Glu Tyr Ser Trp Leu Glu Phe Val Val Thr Lys Phe Ser Asp
225                 230                 235                 240

Ile Asn Asp Lys Ile Ile Pro Val Phe Gln Glu Asn Thr Leu Ile Gly
            245                 250                 255

Val Lys Leu Glu Asp Phe Glu Asp Trp Cys Lys Val Ala Lys Leu Ile
                260                 265                 270

Glu Glu Lys Lys His Leu Thr Glu Ser Gly Leu Asp Glu Ile Lys Lys
            275                 280                 285

Ile Lys Leu Asn Met Asn Lys Gly Arg
        290                 295
```

<210> SEQ ID NO 65
<211> LENGTH: 297
<212> TYPE: PRT
<213> ORGANISM: Artificial Sequence
<220> FEATURE:
<223> OTHER INFORMATION: Synthesized I-OnuI variant PCSK9.H7.C11

<400> SEQUENCE: 65

```
Ser Arg Arg Glu Ser Ile Asn Pro Trp Ile Leu Thr Gly Phe Ala Asp
1               5                   10                  15

Ala Glu Gly Cys Phe Met Leu Asn Ile Trp Asn Lys Asn Arg Thr Arg
            20                  25                  30

Ala Lys Tyr Tyr Thr Ala Leu Arg Phe Glu Ile Ala Leu His Asn Lys
        35                  40                  45

Asp Lys Ser Ile Leu Glu Asn Ile Arg Ser Thr Trp Lys Val Gly Lys
    50                  55                  60

Ile Arg Asn Ile Gly Asp Arg Val Val Lys Leu Val Val Gly Arg Phe
65                  70                  75                  80

Glu Asp Leu Lys Val Ile Ile Asp His Phe Glu Lys Tyr Pro Leu Ile
                85                  90                  95

Thr Gln Lys Leu Gly Asp Tyr Lys Leu Phe Lys Gln Ala Phe Ser Leu
            100                 105                 110

Met Glu Asn Lys Glu His Leu Lys Glu Asn Gly Ile Lys Glu Leu Val
        115                 120                 125

Arg Ile Lys Ala Lys Met Asn Trp Gly Leu Asn Asp Glu Leu Lys Lys
    130                 135                 140

Ala Phe Pro Glu Asn Ile Ser Lys Glu Arg Pro Leu Ile Asn Lys Asn
145                 150                 155                 160

Ile Pro Asn Leu Lys Trp Leu Ala Gly Phe Thr Ser Gly Asp Gly Tyr
                165                 170                 175

Phe Gly Val Glu Leu Met Lys Arg Thr Thr Gly Thr His Val Thr Val
            180                 185                 190

Arg Leu Arg Phe Ser Ile Thr Gln His Ile Arg Asp Lys Asn Leu Met
        195                 200                 205

Asn Ser Leu Ile Thr Tyr Leu Gly Cys Gly Arg Ile Ser Glu Arg Asn
    210                 215                 220

Lys Ser Glu Tyr Ser Trp Leu Glu Phe Val Val Thr Lys Phe Ser Asp
225                 230                 235                 240

Ile Asn Asp Lys Ile Ile Pro Val Phe Gln Glu Asn Thr Leu Ile Gly
                245                 250                 255
```

```
Val Lys Leu Glu Asp Phe Glu Asp Trp Cys Lys Val Ala Lys Leu Ile
            260             265                 270

Glu Glu Lys Lys His Leu Thr Glu Ser Gly Leu Asp Glu Ile Lys Lys
        275             280                 285

Ile Lys Leu Asn Met Asn Lys Gly Arg
    290             295

<210> SEQ ID NO 66
<211> LENGTH: 45
<212> TYPE: DNA
<213> ORGANISM: Homo sapiens

<400> SEQUENCE: 66
tgggcaccct ggatgctggt atctaagaga tacacctcca cctgg          45

<210> SEQ ID NO 67
<211> LENGTH: 45
<212> TYPE: DNA
<213> ORGANISM: Homo sapiens

<400> SEQUENCE: 67
ccaggtggag gtgtatctct tagataccag catccagggt gccca          45
```